US008530437B2

(12) United States Patent
Brown et al.

(10) Patent No.: US 8,530,437 B2
(45) Date of Patent: Sep. 10, 2013

(54) METHODS FOR TREATING CANCER USING HERPES SIMPLEX VIRUS EXPRESSING ANTISENSE TO THE SQUAMOUS CELL CARCINOMA RELATED ONCOGENE

(75) Inventors: Susanne Moira Brown, Glasgow (GB); Paul Dunn, Glasgow (GB); Bhuvanesh Singh, Old Westbury, NY (US); Ian Ganly, New York, NY (US)

(73) Assignees: Sloan Kettering Institute for Cancer Research, New York, NY (US); Virttu Biologics Limited, Glasgow (GB)

( * ) Notice: Subject to any disclaimer, the term of this patent is extended or adjusted under 35 U.S.C. 154(b) by 387 days.

(21) Appl. No.: 12/436,382

(22) Filed: May 6, 2009

(65) Prior Publication Data
US 2009/0274728 A1    Nov. 5, 2009

Related U.S. Application Data

(63) Continuation of application No. 10/579,622, filed as application No. PCT/GB2004/004908 on Nov. 17, 2004, now abandoned.

(60) Provisional application No. 60/541,308, filed on Feb. 3, 2004.

(30) Foreign Application Priority Data

Nov. 17, 2003  (GB) .................................. 0326798.6

(51) Int. Cl.
| C12N 15/11 | (2006.01) |
| A61K 38/00 | (2006.01) |
| C07H 21/04 | (2006.01) |
| C12Q 1/68  | (2006.01) |

(52) U.S. Cl.
CPC ..................................... *A61K 38/00* (2013.01)
USPC .......................... 514/44 A; 536/24.5; 435/6.1

(58) Field of Classification Search
None
See application file for complete search history.

(56) References Cited

U.S. PATENT DOCUMENTS

| 5,922,576 | A  |   | 7/1999  | He et al. |
| 6,025,127 | A  |   | 2/2000  | Sidransky |
| 6,428,968 | B1 | * | 8/2002  | Molnar-Kimber et al. .. 435/7.23 |
| 6,573,090 | B1 |   | 6/2003  | Breakefield et al. |
| 2002/0164666 | A1 | * | 11/2002 | Cimbora et al. ............. 435/7.23 |
| 2003/0022329 | A1 |   | 1/2003  | Tang et al. |
| 2004/0009541 | A1 |   | 1/2004  | Singh et al. |
| 2004/0048277 | A1 |   | 3/2004  | Echeverri et al. |

FOREIGN PATENT DOCUMENTS

| EP | 0353851 | 2/1990 |
| EP | 0538496 | 4/1993 |
| EP | 0753581 | 1/1997 |
| WO | 95/04139 | 2/1995 |
| WO | 96/05291 | 2/1996 |
| WO | WO 96/03997 | 2/1996 |
| WO | 97/04804 | 2/1997 |
| WO | 97/14808 | 4/1997 |
| WO | WO 97/26904 | 7/1997 |
| WO | 98/51809 | 11/1998 |
| WO | WO 99/38955 | 8/1999 |
| WO | 00/52165 | 9/2000 |
| WO | 01/16331 | 3/2001 |
| WO | 01/46449 | 6/2001 |
| WO | WO 0238805 A2 * | 5/2002 |
| WO | 03/008573 | 1/2003 |
| WO | WO 03/068809 | 8/2003 |
| WO | 2004/096142 | 11/2004 |
| WO | WO 2005/049844 | 6/2005 |
| WO | WO 2005/049846 | 6/2005 |
| WO | WO 2007/026146 | 3/2007 |
| WO | WO 2007/132169 | 11/2007 |
| WO | WO 2008/099189 | 8/2008 |
| WO | WO 2009/013448 | 1/2009 |

OTHER PUBLICATIONS

Xi et al., Gene therapy for the treatment of oral squamous cell carcinoma, 2003, Journal of Dental Research, vol. 82, pp. 11-16.*
Burton, Edward A., et al., "Gene Delivery Using Herpes Simplex Virus Vectors," DNA and Cell Biology, vol. 21, No. 12, 2002, pp. 915-936.
Coukos et al., "Use of carrier cells to deliver a replication-selective herpes simplex virus-1 mutant for the intraperitoneal therapy of epithelial ovarian cancer," Clinical Cancer Research, Jun. 1999, vol. 5, pp. 1523-1537.
Crooke, Stanley T., "Potential roles of antisense technology in cancer chemotherapy," Oncogene, 2000, vol. 19, pp. 6651-6659.
Doepker, Rosalyn C. et al., "Herpes Simplex Virus Virion Host Shutoff Protein Is Stimulated by Translation Initiation Factors eIF4B and eIF4H," Journal of Virology, May 2004, pp. 4684-4699.
Elgadi, Mabrouk M. et al., "The Herpes Simplex Virus vhs Protein Induces Endoribonucleolytic Cleavage of Target RNAs in Cell Extracts," Journal of Virology, Sep. 1999, pp. 7153-7164.
EMBL Accession No. AF456425, "*Homo sapiens* leucine zipper protein (SCRO) mRNA, complete cds," (2002).
Estilo, et al., "The Role of Novel Oncogenes *Squamous Cell Carcinoma-related Oncogene* and *Phosphatidylinositol 3-Kinase p110a* in Squamous Cell Carcinoma of the Oral Tongue," Clinical Cancer Research, 2003, vol. 9, pp. 2300-2306.
Everly et al., "mRNA Degradation by the Virion Host Shutoff (Vhs) Protein of Herpes Simplex Virus: Genetic and Biochemical Evidence that Vhs is a Nuclease", Journal of Virology, 2002, vol. 76, pp. 8560-8571.

(Continued)

*Primary Examiner* — Dana Shin
(74) *Attorney, Agent, or Firm* — Swanson & Bratschun, LLC

(57) ABSTRACT

An herpes simplex virus wherein the herpes simplex virus genome comprises nucleic acid encoding an antisense to the squamous cell carcinoma related oncogene (asSCCRO); and an herpes simplex virus wherein the herpes simplex virus genome comprises nucleic acid encoding a short interfering ribonucleic acid (siRNA) molecule that is capable of repressing or silencing expression of squamous cell carcinoma related oncogene (SCCRO) nucleic acid or polypeptide are disclosed together with methods for generation and applications of such viruses.

11 Claims, 26 Drawing Sheets

(56) References Cited

OTHER PUBLICATIONS

Glenn, Gary M., and Chatterjee, Subhendra, "Generation of Adenoviruses Encoding the Herpes Simplex Virus vhs gene: A Novel Strategy to Generate Adenoviruses Expressing Genes Toxic to Producer Cells," Cancer Gene Therapy, vol. 8, No. 8, 2001, pp. 566-572.
Gomez-Lira, et al., "CD45 and multiple sclerosis: the exon 4 C77G polymorphism (additional studies and meta-analysis) and new markers," Journal of Neuroimmunology, 2003, vol. 140, pp. 216-221.
Jacobs, et al., "Improved herpes simplex virus type 1 amplicon vector for proportional coexpression of positron emission tomography marker and therapeutic genes," Gene Therapy, 2003, vol. 14, pp. 277-297.
Karl, Ilkka et al., "Antisense RNA Directed to the Human Papillomavirus type 16 E7 mRNA From Herpes Simplex Virus Type I Derived Vectors is Expressed in CaSki Cells and Downregulates E7 mRNA," Virology Journal, Jun. 2007, 11 pages.
Kwong, Ann D. and Frenkel, Niza, "Herpes Simplex Virus-Infected Cells Contain a Functions(s) That Destabilizes Both Host and Viral mRNAs," Proc. National Academy of Sciences USA, Apr. 1987, vol. 83, pp. 1926-1930.
Lu, Patricia et al., "Herpes Simplex Virus Virion Host Shutoff Protein Requires a Mammalian Factor for Efficient In Vitro Endoribonuclease Activity," Journal of Virology, Feb. 2001, pp. 1172-1185.
Nemunaitis, J., "Selective replicating viral vectors: potential for use in cancer gene therapy," Biodrugs, 2003, vol. 17, pp. 251-262.
Rampling, R., et al., "Toxicity evaluation of replication-competent herpes simplex virus (ICP 34.5 null mutant 1716) in patients with recurrent malignant glioma," Gene Therapy, 2000, vol. 7, pp. 259-866.
Read, G. Sullivan and Frenkel, Niza, "Herpes Simplex Virus Mutants Defective in the Virion-Associated Shutoff of Host Polypeptide Synthesis and Exhibiting Abnormal Synthesis of α (Immediate Early) Viral Polypeptides," Journal of Virology, May 1983, pp. 498-512.
Sarma, Nandini et al., "Small Interfering RNAs That Deplete the Cellular Translation Factor eIF4H Impeded mRNA Degradation by the Virion Host Shutoff Protein of Herpes Simplex Virus," Journal of Virology, Jul. 2008, pp. 6600-6609.
Schmidt Pak, Annette et al., "The Virion Host Shutoff Protein of Herpes Simplex Virus Inhibits Reporter Gene Expression in the Absence of Other Viral Gene Products," Virology, vol. 211, 1995, pp. 491-506.
Smibert, Craig A. and Smiley, James R., "Differential Regulation of Endogenous and Transduced β-Globin Genes During Infection of Erythroid Cells with a Herpes Simplex Virus Type 1 Recombinant," Journal of Virology, Aug. 1990, pp. 3882-3894.
Smibert, Craig A. et al., "Identification and Characterization of the Virion-Induced Host Shutoff Product of Herpes Simplex Virus Gene UL41," Journal of General Virology, 1992, vol. 73, pp. 467-470.
Strom, Ted and Frenkel, Niza, "Effects of Herpes Simplex Virus on mRNA Stability," Journal of Virology, Jul. 1987, pp. 2198-2207.
Toyoizumi et al., "Combined therapy with chemotherapeutic agents and herpes simplex virus type 1 ICP34.5 mutant (HSV-1716) in human non-small cell lung cancer," Human Gene Therapy, 1999, vol. 10, pp. 3013-3029.
Wong, et al., "Oncolytic Herpesvirus Effectively Treats Murine Squamous Cell Carcinoma and Spreads by Natural Lymphatics to Treat Sites of Lymphatic Metastases," Human Gene Therapy, 2002, vol. 13, pp. 1213-1223.
Anesti et al. (2010) BMC Cancer 10:486, "Expression of RNA interference triggers from an oncolytic herpes simplex virus results in specific silencing in tumour cells in vitro and tumours in vivo".
Coukos et al. (1999) Clinical Cancer Research, 5:1523-1537, "Use of Carrier Cells to Deliver a Replication-selective Herpes Simplex Virus-1 Mutant for the Intraperitoneal Therapy of Epithelial Ovarian Cancer$_1$".
Fraefel et al. (1996) Journal of Virology, 70(10):7190-7197, "Helper Virus-Free Transfer of Herpes Simplex Virus Type 1 Plasmid Vectors into Neural Cells".
Holt et al. (1986) Proc. Natl. Acad. Sci, USA 83:4794-4798, "Inducible production of c-fos antisense RNA inhibits 3T3 cell proliferation".
Jones et al. (2003) Pain 106: 365-371, "Afferent fiber-selective shift in opiate potency following targeted opioid receptor knockdown".
Tang et al. (2009) Journal of Virology 83(3):1433-1442, "Novel Less-Abundant Viral MicroRNAs Encoded by Herpes Simplex Virus 2 Latency-Associated Transcript and Their Roles in Regulating ICP34.5 and ICP0 mRNAs".
Toda et al. (1998) The Journal of Immunology, 160:4457-4464, "In Situ Cancer Vaccination: An IL-12 Defective Vector/Replication-Competent Herpes Simplex Virus Combination Induces Local and Systemic Antitumor Activity".
Tzabazis et al. (2007) Anesthesiology, 106:1196-1203, "Antihyperalgesic Effect of a Recombinant Herpes Virus Encoding Antisense for Calcitonin Gene-related Peptide".
Umbach et al (2008) Nature, 454(7205):780-783, "MicroRNAs expressed by herpes simplex virus 1 during latent infection regulate viral mRNAs".

\* cited by examiner

SEQ ID No. 01

Figure 22a

SEQ ID No. 02

| | | | | | | | | | | | | | |
|---|---|---|---|---|---|---|---|---|---|---|---|---|---|
| Met | Asn | Lys | Leu | Lys | Ser | Ser | Gln | Lys | Asp | Lys | Val | Arg | Gln | Phe | Met |
| 1 | | | | 5 | | | | | 10 | | | | | 15 | |

| Ile | Phe | Thr | Gln | Ser | Ser | Glu | Lys | Thr | Ala | Val | Ser | Cys | Leu | Ser | Gln |
| 20 | | | | | 25 | | | | | 30 | | | | | |

Asn Asp Trp Lys Leu Asp Val Ala Thr Asp Asn Phe Phe Gln Asn Pro
                35                    40                    45

Glu Leu Tyr Ile Arg Glu Ser Val Lys Gly Ser Leu Asp Arg Lys Lys
       50                    55                    60

Leu Glu Gln Leu Tyr Asn Arg Tyr Lys Asp Pro Gln Asp Glu Asn Lys
65                    70                    75                    80

Ile Gly Ile Asp Gly Ile Gln Gln Phe Cys Asp Asp Leu Ala Leu Asp
                85                    90                    95

Pro Ala Ser Ile Ser Val Leu Ile Ile Ala Trp Lys Phe Arg Ala Ala
                100                   105                   110

Thr Gln Cys Glu Phe Ser Lys Gln Glu Phe Met Asp Gly Met Thr Glu
       115                   120                   125

Leu Gly Cys Asp Ser Ile Glu Lys Leu Lys Ala Gln Ile Pro Lys Met
130                   135                   140

Glu Gln Glu Leu Lys Gln Pro Gly Arg Phe Lys Asp Phe Tyr Gln Phe
145                   150                   155                   160

Thr Phe Asn Phe Ala Lys Asn Pro Gly Gln Lys Gly Leu Asp Leu Glu
                165                   170                   175

Met Ala Ile Ala Tyr Trp Asn Leu Val Leu Asn Gly Arg Phe Lys Phe
                180                   185                   190

Leu Asp Leu Trp Asn Lys Phe Leu Leu Glu His His Lys Arg Ser Ile
                195                   200                   205

Pro Lys Asp Thr Trp Asn Leu Leu Leu Asp Phe Ser Thr Met Ile Ala
       210                   215                   220

Asp Asp Met Ser Asn Tyr Asp Glu Gly Ala Trp Pro Val Leu Ile
225                   230                   235                   240

Asp Asp Phe Val Glu Phe Ala Arg Pro Gln Ile Ala Gly Thr Lys Ser
                245                   250                   255

Thr Thr Val

Figure 22b

SEQ ID No.03

```
ctggaggaca ccaac atg aac aag ttg aaa tca tcg cag aag gat aaa gtt          51
              Met Asn Lys Leu Lys Ser Ser Gln Lys Asp Lys Val
              1               5                   10 cgt cag ttt atg atc ttc aca caa tct agt gaa aaa aca gca gta agt           99
Arg Gln Phe Met Ile Phe Thr Gln Ser Ser Glu Lys Thr Ala Val Ser
        15                  20                  25 tgt ctt tct caa aat gac tgg aag tta gat gtt gca aca gat aat ttt          147
Cys Leu Ser Gln Asn Asp Trp Lys Leu Asp Val Ala Thr Asp Asn Phe
    30                  35                  40 ttc caa aat cct gaa ctt tct ata cga gag agt gta aaa gga tca ttg          195
Phe Gln Asn Pro Glu Leu Tyr Ile Arg Glu Ser Val Lys Gly Ser Leu
45                  50                  55                  60 gac agg aag aag tta gaa cag ctg tac aat aga tac aaa gac cct caa          243
Asp Arg Lys Lys Leu Glu Gln Leu Tyr Asn Arg Tyr Lys Asp Pro Gln
                65                  70                  75 gat gag aat aaa att gga atc gat ggc ata cag cag ttc tgt gat gac          291
Asp Glu Asn Lys Ile Gly Ile Asp Gly Ile Gln Gln Phe Cys Asp Asp
            80                  85                  90 ctg gca ctc gat cca gca agc att agt gtg ttg att att gcg tgg aag          339
Leu Ala Leu Asp Pro Ala Ser Ile Ser Val Leu Ile Ile Ala Trp Lys
        95                  100                 105 ttc aga gca gca aca cag tgc gag ttc tcc aaa cag gag ttc atg gat          387
Phe Arg Ala Ala Thr Gln Cys Glu Phe Ser Lys Gln Glu Phe Met Asp
    110                 115                 120 ggc atg aca gaa tta gga tgt gac agc aca gaa aaa cta aag gcc cag          435
Gly Met Thr Glu Leu Gly Cys Asp Ser Thr Glu Lys Leu Lys Ala Gln
125                 130                 135                 140 ata ccc aag atg gaa caa gaa ttg aaa gaa cca gga aga ttt aag gat          483
Ile Pro Lys Met Glu Gln Glu Leu Lys Glu Pro Gly Arg Phe Lys Asp
                145                 150                 155 ttt tac cag ttt act ttt aat ttt gca aag aat cca gga caa aaa gga          531
Phe Tyr Gln Phe Thr Phe Asn Phe Ala Lys Asn Pro Gly Gln Lys Gly
            160                 165                 170 tta gat cta gaa atg gca att gcc tac tgg aac tta gtg ctt aat gga          579
Leu Asp Leu Glu Met Ala Ile Ala Tyr Trp Asn Leu Val Leu Asn Gly
        175                 180                 185 aga ttt aga ctc tta gac tta tgg aat aaa ttt ttg gaa cat cat          627
Arg Phe Arg Leu Leu Asp Leu Trp Asn Lys Phe Leu Glu His His
    190                 195                 200 aaa cga tca ata cca aaa gac act tgg aat ctt tta gac ttc agt          675
Lys Arg Ser Ile Pro Lys Asp Thr Trp Asn Leu Leu Asp Phe Ser
205                 210                 215                 220 acg atg att gca gat gac atg tct aat tat gat gaa gga gca tgg          723
Thr Met Ile Ala Asp Asp Met Ser Asn Tyr Asp Glu Gly Ala Trp
                225                 230                 235 cct gtt ctt att gat gac ttt gtg gaa ttt gca cgc cct caa att gct          771
Pro Val Leu Ile Asp Asp Phe Val Glu Phe Ala Arg Pro Gln Ile Ala
            240                 245                 250 ggg aca aaa agt aca aca gtg tag cactaaagga acctctaga atgtacatag          825
Gly Thr Lys Ser Thr Thr Val  *
            255 tctgtacaat aaatacaaca gaaaattgca aagtcaattt ctgctggctg g                 876
```

Figure 22c

SEQ ID No. 04

Met Asn Lys Leu Lys Ser Ser Gln Lys Asp Lys Val Arg Gln Phe Met
1               5                   10                  15

Ile Phe Thr Gln Ser Ser Glu Lys Thr Ala Val Ser Cys Leu Ser Gln
            20                  25                  30

Asn Asp Trp Lys Leu Asp Val Ala Thr Asn Phe Phe Gln Asn Pro
        35                  40                  45

Glu Leu Tyr Ile Arg Glu Ser Val Lys Gly Ser Leu Asp Arg Lys Lys
        50                  55                  60

Leu Glu Gln Leu Tyr Asn Arg Tyr Lys Asp Pro Gln Asp Gln Asn Lys
65                  70                  75                  80

Ile Gly Ile Asp Gly Ile Gln Gln Phe Cys Asp Asp Leu Ala Leu Asp
                85                  90                  95

Pro Ala Ser Ile Ser Val Leu Ile Ile Ala Trp Lys Phe Arg Ala Ala
            100                 105                 110

Thr Gln Cys Glu Phe Ser Lys Gln Glu Phe Met Asp Gly Met Thr Glu
        115                 120                 125

Leu Gly Cys Asp Ser Thr Glu Lys Leu Lys Ala Gln Ile Pro Lys Met
    130                 135                 140

Gln Gln Glu Leu Lys Glu Pro Gly Arg Phe Lys Asp Phe Tyr Gln Phe
145                 150                 155                 160

Thr Phe Asn Phe Ala Lys Asn Pro Gly Gln Lys Gly Leu Asp Leu Glu
                165                 170                 175

Met Ala Ile Ala Tyr Trp Asn Leu Val Leu Asn Gly Arg Phe Arg Leu

Leu Asp Leu Trp Asn Lys Phe Leu Leu Glu His His Lys Arg Ser Ile
        195                 200                 205

Pro Lys Asp Thr Trp Asn Leu Leu Leu Asp Phe Ser Thr Met Ile Ala
    210                 215                 220

Asp Asp Met Ser Asn Tyr Asp Glu Glu Gly Ala Trp Pro Val Leu Ile
225                 230                 235                 240

Asp Asp Phe Val Glu Phe Ala Arg Pro Gln Ile Ala Gly Thr Lys Ser
            245                 250                 255

Thr Thr Val

Figure 22d

(A) 339isiRNA (SEQ ID No. 05)

gatcCCCGTTCAGAGCAGCAACACAGTTCAAGAGACTGTGTTGCTGCTCTGAA
CTTTTTGGAAA

(B) ConisiRNA (SEQ ID No.06)

gatcCCCCGTCTACCTACACTCCCTCTTCAAGAGAGGGAGTGTAGGTAGAC
GTTTTTA

Figure 23

SEQUENCE LISTING

```
<160> NUMBER OF SEQ ID NOS: 6

<210> SEQ ID NO 1
<211> LENGTH: 918
<212> TYPE: DNA
<213> ORGANISM: Homo sapiens
<220> FEATURE:
<221> NAME/KEY: CDS
<222> LOCATION: (58)..(837)

<400> SEQUENCE: 1
cgccgtccat tcgctgcgga gccggaggag gaggggagag gcctggagga caccaac         57 atg aac aag ttg aaa tca tcg cag aag gat aaa gtt cgt cag ttt atg      105
Met Asn Lys Leu Lys Ser Ser Gln Lys Asp Lys Val Arg Gln Phe Met
1               5                  10                  15 atc ttc aca caa tct agt gaa aaa aca gca gta agt tgt ctt tct caa      153
Ile Phe Thr Gln Ser Ser Glu Lys Thr Ala Val Ser Cys Leu Ser Gln
            20                  25                  30 aat gac tgg aag tta gat gtt gca aca gat aat ttt ttc caa aat cct      201
Asn Asp Trp Lys Leu Asp Val Ala Thr Asp Asn Phe Phe Gln Asn Pro
        35                  40                  45 gaa ctt tat ata cga gag agt gta aaa gga tca ttg gac agg aag aag      249
Glu Leu Tyr Ile Arg Glu Ser Val Lys Gly Ser Leu Asp Arg Lys Lys
    50                  55                  60 tta gaa cag ctg tac aat aga tac aaa gac cct caa gat gag aat aaa      297
Leu Glu Gln Leu Tyr Asn Arg Tyr Lys Asp Pro Gln Asp Glu Asn Lys
65                  70                  75                  80 att gga ata gat ggc ata cag cag ttc tgt gat gac ctg gca ctc gat      345
Ile Gly Ile Asp Gly Ile Gln Gln Phe Cys Asp Asp Leu Ala Leu Asp
                85                  90                  95 cca gcc agc att agt gtg ttg att att gca tgg aag ttc aga gca gca      393
Pro Ala Ser Ile Ser Val Leu Ile Ile Ala Trp Lys Phe Arg Ala Ala
            100                 105                 110 aca cag tgc gag ttc tcc aaa cag gag ttc atg gat ggc atg aca gaa      441
Thr Gln Cys Glu Phe Ser Lys Gln Glu Phe Met Asp Gly Met Thr Glu
        115                 120                 125 tta gga tgt gac agc ata gaa aaa cta aag gcc cag ata ccc aag atg      489
Leu Gly Cys Asp Ser Ile Glu Lys Leu Lys Ala Gln Ile Pro Lys Met
    130                 135                 140
```

```
gaa caa gaa ttg aaa gaa cca gga cga ttt aag gat ttt tac cag ttt      537
Glu Gln Glu Leu Lys Glu Pro Gly Arg Phe Lys Asp Phe Tyr Gln Phe
145                 150                 155                 160 act ttt aat ttt gca aag aat cca gga caa aaa gga tta gat cta gaa      585
Thr Phe Asn Phe Ala Lys Asn Pro Gly Gln Lys Gly Leu Asp Leu Glu
                165                 170                 175 atg gcc att gcc tac tgg aac tta gtg ctt aat gga aga ttt aaa ttc      633
Met Ala Ile Ala Tyr Trp Asn Leu Val Leu Asn Gly Arg Phe Lys Phe
            180                 185                 190 tta gac tta tgg aat aaa ttt ttg ttg gaa cat cat aaa cga tca ata      681
Leu Asp Leu Trp Asn Lys Phe Leu Leu Glu His His Lys Arg Ser Ile
        195                 200                 205 cca aaa gac act tgg aat ctt ctt tta gac ttc agt acg atg att gca      729
Pro Lys Asp Thr Trp Asn Leu Leu Leu Asp Phe Ser Thr Met Ile Ala
    210                 215                 220 gat gac atg tct aat tat gat gaa gaa gga gca tgg cct gtt ctt att      777
Asp Asp Met Ser Asn Tyr Asp Glu Glu Gly Ala Trp Pro Val Leu Ile
225                 230                 235                 240 gat gac ttt gtg gaa ttt gca cgc cct caa att gct ggg aca aaa agt      825
Asp Asp Phe Val Glu Phe Ala Arg Pro Gln Ile Ala Gly Thr Lys Ser
                245                 250                 255 aca aca gtg tag cactaaagga accttctaga atgtacatag tctgtacaat          877
Thr Thr Val aaatacaaca gaaaattgca cagtcaattt ctgctggctg g                        918

<210> SEQ ID NO 2
<211> LENGTH: 259
<212> TYPE: PRT
<213> ORGANISM: Homo sapiens

<400> SEQUENCE: 2

Met Asn Lys Leu Lys Ser Ser Gln Lys Asp Lys Val Arg Gln Phe Met
1               5                   10                  15

Ile Phe Thr Gln Ser Ser Glu Lys Thr Ala Val Ser Cys Leu Ser Gln
            20                  25                  30

Asn Asp Trp Lys Leu Asp Val Ala Thr Asp Asn Phe Phe Gln Asn Pro
        35                  40                  45

Glu Leu Tyr Ile Arg Glu Ser Val Lys Gly Ser Leu Asp Arg Lys Lys
    50                  55                  60

Leu Glu Gln Leu Tyr Asn Arg Tyr Lys Asp Pro Gln Asp Glu Asn Lys
65                  70                  75                  80

Ile Gly Ile Asp Gly Ile Gln Gln Phe Cys Asp Asp Leu Ala Leu Asp
                85                  90                  95

Pro Ala Ser Ile Ser Val Leu Ile Ile Ala Trp Lys Phe Arg Ala Ala
            100                 105                 110

Thr Gln Cys Glu Phe Ser Lys Gln Glu Phe Met Asp Gly Met Thr Glu
        115                 120                 125

Leu Gly Cys Asp Ser Ile Glu Lys Leu Lys Ala Gln Ile Pro Lys Met
    130                 135                 140

Glu Gln Glu Leu Lys Glu Pro Gly Arg Phe Lys Asp Phe Tyr Gln Phe
145                 150                 155                 160

Thr Phe Asn Phe Ala Lys Asn Pro Gly Gln Lys Gly Leu Asp Leu Glu
                165                 170                 175

Met Ala Ile Ala Tyr Trp Asn Leu Val Leu Asn Gly Arg Phe Lys Phe
            180                 185                 190

Leu Asp Leu Trp Asn Lys Phe Leu Leu Glu His His Lys Arg Ser Ile
        195                 200                 205
```

```
Pro Lys Asp Thr Trp Asn Leu Leu Asp Phe Ser Thr Met Ile Ala
    210                 215                 220

Asp Asp Met Ser Asn Tyr Asp Glu Glu Gly Ala Trp Pro Val Leu Ile
225                 230                 235                 240

Asp Asp Phe Val Glu Phe Ala Arg Pro Gln Ile Ala Gly Thr Lys Ser
                245                 250                 255

Thr Thr Val

<210> SEQ ID NO 3
<211> LENGTH: 876
<212> TYPE: DNA
<213> ORGANISM: Homo sapiens
<220> FEATURE:
<221> NAME/KEY: CDS
<222> LOCATION: (16)..(795)

<400> SEQUENCE: 3
ctggaggaca ccaac atg aac aag ttg aaa tca tcg cag aag gat aaa gtt         51
                Met Asn Lys Leu Lys Ser Ser Gln Lys Asp Lys Val
                  1               5                  10 cgt cag ttt atg atc ttc aca caa tct agt gaa aaa aca gca gta agt         99
Arg Gln Phe Met Ile Phe Thr Gln Ser Ser Glu Lys Thr Ala Val Ser
            15                  20                  25 tgt ctt tct caa aat gac tgg aag tta gat gtt gca aca gat aat ttt        147
Cys Leu Ser Gln Asn Asp Trp Lys Leu Asp Val Ala Thr Asp Asn Phe
    30                  35                  40 ttc caa aat cct gaa ctt tat ata cga gag agt gta aaa gga tca ttg        195
Phe Gln Asn Pro Glu Leu Tyr Ile Arg Glu Ser Val Lys Gly Ser Leu
45                  50                  55                  60 gac agg aag aag tta gaa cag ctg tac aat aga tac aaa gac cct caa        243
Asp Arg Lys Lys Leu Glu Gln Leu Tyr Asn Arg Tyr Lys Asp Pro Gln
                65                  70                  75 gat gag aat aaa att gga ata gat ggc ata cag cag ttc tgt gat gac        291
Asp Glu Asn Lys Ile Gly Ile Asp Gly Ile Gln Gln Phe Cys Asp Asp
            80                  85                  90 ctg gca ctc gat cca gcc agc att agt gtg ttg att att gcg tgg aag        339
Leu Ala Leu Asp Pro Ala Ser Ile Ser Val Leu Ile Ile Ala Trp Lys
        95                 100                 105 ttc aga gca gca aca cag tgc gag ttc tcc aaa cag gag ttc atg gat        387
Phe Arg Ala Ala Thr Gln Cys Glu Phe Ser Lys Gln Glu Phe Met Asp
    110                 115                 120 ggc atg aca gaa tta gga tgt gac agc aca gaa aaa cta aag gcc cag        435
Gly Met Thr Glu Leu Gly Cys Asp Ser Thr Glu Lys Leu Lys Ala Gln
125                 130                 135                 140 ata ccc aag atg gaa caa gaa ttg aaa gaa cca gga cga ttt aag gat        483
Ile Pro Lys Met Glu Gln Glu Leu Lys Glu Pro Gly Arg Phe Lys Asp
                145                 150                 155 ttt tac cag ttt act ttt aat ttt gca aag aat cca gga caa aaa gga        531
Phe Tyr Gln Phe Thr Phe Asn Phe Ala Lys Asn Pro Gly Gln Lys Gly
            160                 165                 170 tta gat cta gaa atg gcc att gcc tac tgg aac tta gtg ctt aat gga        579
Leu Asp Leu Glu Met Ala Ile Ala Tyr Trp Asn Leu Val Leu Asn Gly
        175                 180                 185 aga ttt aga ctc tta gac tta tgg aat aaa ttt ttg ttg gaa cat cat        627
Arg Phe Arg Leu Leu Asp Leu Trp Asn Lys Phe Leu Leu Glu His His
    190                 195                 200 aaa cga tca ata cca aaa gac act tgg aat ctt ctt tta gac ttc agt        675
Lys Arg Ser Ile Pro Lys Asp Thr Trp Asn Leu Leu Leu Asp Phe Ser
205                 210                 215                 220
```

```
acg atg att gca gat gac atg tct aat tat gat gaa gaa gga gca tgg      723
Thr Met Ile Ala Asp Asp Met Ser Asn Tyr Asp Glu Glu Gly Ala Trp
        225                 230                 235 cct gtt ctt att gat gac ttt gtg gaa ttt gca cgc cct caa att gct      771
Pro Val Leu Ile Asp Asp Phe Val Glu Phe Ala Arg Pro Gln Ile Ala
            240                 245                 250 ggg aca aaa agt aca aca gtg tag cactaaagga accttctaga atgtacatag     825
Gly Thr Lys Ser Thr Thr Val
            255 tctgtacaat aaatacaaca gaaaattgca cagtcaattt ctgctggctg g             876
```

<210> SEQ ID NO 4
<211> LENGTH: 259
<212> TYPE: PRT
<213> ORGANISM: Homo sapiens

<400> SEQUENCE: 4

```
Met Asn Lys Leu Lys Ser Ser Gln Lys Asp Lys Val Arg Gln Phe Met
1               5                   10                  15

Ile Phe Thr Gln Ser Ser Glu Lys Thr Ala Val Ser Cys Leu Ser Gln
            20                  25                  30

Asn Asp Trp Lys Leu Asp Val Ala Thr Asp Asn Phe Phe Gln Asn Pro
        35                  40                  45

Glu Leu Tyr Ile Arg Glu Ser Val Lys Gly Ser Leu Asp Arg Lys Lys
    50                  55                  60

Leu Glu Gln Leu Tyr Asn Arg Tyr Lys Asp Pro Gln Asp Glu Asn Lys
65                  70                  75                  80

Ile Gly Ile Asp Gly Ile Gln Gln Phe Cys Asp Asp Leu Ala Leu Asp
                85                  90                  95

Pro Ala Ser Ile Ser Val Leu Ile Ile Ala Trp Lys Phe Arg Ala Ala
            100                 105                 110

Thr Gln Cys Glu Phe Ser Lys Gln Glu Phe Met Asp Gly Met Thr Glu
        115                 120                 125

Leu Gly Cys Asp Ser Thr Glu Lys Leu Lys Ala Gln Ile Pro Lys Met
    130                 135                 140

Glu Gln Glu Leu Lys Glu Pro Gly Arg Phe Lys Asp Phe Tyr Gln Phe
145                 150                 155                 160

Thr Phe Asn Phe Ala Lys Asn Pro Gly Gln Lys Gly Leu Asp Leu Glu
                165                 170                 175

Met Ala Ile Ala Tyr Trp Asn Leu Val Leu Asn Gly Arg Phe Arg Leu
            180                 185                 190

Leu Asp Leu Trp Asn Lys Phe Leu Leu Glu His His Lys Arg Ser Ile
        195                 200                 205

Pro Lys Asp Thr Trp Asn Leu Leu Leu Asp Phe Ser Thr Met Ile Ala
    210                 215                 220

Asp Asp Met Ser Asn Tyr Asp Glu Glu Gly Ala Trp Pro Val Leu Ile
225                 230                 235                 240

Asp Asp Phe Val Glu Phe Ala Arg Pro Gln Ile Ala Gly Thr Lys Ser
                245                 250                 255

Thr Thr Val
```

<210> SEQ ID NO 5
<211> LENGTH: 64
<212> TYPE: DNA
<213> ORGANISM: Artificial sequence
<220> FEATURE:
<223> OTHER INFORMATION: DNA nucleotide sequence encoding the siRNA
      construct designed to target expression of the SCCRO gene

```
<400> SEQUENCE: 5
gatccccgtt cagagcagca acacagttca agagactgtg ttgctgctct gaacttttg    60 gaaa                                                                64

<210> SEQ ID NO 6
<211> LENGTH: 60
<212> TYPE: DNA
<213> ORGANISM: Artificial sequence
<220> FEATURE:
<223> OTHER INFORMATION: Nucleotide sequence encoding control siRNA

<400> SEQUENCE: 6
gatcccccgt ctacctacac tccctcttca agagagaggg agtgtaggta gacgttttta   60
```

METHODS FOR TREATING CANCER USING HERPES SIMPLEX VIRUS EXPRESSING ANTISENSE TO THE SQUAMOUS CELL CARCINOMA RELATED ONCOGENE

CROSS-REFERENCE TO RELATED APPLICATIONS

This application is a continuation application of U.S. patent application Ser. No. 10/579,622 filed May 16, 2006, entitled, "Mutant viruses," which is a '371 national stage patent application of PCT/GB2004/004908 filed Nov. 17, 2004, entitled "Mutant Herpes Simplex Virus and Use Thereof in the Treatment of Squamous Cell Cancer," which claims priority to United Kingdom Patent Application No. GB 0326798.6 filed Nov. 17, 2003, and further claims priority to U.S. Provisional Patent Application No. 60/541,308, filed Feb. 3, 2004 and entitled "Methods for Generating Mutant Virus," each of which is incorporated herein in its entirety by reference.

FIELD OF THE INVENTION

The present invention relates to materials and methods relating to the squamous cell carcinoma related oncogene (SCCRO) and to mutant herpes simplex viruses.

BACKGROUND TO THE INVENTION

The herpes simplex virus (HSV) genome comprises two covalently linked segments, designated long (L) and short (S). Each segment contains a unique sequence flanked by a pair of inverted terminal repeat sequences. The long repeat (RL or $R_L$) and the short repeat (RS or $R_S$) are distinct.

The HSV ICP34.5 (also γ34.5) gene, which has been extensively studied[1, 6, 7, 8], has been sequenced in HSV-1 strains F[9] and syn17+[3] and in HSV-2 strain HG52[4]. One copy of the ICP34.5 gene is located within each of the RL repeat regions. Mutants inactivating both copies of the ICP34.5 gene (i.e. null mutants), e.g. HSV-1 strain 17 mutant 1716[2] (HSV1716) or the mutants R3616 or R4009 in strain F[5], are known to lack neurovirulence, i.e. be avirulent, and have utility as both gene delivery vectors or in the treatment of tumours by oncolysis. HSV-1 strain 17 mutant 1716 has a 759 bp deletion in each copy of the ICP34.5 gene located within the BamHI s restriction fragment of each RL repeat.

ICP34.5 null mutants such as 1716 are, in effect, first-generation oncolytic viruses. Most tumours exhibit individual characteristics and the ability of a broad spectrum first generation oncolytic virus to replicate in or provide an effective treatment for all tumour types is not guaranteed.

HSV 1716 is described in EP 0571410 and WO 92/13943 and has been deposited on 28 Jan. 1992 at the European Collection of Animal Cell Cultures, Vaccine Research and Production Laboratories, Public Health Laboratory Services, Porton Down, Salisbury, Wiltshire, SP4 0JG, United Kingdom under accession number V92012803 in accordance with the provisions of the Budapest Treaty on the International Recognition of the Deposit of Microorganisms for the Purposes of Patent Procedure (herein referred to as the 'Budapest Treaty').

Squamous cell carcinoma of the head and neck afflicts an estimated 125,000 patients annually in Europe, North America and the Far East. Primary therapy for localized disease is surgery and adjuvant radiotherapy. Tumours recur in approximately one-third of patients. Once the cancer has recurred and/or metastasized, the patient is considered incurable. Combination chemotherapy induces responses in 30-50% of patients but there is no clear impact on survival. There remains an urgent need for more effective therapies[12, 13].

There has been much interest in the use of novel therapies in this disease with particular focus on oncolytic viruses by direct intratumoural injection. The use of oncolytic viruses to selectively kill tumours while leaving normal cells unaffected is a very attractive concept as it has the potential to limit the toxicity which occurs with conventional modalities. Recent research has been carried out using intratumoural injections of a selectively replicating adenovirus (Onyx-015) for the local control of recurrent disease. Phase I/II studies involving virus alone and in combination with chemotherapy have produced encouraging results[14, 15, 16].

Selectively replicating Herpes simplex viruses HSV may have better efficacy due to its more potent replication and oncolytic potential. HSV1716[17] is a deletion mutant of herpes simplex virus which fails to synthesise the virulence protein ICP34.5. It has been shown that HSV1716 replicates in actively dividing cells but not in resting or terminally differentiated cells[18, 19]. In vivo, HSV1716 administration has been carried out in mouse models of a range of cancers including melanoma, teratocarcinoma, glioma, medulloblastoma and mesothelioma. Animals showed improved survival and tumour regression following administration of HSV1716[20, 21, 22, 23, 24, 25] with no evidence of replication in normal tissue and no toxicity. HSV1716 has been used in Phase 1 trials in patients with glioblastoma multiform (GBM)[26], melanoma and head and neck cancer. No toxicity has been experienced and patients who were seropositive pre HSV1716 seroconverted and evidence of virus replication contained within tumours has been obtained.

It has been shown that the novel oncogene SCCRO (Squamous cell carcinoma related oncogene (also called Oncoseq and sometimes called SCRO)) is amplified in 30% of mucosal squamous cell cancers and that overexpression is associated with poor prognosis in head and neck cancer patients.

The Oncoseq nucleic acid sequence was described in U.S. Ser. No. 10/361,725 having publication number US 2004/0009541, published on 15 Jan. 2004. This document is incorporated herein in its entirety by reference. A polynucleotide sequence including an open reading frame of 780 nucleotides for Oncoseq and the amino acid sequence of the 259-residue polypeptide encoded thereby was reported.

US 2004/0009541 describes Oncoseq alleles to be oncogenes identified in primary squamous cell carcinoma tissues as being colocalised with the highest gene duplication peak within the 3q26.3 locus using a positional cloning approach with Oncoseq being highly duplicated in those carcinomas. Overexpression of Oncoseq is described to be correlated with gene duplication, aggressive clinical behaviour and malignant transformation in vitro, making it a strong candidate as the target for 3q amplification. The gene is described to be highly oncogenic and to have a basic region-helix-loop-helix-leucine zipper motif, suggesting it may function as a transcription factor.

RNAi

RNAi utilises small double-stranded RNA molecules (dsRNA) to target messenger RNA (mRNA), the precursor molecule that cells use to translate the genetic code into functional proteins. During the natural process of RNAi, dsRNA is processed into short-interfering RNA (siRNA) duplexes of 21 nucleotides in length, and it is these molecules which recognise and target homologous (endogenous) mRNA sequences for enzymatic degradation (by complementary base-pair binding), resulting in gene silencing.

The advantages of RNAi over other gene-targeting strategies such as anti-sense oligonucleotides include its relative specificity, its enhanced efficacy (only nanomolar quantities of siRNA are required for efficient gene-silencing), and the fact that siRNA treatment feeds into a natural RNAi pathway that is inherent to all cells.

The success of gene-silencing by siRNA can be highly variable depending on the gene target and cell type being targeted.

SUMMARY OF THE INVENTION

The inventors have used plasmid RL1.dIRES-GFP to generate a shuttle vector, designated RL1.dCMV-asSCCRO-GFP, containing the human antisense squamous cell carcinoma related oncogene (SCCRO) arranged in an orientation downstream of a CMV IE promoter to produce antisense RNA transcripts for use in antisense therapeutic methods.

Using this shuttle vector the inventors have provided a novel second generation mutant HSV, designated HSV1716/CMV-asSCCRO/GFP (also called HSV1716asSCCRO). The genome of this mutant HSV comprises the nucleic acid encoding heterologous (i.e. non-HSV originating) antisense SCCRO inserted at one or each ICP34.5 locus, disrupting the ICP34.5 protein coding sequence such that the ICP34.5 gene is non-functional and cannot express a functional ICP34.5 gene product. The generated HSV is capable of expressing an antisense RNA transcript under control of the CMV IE promoter which is capable of inhibiting the action of the SCCRO gene by binding to sense SCCRO nucleotide sequences, e.g. SCCRO mRNA or genomic SCCRO. This virus retains the oncolytic activity of HSV-1 strain 17 mutant 1716 and can be used in targeted antisense nucleotide delivery strategies and therapeutic methods.

In an alternative arrangement, instead of integrating a nucleic acid encoding an antisense, the inventors have integrated an siRNA in the genome of a herpes simplex virus. This siRNA is preferably heterologous to the herpes simplex virus and may be expressed from the herpes simplex virus genome. In one preferred embodiment the integrated nucleic acid encodes an siRNA capable of targeting and repressing or inhibiting expression of the functional SCCRO gene product. When expressed, the siRNA operates to silence, wholly or in part, expression of the functional SCCRO gene product.

The heterologous asSCCRO expressed by an herpes simplex virus according to the present invention may be useful in RNA based antisense therapeutic techniques for repression or silencing of the SCCRO gene product or of it's expressed function.

The siRNA expressed by an herpes simplex virus according to the present invention may be useful in siRNA based therapeutic techniques for tissue specific repression or silencing of the SCCRO gene product or of it's expressed function.

At its most general the present invention relates to (i) materials and methods relating to the squamous cell carcinoma related oncogene; and (ii) mutant herpes simplex viruses.

In one embodiment of the present invention, there is provided an attenuated replication competent HSV expressing antisense SCCRO, namely, HSV1716asSCCRO, which may be used in the treatment of squamous cell cancer, particularly head and neck squamous cell cancer.

Accordingly the present invention further provides a pharmaceutical composition comprising HSV1716asSCCRO and the use of such virus and/or composition in the treatment of cancer.

According to one aspect of the present invention there is provided an herpes simplex virus wherein the herpes simplex virus genome comprises nucleic acid encoding an antisense to the squamous cell carcinoma related oncogene (asSCCRO).

Said nucleic acid may encode an antisense to a mammalian squamous cell carcinoma related oncogene, more preferably an antisense to a human squamous cell carcinoma related oncogene.

In one arrangement said nucleic acid may encode a nucleotide sequence complementary to:
  (i) the polynucleotide sequence of SEQ ID Nos. 1 or 3 or its complement;
  (ii) the mRNA transcript of SEQ ID Nos. 1 or 3; or
  (iii) to a fragment of said polynucleotide sequence, complement or mRNA transcript.

In another arrangement said nucleic acid may encode a nucleotide sequence having at least 60% sequence identity to the nucleotide sequence complementary to:
  (i) the polynucleotide sequence of SEQ ID Nos. 1 or 3 or its complement;
  (ii) the mRNA transcript of SEQ ID Nos. 1 or 3; or
  (iii) to a fragment of said polynucleotide sequence or mRNA transcript.

More preferably said degree of sequence identity may be at least 70%, 80%, 90%, 95%, 96%, 97%, 98% or 99%. The fragment referred to at (iii) may comprise at least 20 nucleotides and may be limited to no more than 900 nucleotides. Identity of sequences is determined across the entire length of a given nucleotide sequence. Where sequences are of different length, sequence identity of the shorter sequence is determined over the entire length of the longer sequence.

In another arrangement said nucleic acid may be selected as one that hybridises to:
  (i) the polynucleotide sequence of SEQ ID Nos. 1 or 3 or its complement;
  (ii) the mRNA transcript of SEQ ID Nos. 1 or 3; or
  (iii) to a fragment of said polynucleotide sequence or mRNA transcript
under high or very high stringency conditions.

The genome of Herpes simplex viruses according to the present invention may further comprises a regulatory sequence operably linked to said nucleic acid encoding an antisense to the squamous cell carcinoma related oncogene, wherein said regulatory sequence has a role in controlling transcription of said siRNA.

In a further aspect of the present invention there is provided an herpes simplex virus wherein the herpes simplex virus genome comprises nucleic acid encoding a short interfering ribonucleic acid (siRNA) molecule that is capable of repressing or silencing expression of the squamous cell carcinoma related oncogene (SCCRO) nucleic acid or polypeptide.

Said siRNA may repress or silence expression of a mammalian SCCRO, more preferably of a human SCCRO.

Said nucleic acid encoding siRNA may comprise a nucleic acid of between 10 and 50 nucleotides in length and may have the sequence of SEQ ID No.5 or the complement thereof.

In another arrangement said nucleic acid encoding siRNA may comprise a nucleic acid of between 10 and 50 nucleotides in length and may have at least 70%, 80%, 90%, 95%, 96%, 97%, 98% or 99% identity to SEQ ID No.5 or the complement thereof. Identity of sequences is determined across the entire length of a given nucleotide sequence. Where sequences are of different length, sequence identity of the shorter sequence is determined over the entire length of the longer sequence.

In another arrangement said nucleic acid encoding siRNA may be selected as one that hybridises to the nucleic acid of SEQ ID No. 5 or its complement under high or very high stringency conditions.

The genome of said herpes simplex virus may further comprise a regulatory sequence operably linked to said siRNA, wherein said regulatory sequence has a role in controlling transcription of said siRNA.

The nucleic acid encoding asSCCRO or said siRNA may be located in at least one RL1 locus of the herpes simplex virus genome. Suitably it may be located in, or overlap, at least one of the ICP34.5 protein coding sequences of the herpes simplex virus genome. The nucleic acid may be located in both (usually this is all) copies of the RL1 locus or ICP34.5 protein coding sequence.

The herpes simplex virus is preferably a mutant and may be a mutant of HSV-1 or HSV-2, more preferably of one of HSV-1 strains 17, F or HSV-2 strain HG52. The herpes simplex virus may be a further mutant of HSV-1 strain 17 mutant 1716.

In certain arrangements the herpes simplex virus may be a gene specific null mutant, such as an ICP34.5 null mutant.

In other arrangements the herpes simplex virus may lack at least one expressible ICP34.5 gene.

In yet another arrangement the herpes simplex virus may lack only one expressible ICP34.5 gene.

In yet another arrangement the herpes simplex virus may be non-neurovirulent.

In herpes simplex viruses of the present invention the nucleic acid encoding the asSCCRO or said siRNA may form part of a nucleic acid cassette permanently integrated in the herpes simplex virus genome, said cassette comprising nucleic acid encoding:
  (a) said asSCCRO or said siRNA; and nucleic acid encoding;
  (b) a ribosome binding site or a first regulatory nucleotide sequence; and
  (c) a marker,
wherein the nucleic acid encoding said asSCCRO or siRNA is arranged upstream (5') of the ribosome binding site or first regulatory nucleotide sequence and the ribosome binding site or first regulatory nucleotide sequence is arranged upstream (5') of the marker. Said first regulatory sequence may have a role in controlling transcription of said marker.

A second regulatory nucleotide sequence may be located upstream (5') of the nucleic acid encoding asSCCRO or said siRNA, wherein the regulatory nucleotide sequence has a role in controlling and regulating transcription of the nucleic acid encoding the asSCCRO or siRNA and hence expression of the resulting transcript. The regulatory sequences may comprise selected promoter or enhancer elements known to the person skilled in the art, e.g. the CytoMegaloVirus (CMV) or phosphoglycerokinase (PGK) promoters.

The components of the cassette are preferably arranged in a predetermined order.

In one preferred arrangement, the nucleic acid encoding the asSCCRO is arranged upstream (i.e. 5') of the ribosome binding site and the ribosome binding site is arranged upstream (i.e. 5') of the marker. During transcription a single transcript may be produced from the cassette comprising a first cistron comprising the asSCCRO and a second cistron encoding the marker wherein the ribosome binding site is located between the cistrons.

A transcription product of this cassette may be a bi- or poly-cistronic transcript comprising a first cistron encoded by the nucleic acid encoding the asSCCRO and a second cistron encoding the marker nucleic acid wherein the ribosome binding site is located between said first and second cistrons.

In another preferred arrangement, the nucleic acid encoding the siRNA is arranged upstream (i.e. 5') of a first regulatory nucleotide sequence and the first regulatory nucleotide sequence is arranged upstream (i.e. 5') of the marker.

The cassette may disrupt a protein coding sequence of the herpes simplex virus genome resulting in inactivation of the respective gene product.

Nucleic acid encoding a selected antisense DNA, that is DNA corresponding to a gene component (e.g. regulatory sequence, 5' UTR, 3'UTR or protein coding sequence) or fragment of a gene component, is inserted in the cassette in an orientation such that upon transcription an antisense RNA is obtained. Thus the expressed product of the cassette may ultimately be an antisense nucleic acid, preferably RNA.

One suitable ribosome binding site comprises a ribosome entry site permitting entry of a ribosome to the transcribed mRNA encoded by the nucleic acid of the cassette such that the ribosome binds to the translation start signal. Preferably, the ribosome entry site is an internal ribosome entry site (IRES), more preferably an encephalomyocarditis virus IRES, permitting cap-independent initiation of translation. The IRES thus enables translation of a coding sequence located internally of a bi- or poly-cistronic mRNA, i.e. of a cistron located downstream of an adjacent cistron on a single transcript.

Preferably the marker is a defined nucleotide sequence coding for a polypeptide which can be expressed in a cell line (e.g. BHK cells) infected with mutant herpes simplex virus into which the cassette has been recombined. The function of the marker is to enable identification of virus plaques containing mutant virus transformed with the cassette.

The marker is preferably a detectable marker, more preferably an expressible marker polypeptide or protein comprising at least the coding sequence for the selected polypeptide or protein. The nucleic acid encoding the marker may further comprise regulatory sequence upstream and/or downstream of the coding sequence having a role in control of transcription of the marker mRNA. Preferred markers include the Green Fluorescent Protein (GFP) protein coding sequence or gene, preferably the enhanced Green Fluorescent Protein (EGFP) protein coding sequence or gene.

In other arrangements the marker may comprise a defined nucleotide sequence which can be detected by hybridisation under high stringency conditions with a corresponding labelled nucleic acid probe, e.g. using a fluorescent- or radio-label.

The cassette may also comprise nucleic acid encoding a polyadenylation ("polyA") sequence, which sequence is preferably located downstream (3') of the nucleic acid encoding the marker. One preferred polyA sequence is the Simian Virus 40 (SV40) polyadenylation sequence. The preferred location of the polyA sequence within the cassette is immediately downstream (i.e. 3') of the marker.

By antisense nucleic acid is meant a nucleic acid:
  (i) having substantial sequence identity to the nucleic acid formed by the sequence of complementary bases to the single strand of a target nucleic acid; and/or
  (ii) a nucleic acid which hybridises to the target nucleic acid under intermediate, high or very high stringency conditions.

In accordance with aspects of the present invention, the target nucleic acid may be an SCCRO polynucleotide sequence (e.g. gene sequence), the polynucleotide coding sequence for the SCCRO polypeptide or protein, or a part/fragment of the gene or polypeptide coding sequence. Thus, the antisense nucleic acid may be useful in binding the target nucleic acid (e.g. the SCCRO genomic coding sequence or mRNA transcript) and may be used as an inhibitor to prevent or disrupt the normal expression, activity, folding or binding of the target nucleic acid. The substantial sequence identity is preferably at least 50% sequence identity, more preferably one of at least 60, 70, 75, 80, 85, 90, 92, 94, 95, 96, 97, 98, 99 or 100% identity. Identity of sequences is determined across the entire length of a given nucleotide sequence. Where sequences are of different length, sequence identity of the shorter sequence is determined over the entire length of the longer sequence.

The antisense nucleic acid may comprise all or a fragment of the antisense to the squamous cell carcinoma related onco-gene (asSCCRO), preferably it is an antisense to the human SCCRO.

The nucleic acid encoding the asSCCRO which may form part of the inserted cassette may encode a full length transcript of the antisense nucleotide sequence to the SCCRO. That full length antisense transcript may be a sequence complementary to one of the polynucleotide sequences of SEQ ID No.1 or SEQ ID No.3 or their complementary sequences. Alternatively, the nucleic acid may encode one or more fragments of the full length antisense transcript.

A fragment may comprise a nucleotide sequence encoding at least 10% of the corresponding full length sequence, more preferably the fragment comprises at least 20, 30, 40, 50, 60, 70, 80, 85, 90, 95, 96, 97, 98 or 99% of the corresponding full length sequence. Preferably, the fragment comprises at least, i.e. has a minimum length of, 20 nucleotides, more preferably at least 30, 40, 50, 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000 nucleotides. The fragment may have a maximum length, i.e. be no longer than, 20 nucleotides, more preferably no longer than 30, 40, 50, 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000. The fragment length may be anywhere between said minimum and maximum length.

In the case of an antisense to the SCCRO, a full length transcript comprises a minimum of the contiguous sequence of nucleotides forming an antisense strand to the corresponding complete nucleotide sequence encoding the full amino acid sequence of the SCCRO gene product or to is compliment. The complete nucleotide sequence of the SCCRO gene product may comprise the region of SEQ ID No.1 or SEQ ID No.3 respectively encoding the polypeptide of SEQ ID No. 2 or SEQ ID No.4.

Preferred antisense nucleic acids may single stranded and may be DNA or RNA.

Preferred siRNA may be single or double stranded and may comprise single stranded nucleic acids capable of forming duplex structures by stem-loop formation and self-binding of complementary nucleotides. Preferred siRNA may include RNA molecules having a sequence encoded by SEQ ID No. 5 or its complement and nucleic acids having a sequence identity of at least 60% to SEQ ID No. 5 or a complementary sequence thereof, and more preferably having at least 70, 80, 85, 90, 95% or 100% sequence identity. Identity of sequences is determined across the entire length of a given nucleotide sequence. Where sequences are of different length, sequence identity of the shorter sequence is determined over the entire length of the longer sequence.

Preferred siRNA or nucleic acid encoding preferred siRNA may comprise nucleotide sequences heterologous to the selected HSV strain being modified, i.e. the siRNA or nucleic acid sequence encoding the siRNA does not occur in or originate from the parental, unmodified wild-type, virus.

Furthermore Herpes simplex viruses according to aspects of the present invention may contain nucleic acid, encoding siRNA molecules, which hybridise with SEQ ID No 5 or its complement under very high, high or intermediate stringency conditions.

siRNA molecules encoded by nucleic acid molecules integrated in the genome of Herpes simplex viruses according to the present invention may be of any length, but preferred siRNA molecules are small and may comprise at least 10 nucleotides and no more than 50 nucleotides. Herpes simplex virus according to the present invention may encode an siRNA which is a fragment of the siRNA encoded by SEQ ID No.5. Particularly suitable siRNA will have a single strand length in the range 10 to 30 nucleotides and more suitably in the range 15 to 25 nucleotides. Selected siRNA molecules may be any of 15, 16, 17, 18, 19, 20, 21, 22, 23, 24 or 25 nucleotides in length. SiRNA molecules which fold to form their own duplex structures, e.g. by stem-loop formation will thus have an unfolded single strand length of about two times the number or range recited above and siRNA and nucleic acid encoding such siRNA may be particularly preferred.

Herpes simplex viruses according to aspects of the present invention may contain nucleic acid encoding siRNA molecules having one or more of these sequences.

Mutant herpes simplex viruses of the present invention may be generated by site directed insertion of a nucleic acid cassette into the viral genome, more preferably by homologous recombination. However, the viruses of the invention are not limited to Herpes simplex viruses obtained in this way.

In other aspects of the present invention herpes simplex viruses according to the present invention are provided for use in a method of medical treatment. Suitably they are provided for use in the treatment of disease. Preferably they are provided for use in the treatment of cancer. Suitably they may be provided for use in the oncolytic treatment of cancer/a tumour. The use of herpes simplex viruses according to the present invention in the manufacture of a medicament for the treatment of cancer is also provided.

In another aspect of the present invention medicaments comprising herpes simplex virus mutants according to the present invention for use in oncotherapy and methods of treating tumours comprising administering to a patient in need of treatment an effective amount of a mutant HSV or a medicament comprising or derived from such HSV are also provided. Methods of lysing or killing tumour cells in vitro or in vivo comprising the step of administering to a patient in need of treatment an amount of an Herpes simplex virus according to the present invention are also provided.

A medicament, pharmaceutical composition or vaccine comprising an Herpes simplex virus according to the present invention is also provided. The medicament, pharmaceutical composition or vaccine may further comprise a pharmaceutically acceptable carrier, adjuvant or diluent.

The present invention may also include the following aspects which may be provided in combination with any of the other aspects and features described.

In another aspect of the present invention there is provided an herpes simplex virus, wherein the genome of said virus comprises a nucleic acid sequence encoding an antisense to the squamous cell carcinoma related oncogene (asSCCRO) in at least one of the long repeat regions ($R_L$).

In another aspect of the present invention there is provided an herpes simplex virus, wherein the genome of said virus comprises a nucleic acid sequence encoding an antisense to the squamous cell carcinoma related oncogene (asSCCRO) and wherein the herpes simplex virus is non-neurovirulent.

In another aspect of the present invention there is provided an herpes simplex virus for use in the treatment of a tumour, wherein the genome of said virus comprises a nucleic acid sequence encoding an antisense to the squamous cell carcinoma related oncogene (asSCCRO) in at least one of the long repeat regions ($R_L$).

In another aspect of the present invention there is provided an herpes simplex virus for use in the treatment of a tumour, wherein the genome of said virus comprises a nucleic acid sequence encoding an antisense to the squamous cell carcinoma related oncogene (asSCCRO) and wherein the herpes simplex virus is non-neurovirulent.

In another aspect of the present invention the use of an herpes simplex virus, wherein the genome of said virus comprises a nucleic acid sequence encoding an antisense to the squamous cell carcinoma related oncogene (asSCCRO) in at least one of the long repeat regions ($R_L$), in the manufacture of a medicament for the treatment of cancer is provided.

In another aspect of the present invention the use of an herpes simplex virus, wherein the genome of said virus comprises a nucleic acid sequence encoding an antisense to the squamous cell carcinoma related oncogene (asSCCRO) and wherein the herpes simplex virus is non-neurovirulent, in the manufacture of a medicament for the treatment of cancer is provided.

In another aspect of the present invention there is provided a method for the treatment of a tumour comprising the step of administering to a patient in need of treatment an effective amount of an herpes simplex virus, wherein the genome of said virus comprises a nucleic acid sequence encoding an antisense to the squamous cell carcinoma related oncogene (asSCCRO) in at least one of the long repeat regions ($R_L$).

In another aspect of the present invention there is provided a method for the treatment of a tumour comprising the step of administering to a patient in need of treatment an effective amount of an herpes simplex virus, wherein the genome of said virus comprises a nucleic acid sequence encoding an antisense to the squamous cell carcinoma related oncogene (asSCCRO) and wherein the herpes simplex virus is non-neurovirulent.

Suitably, in the methods of treatment of a tumour the herpes simplex virus is capable of killing tumour cells.

In another aspect of the present invention there is provided a method of expressing in vitro or in vivo an antisense to the squamous cell carcinoma related oncogene (asSCCRO), said method comprising the step of infecting at least one cell or tissue of interest with a herpes simplex virus, wherein the genome of said virus comprises a nucleic acid sequence encoding asSCCRO in at least one of the long repeat regions ($R_L$), said asSCCRO operably linked to a transcription regulatory sequence.

In another aspect of the present invention there is provided a method of expressing in vitro or in vivo an antisense to the squamous cell carcinoma related oncogene (asSCCRO), said method comprising the step of infecting at least one cell or tissue of interest with a non-neurovirulent herpes simplex virus, wherein the genome of said virus comprises a nucleic acid sequence encoding asSCCRO, said asSCCRO operably linked to a transcription regulatory sequence.

In another aspect of the present invention there is provided an herpes simplex virus, wherein the genome of said virus comprises a nucleic acid sequence encoding a short interfering ribonucleic acid (siRNA) molecule that is capable of repressing or silencing expression of squamous cell carcinoma related oncogene (SCCRO) nucleic acid or polypeptide in at least one of the long repeat regions ($R_L$).

In another aspect of the present invention there is provided an herpes simplex virus, wherein the genome of said virus comprises a nucleic acid sequence encoding a short interfering ribonucleic acid (siRNA) molecule that is capable of repressing or silencing expression of squamous cell carcinoma related oncogene (SCCRO) nucleic acid or polypeptide and wherein the herpes simplex virus is non-neurovirulent.

In another aspect of the present invention there is provided an herpes simplex virus for use in the treatment of a tumour, wherein the genome of said virus comprises a nucleic acid sequence encoding a short interfering ribonucleic acid (siRNA) molecule that is capable of repressing or silencing expression of squamous cell carcinoma related oncogene (SCCRO) nucleic acid or polypeptide in at least one of the long repeat regions ($R_L$).

In another aspect of the present invention there is provided an herpes simplex virus for use in the treatment of a tumour, wherein the genome of said virus comprises a nucleic acid sequence encoding a short interfering ribonucleic acid (siRNA) molecule that is capable of repressing or silencing expression of squamous cell carcinoma related oncogene (SCCRO) nucleic acid or polypeptide and wherein the herpes simplex virus is non-neurovirulent.

In another aspect of the present invention the use of an herpes simplex virus, wherein the genome of said virus comprises a nucleic acid sequence encoding a short interfering ribonucleic acid (siRNA) molecule that is capable of repressing or silencing expression of squamous cell carcinoma related oncogene (SCCRO) nucleic acid or polypeptide in at least one of the long repeat regions ($R_L$), in the manufacture of a medicament for the treatment of cancer is provided.

In another aspect of the present invention the use of an herpes simplex virus, wherein the genome of said virus comprises a nucleic acid sequence encoding a short interfering ribonucleic acid (siRNA) molecule that is capable of repressing or silencing expression of squamous cell carcinoma related oncogene (SCCRO) nucleic acid or polypeptide and wherein the herpes simplex virus is non-neurovirulent, in the manufacture of a medicament for the treatment of cancer is provided.

In another aspect of the present invention there is provided a method for the treatment of a tumour comprising the step of administering to a patient in need of treatment an effective amount of an herpes simplex virus, wherein the genome of said virus comprises, in at least one of the long repeat regions ($R_L$), a nucleic acid sequence encoding a short interfering ribonucleic acid (siRNA) molecule that is capable of repressing or silencing expression of squamous cell carcinoma related oncogene (SCCRO) nucleic acid or polypeptide.

In another aspect of the present invention there is provided a method for the treatment of a tumour comprising the step of administering to a patient in need of treatment an effective amount of an herpes simplex virus, wherein the genome of said virus comprises a nucleic acid sequence encoding a short interfering ribonucleic acid (siRNA) molecule that is capable of repressing or silencing expression of squamous cell carcinoma related oncogene (SCCRO) nucleic acid or polypeptide and wherein the herpes simplex virus is non-neurovirulent.

Suitably, in the methods of treatment of a tumour the herpes simplex virus is capable of killing tumour cells.

In another aspect of the present invention there is provided a method of expressing in vitro or in vivo a short interfering ribonucleic acid (siRNA) molecule that is capable of repressing or silencing expression of squamous cell carcinoma related oncogene (SCCRO) nucleic acid or polypeptide, said method comprising the step of infecting at least one cell or tissue of interest with a herpes simplex virus, wherein the genome of said virus comprises a nucleic acid sequence encoding said siRNA in at least one of the long repeat regions ($R_L$), wherein said nucleic acid sequence encoding said siRNA is operably linked to a transcription regulatory sequence.

In another aspect of the present invention there is provided a method of expressing in vitro or in vivo a short interfering ribonucleic acid (siRNA) molecule that is capable of repressing or silencing expression of squamous cell carcinoma related oncogene (SCCRO) nucleic acid or polypeptide, said method comprising the step of infecting at least one cell or tissue of interest with a non-neurovirulent herpes simplex virus, wherein the genome of said virus comprises a nucleic acid sequence encoding said siRNA, wherein said nucleic acid sequence encoding said siRNA is operably linked to a transcription regulatory sequence.

siRNA according to the invention preferably repress the function of the squamous cell carcinoma related oncogene (SCCRO) protein.

In another aspect of the present invention a method is provided for repressing the cellular expression of the squamous cell carcinoma related oncogene (SCCRO) in vitro comprising the step of: in vitro, contacting a cell with an herpes simplex virus of the present invention or pharmaceutical composition containing such virus.

In one preferred aspect of the invention the herpes simplex virus is HSV1716/CMV-asSCCRO/GFP, deposited as 'HSV1716asSCCRO', in the name of Crusade Laboratories Limited having an address at Department of Neurology Southern General Hospital 1345 Govan Road Govan Glasgow G51 5TF Scotland on 19 May 2004 at the European Collection of Cell Cultures (ECACC), Health Protection Agency, Porton Down, Salisbury, Wiltshire, SP4 0JG, United Kingdom under accession number 04051901 in accordance with the provisions of the Budapest Treaty on the International Recognition of the Deposit of Microorganisms for the Purposes of Patent Procedure (herein referred to as the 'Budapest Treaty').

In yet another aspect of the present invention a cell, in vitro, in which expression of the squamous cell carcinoma related oncogene (SCCRO) protein or nucleic acid is repressed or silenced is provided. The cell may be a mammalian cell, preferably a human cell.

Suitably, the administration of said herpes simplex virus may comprise parenteral administration. Preferably administration of the herpes simplex virus is by injection, more preferably injection to the tumour which is to be treated. Alternatively injections may be intravenous.

In a further aspect of the present invention in vitro or in vivo methods are provided for delivery of nucleic acid encoding asSCCRO or siRNA to at least one cell or to a tissue of interest said method comprising the step of infecting said cell(s) or tissue with a herpes simplex virus according to the invention.

In another aspect of the present invention a method of making or producing a modified herpes simplex virus of the invention is provided comprising the step of introducing a nucleic acid sequence encoding asSCCRO or siRNA at a selected or predetermined insertion site in the genome of a selected herpes simplex virus.

As described, the nucleic acid sequence encoding the asSCCRO or siRNA may form part of a nucleic acid cassette which is inserted in the genome of a selected herpes simplex virus by homologous recombination. Whether part of a cassette or not, the site of insertion may be in any genomic location selected. One preferred insertion site is in one or both of the long repeat regions ($R_L$), and one copy of the cassette is preferably inserted in each copy of the long repeat ($R_L$). More preferably the insertion site is in at least one (preferably both) RL1 locus and most preferably it is inserted in at least one (preferably both) of the ICP34.5 protein coding sequences of the HSV genomic DNA. It is preferred that the insertion occurs in identical or substantially similar positions in each of the two repeat regions, RL1 loci or ICP34.5 protein coding sequences.

Insertion may be such as to produce a modified virus which is a non-neurovirulent mutant capable of expressing the encoded asSCCRO or siRNA upon transfection into mammalian, more preferably human, cells in vivo and in vitro. The non-neurovirulent mutant may be an ICP34.5 null mutant.

The nucleic acid cassette may be of any size, e.g. up to 5, 10, 15, 20, 25, 30, 35, 40, 45 or 50 Kbp in length.

Preferably, the herpes simplex virus contains at least one copy of the nucleic acid encoding the asSCCRO or siRNA in each long repeat region ($R_L$), i.e. in the terminal and internal long repeat ($TR_L$ and $IR_L$) regions. In a preferred arrangement each exogenous sequence or cassette is located in an RL1 locus of the herpes simplex virus genome, more preferably in the DNA of the herpes simplex virus genome encoding the ICP34.5 gene or protein coding sequence. The herpes simplex virus thereby lacks neurovirulence.

The parent herpes simplex virus, from which a virus of the invention is derived may be of any kind, e.g. HSV-1 or HSV-2. In one preferred arrangement the herpes simplex virus is a variant of HSV-1 strain 17 and may be obtained by modification of the strain 17 genomic DNA. Suitable modifications include the insertion of the exogenous asSCCRO or siRNA nucleic acid sequences or exogenous/heterologous cassette comprising said sequence into the herpes simplex virus genomic DNA. The insertion may be performed by homologous recombination of the exogenous nucleic acid sequence into the genome of the selected herpes simplex virus.

Although the non-neurovirulent phenotype of the herpes simplex virus of the invention may be the result of insertion of the exogenous nucleic acid sequence in the RL1 locus, herpes simplex viruses according to the present invention may be obtained by utilising a non-neurovirulent parent strain, e.g. HSV1716 deposited under the Budapest Treaty at the European Collection of Animal Cell Cultures (ECACC), Health Protection Agency, Porton Down, Salisbury, Wiltshire, United Kingdom under accession number V92012803, and inserting the exogenous nucleic acid sequence at another location of the genome by standard genetic engineering techniques, e.g. homologous recombination. In this aspect the location of the herpes simplex virus genome selected for insertion of the asSCCRO or siRNA nucleic acid sequence or cassette containing said sequence may be a neutral location.

Herpes simplex viruses of the present invention may be variants of a known 'parent' strain from which the herpes simplex virus of the invention has been derived. A particularly preferred parent strain is HSV-1 strain 17. Other parent strains may include HSV-1 strain F or HSV-2 strain HG52. A variant comprises an HSV in which the genome substantially resembles that of the parent, contains the asSCCRO or siRNA encoding nucleic acid sequence or cassette containing said sequence and may contain a limited number of other modifications, e.g. one, two or three other specific mutations, which may be introduced to disable the pathogenic properties of the herpes simplex virus, for example a mutation in the ribonucleotide reductase (RR) gene, the 65K trans inducing factor (TIF) and/or a small number of mutations resulting from natural variation, which may be incorporated naturally during replication and selection in vitro or in vivo. Otherwise the genome of the variant will be that of the parent strain.

Herpes simplex viruses of the invention may be used in a method of medical treatment. This may involve treatment of diseases associated with or involving the proliferation of cells, or cancers or tumours of any kind. Treatment may involve the selective lysis of dividing cells. This may be oncolysis, i.e. lysis of tumour cells. Tumours to be treated may be of any kind, may comprise cancers, neoplasms or neoplastic tissue and may be in any animal or human patient.

Herpes simplex viruses of the invention may be used in 'gene delivery' methods in vitro or in vivo. Non-neurovirulent herpes simplex viruses of the invention are expression vectors and may be used to infect selected cells or tissues in order to express the asSCCRO or siRNA encoded by the herpes simplex virus genome.

In one arrangement, cells may be taken from a patient, a donor or from any other source, infected with a herpes simplex virus of the invention, optionally screened for expression and/or function of the encoded asSCCRO or siRNA, and optionally returned/introduced to a patient's body, e.g. by injection.

Delivery of herpes simplex viruses of the invention to the selected cells may be performed using naked virus or by encapsulation of the virus in a carrier, e.g. nanoparticles, liposomes or other vesicles.

In vitro cultured cells, preferably human or mammalian cells, transformed with viruses of the present invention and preferably cells expressing the asSCCRO or siRNA as well as methods of transforming such cells in vitro with said viruses form further aspects of the present invention.

Cancer/tumour types to be treated may include primary and/or secondary (metastatic) tumours. These may be carcinomas of the head and/or neck. They may be squamous cell carcinomas, which may be of mucosal origin and may show a predilection for duplication of the 3q locus. Preferred squamous cell carcinomas to be treated may be those of the head and/or neck. Squamous cell carcinomas to be treated may include those originating from the lung, head neck, esophagus and cervix.

Other tumour types which may be treated may be primary or secondary (metastatic) tumours. Tumours to be treated may be nervous or non-nervous system tumours. Nervous system tumours may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system tumours may originate in any other non-nervous tissue, examples include melanoma, mesothelioma, lymphoma, hepatoma, epidermoid carcinoma, prostate carcinoma, breast cancer cells, lung cancer cells or colon cancer cells. HSV mutants of the present invention may be used to treat metastatic tumours of the central or peripheral nervous system which originated in a non-nervous system tissue.

In this specification, a mutant herpes simplex virus is a non-wild type herpes simplex virus and may be a recombinant herpes simplex virus. Mutant herpes simplex viruses may comprise a genome containing modifications relative to the wild type. A modification may include at least one deletion, insertion, addition or substitution.

Medicaments and pharmaceutical compositions according to aspects of the present invention may be formulated for administration by a number of routes, including but not limited to, parenteral, intravenous, intramuscular, intratumoural, oral and nasal. The medicaments and compositions may be formulated in fluid or solid (e.g. tablet) form. Fluid formulations may be formulated for administration by injection to a selected region of the human or animal body.

In this specification, non-neurovirulence is defined by the ability to introduce a high titre of virus (approx $10^6$ plaque forming units (pfu)) to an animal or patient[22, 23] without causing a lethal encephalitis such that the $LD_{50}$ in animals, e.g. mice, or human patients is in the approximate range of $\geq 10^6$ pfu[21].

Where all copies of the ICP34.5 gene present in the herpes simplex virus genome (two copies are normally present) are disrupted such that the herpes simplex virus is incapable of producing a functional ICP34.5 gene product, the virus is considered to be an ICP34.5 null mutant.

A regulatory sequence (e.g. promoter) that is operably linked to a nucleotide sequence may be located adjacent to that sequence or in close proximity such that the regulatory sequence can effect and/or control expression of a product of the nucleotide sequence. The encoded product of the nucleotide sequence may therefore be expressible from that regulatory sequence.

SCCRO

The polynucleotide sequence of SEQ ID No.1, positions 43-918 and the polynucleotide of SEQ ID No.2 are disclosed in GenBank Accession No. AF456425 (GI:18700655) released to the public as of 19 Feb. 2002.

A second Oncoseq (Oncoseq2) polypeptide is encoded by the polynucleotide sequence of SEQ ID No.3, which together with the polypeptide thereby encoded (SEQ ID No.4) are disclosed in GenBank Accession No. AF456426 (GI: 18700657) released to the public as of 19 Feb. 2002.

The GenBank database may be accessed at obtainable at www.ncbi.nlm.nih.gov.

Therapeutic Strategies

The following therapeutic strategies are provided by way of example only. The invention is not limited to a theory of operation of a given antisense or siRNA.

Antisense

Herpes simplex viruses according to the present invention may express an antisense nucleic acid, e.g. single stranded RNA that targets and binds, by complementary sequence binding, to the target mRNA thereby blocking translation of that mRNA and expression of the gene product.

Expressed antisense nucleic acid may also be arranged to bind sense genomic nucleic acid and inhibit transcription of a target nucleotide sequence.

siRNA

Herpes simplex viruses according to the present invention may encode nucleic acid designed such that on transcription an RNA having internal complementary sequence is provided and which may bind to form a short hairpin siRNA duplex having a stem-loop structure. Preferably, the hairpin siRNA mediates specific repression and/or silencing of gene expression by RNA interference.

Alternatively, two siRNA molecules may be encoded which are designed to bind by complementary sequence binding and form a functionally active duplex molecule.

Repression and Silencing siRNA and antisense molecules provided under the invention are designed to repress or silence the expression of a target nucleic acid, peptide, polypeptide or protein or to repress a function of such nucleic acid, peptide, polypeptide or protein.

A repression of expression results in a decrease in the quantity or expressed function of the target. For example, in a given cell the repression of SCCRO by expression of an siRNA or antisense may result in a decrease in either the quantity of the SCCRO gene product or the expressed function of the SCCRO gene product relative to an untreated cell.

Repression of a function may involve the decrease in transcription of an mRNA, or translation of a peptide or polypeptide.

Repression may be partial. Preferred degrees of repression are at least 50%, more preferably one of at least 60, 70, 80, 85 or 90%. A level of repression between 90% and 100% is considered a 'silencing' of expression or function.

Hybridisation Stringency

In accordance with the present invention, nucleic acid sequences may be identified by using hybridization and washing conditions of appropriate stringency.

Complementary nucleic acid sequences will hybridise to one another through Watson-Crick binding interactions. Sequences which are not 100% complementary may also hybridise but the strength of the hybridisation usually decreases with the decrease in complementarity. The strength of hybridisation can therefore be used to distinguish the degree of complementarity of sequences capable of binding to each other.

The "stringency" of a hybridization reaction can be readily determined by a person skilled in the art.

The stringency of a given reaction may depend upon factors such as probe length, washing temperature, and salt concentration. Higher temperatures are generally required for proper annealing of long probes, while shorter probes may be annealed at lower temperatures. The higher the degree of desired complementarity between the probe and hybridisable sequence, the higher the relative temperature which can be used. As a result, it follows that higher relative temperatures would tend to make the reaction conditions more stringent, while lower temperatures less so.

For example, hybridizations may be performed, according to the method of Sambrook et al., ("Molecular Cloning, A Laboratory Manual, Cold Spring Harbor Laboratory Press, 1989) using a hybridization solution comprising: 5×SSC, 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules is to calculate the melting temperature $T_m$ (Sambrook et al., 1989):

$$T_m = 81.5°\text{ C.} + 16.6 \text{ Log [Na+]} + 0.41(\%G+C) - 0.63(\% \text{ formamide}) - 600/n$$

where n is the number of bases in the oligonucleotide.

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in sequence complementarity.

Accordingly, nucleotide sequences can be categorised by an ability to hybridise to a target sequence under different hybridisation and washing stringency conditions which can be selected by using the above equation. The $T_m$ may be used to provide an indicator of the strength of the hybridisation.

The concept of distinguishing sequences based on the stringency of the conditions is well understood by the person skilled in the art and may be readily applied.

Sequences exhibiting 95-100% sequence complementarity may be considered to hybridise under very high stringency conditions, sequences exhibiting 85-95% complementarity may be considered to hybridise under high stringency conditions, sequences exhibiting 70-85% complementarity may be considered to hybridise under intermediate stringency conditions, sequences exhibiting 60-70% complementarity may be considered to hybridise under low stringency conditions and sequences exhibiting 50-60%% complementarity may be considered to hybridise under very low stringency conditions.

The invention includes the combination of the aspects and preferred features described except where such a combination is clearly impermissible or expressly avoided.

Aspects and embodiments of the present invention will now be illustrated, by way of example, with reference to the accompanying figures. Further aspects and embodiments will be apparent to those skilled in the art. All documents mentioned in this text are incorporated herein by reference.

*Clones 5 and 8 contained the pCMV-NAT-IRES-GFP-PolyA insert as two fragments of the predicted size—4.8 Kbp and 9.2 Kbp—were generated from AflII digestion. Clones without inserts would not be digested with AflII as there is no AflII site in RL1.del. N.B. Inserts could have been cloned in two orientations, both of which were acceptable.

Figure 5:
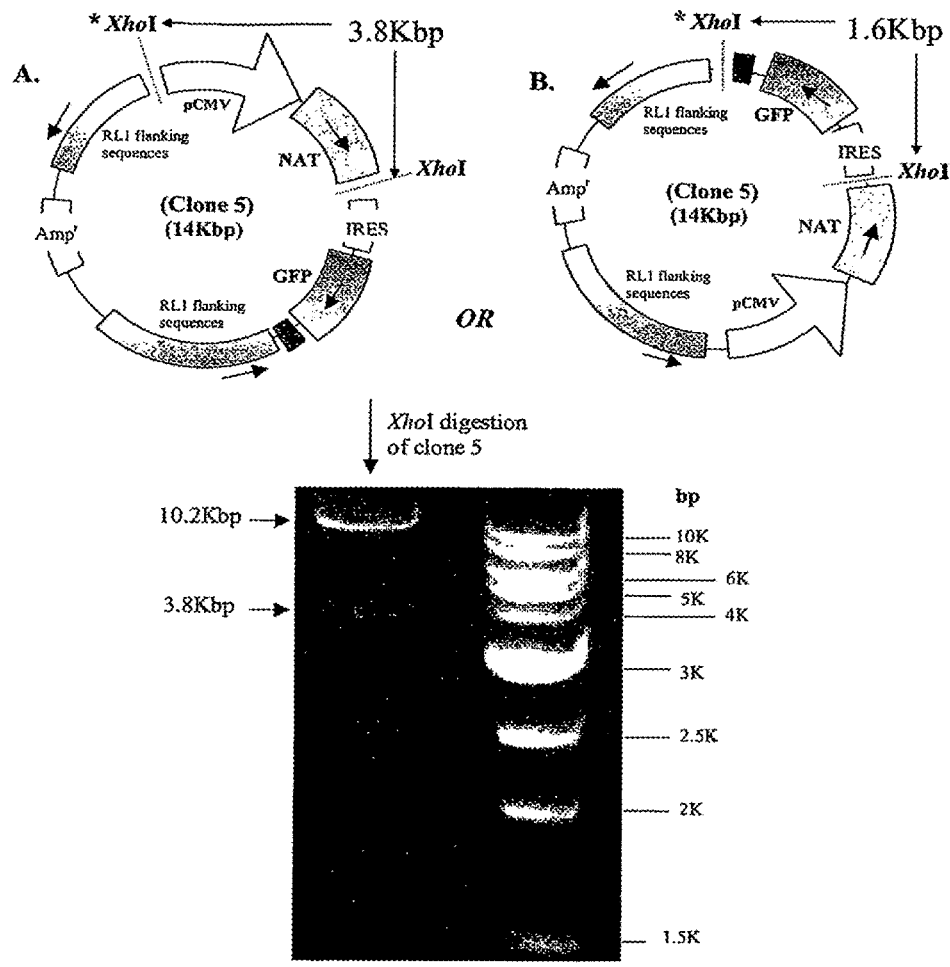

FIG. 5. Determination of the orientation of pCMV-NAT-IRES-GFP-PolyA in clone 5 (RL1.dCMV-NAT-GFPb). pCMV-NAT-IRES-GFP-PolyA (blunt ended) could have been cloned into the HpaI site of RL1.del in two orientations. To determine the orientation of the insert in clone 5, the plasmid was digested with XhoI and the digested DNA electrophoresed, beside a 1 Kbp DNA ladder (Promega), on a 1% agarose gel. If the insert had been cloned in the orientation shown in A, two fragments of 10.2 Kbp and 3.8 Kbp would be generated from XhoI digestion. If it had been cloned in the opposite orientation (B), two fragments of 12.4 Kbp and 1.6

Kbp would be generated. The presence of two fragments of 10.2 Kbp and 3.8 Kbp in the gel confirmed that the insert had been cloned in the orientation shown in A.

*This XhoI site was present in the initial cloning vector (RL1.del), upstream of the HpaI site into which pCMV-NAT-IRES-GFP-PolyA was cloned.

Figure 6:
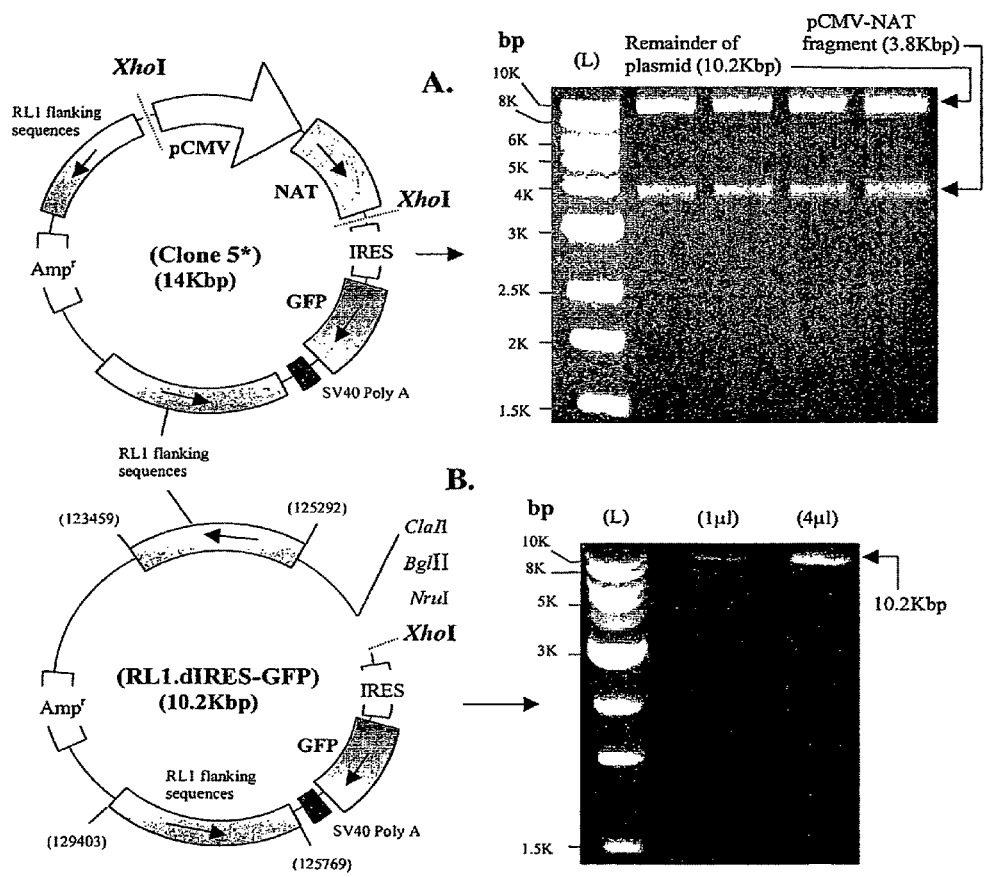

FIG. 6. Removal of pCMV-NAT from clone 5 (A) and large scale plasmid preparation of RL1.dIRES-GFP (B). Four samples of clone 5 were digested with XhoI and electrophoresed, beside a 1 Kbp DNA ladder (L) (Promega), on a 1% agarose gel (A). The larger fragment of DNA generated from this digestion (10.2 Kbp) was purified from the gel and ligated back together, at the XhoI sites, to form a single XhoI site in a new plasmid, designated RL1.dIRES-GFP. A large-scale plasmid preparation was grown up and the preparation checked by digesting with XhoI. 1 μl and 4 μl of the digested DNA was electrophoresed, beside a 1 Kbp DNA ladder (L) (Promega), on a 1% agarose gel (B). The DNA should produce a single fragment of 10.2 Kbp when digested with XhoI. The ClaI, BglII, NruI and XhoI sites of RL1.dIRES-GFP are all unique.

*Clone 5 is the RL1.del plasmid into which has been cloned the 5.4 Kbp pCMV-NAT-IRES-GFP-PolyA fragment from pNAT-IRES-GFP.

Figure 7:
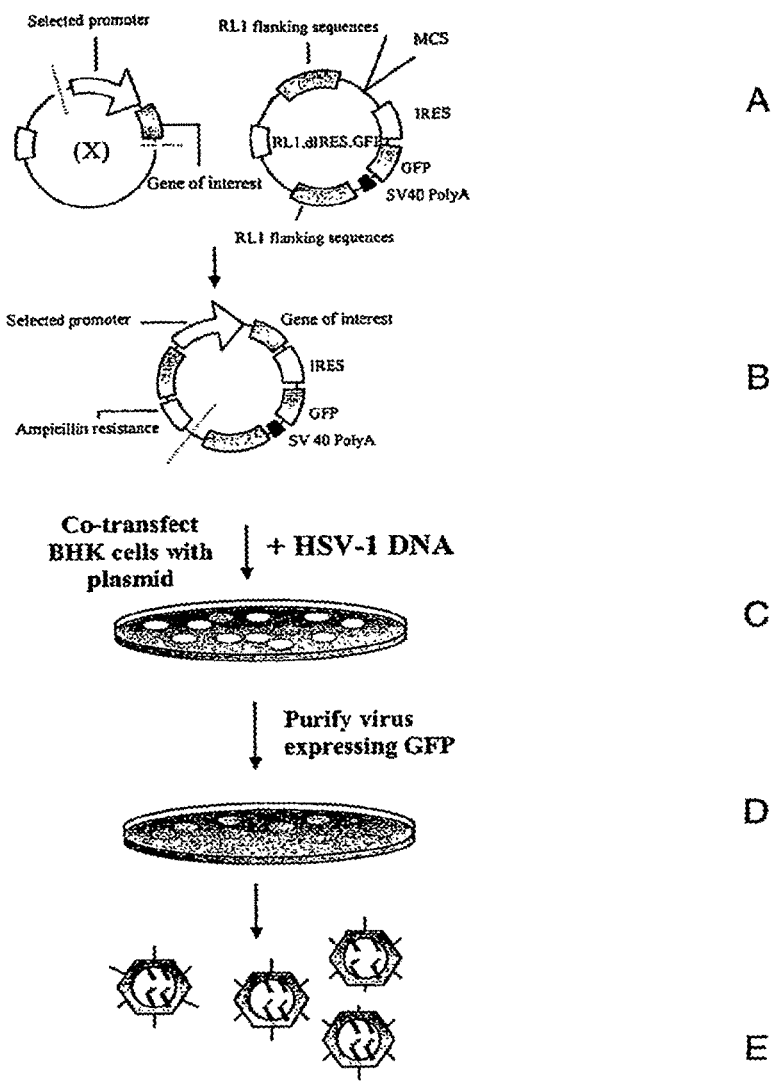

FIG. 7. Generation, detection and purification of ICP34.5 null HSV-1 expressing a gene product of interest.

Figure 8:
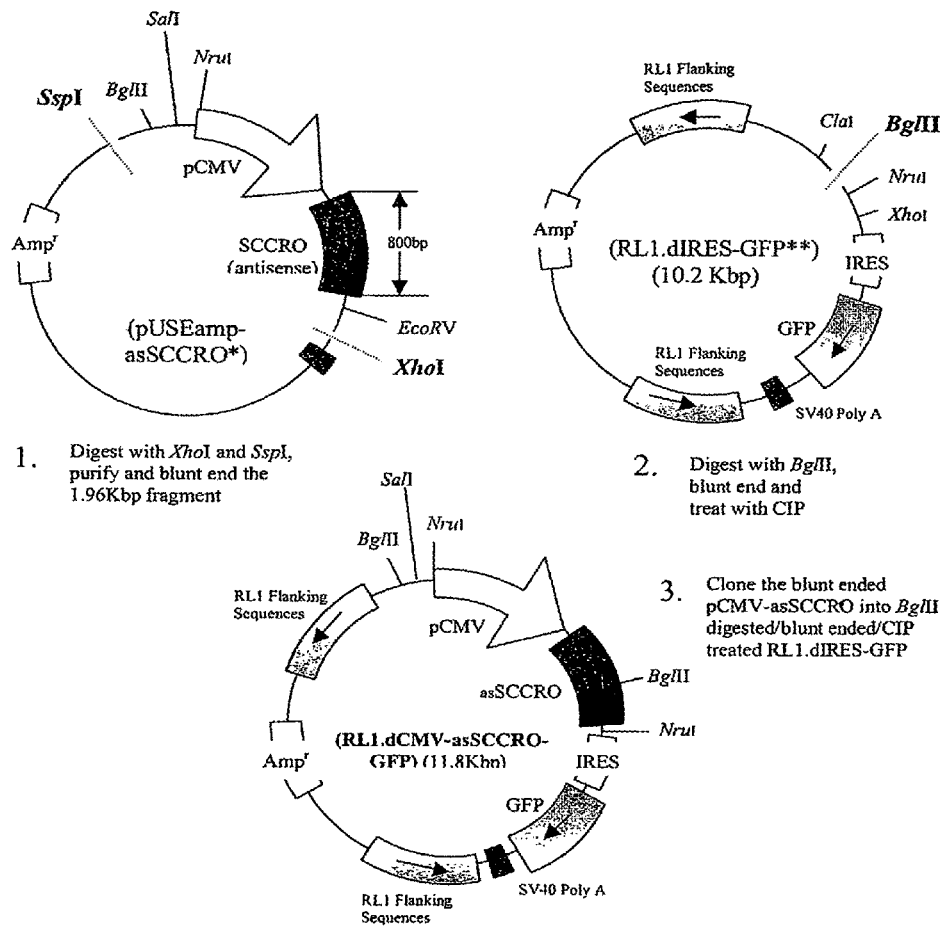

FIG. 8. Strategy used to clone pCMV-asSCCRO, from pUSEamp-asSCCRO, into RL1.dIRES-GFP. (1) Digest pUSEamp-asSCCRO with Ssp1 and XhoI and purify the 1.96 Kbp pCMV-asSCCRO fragment; (2) Digest RL1.dIRES-GFP with BglII, blunt end using Klenow polymerase and treat with Calf Intestinal Phosphatase (CIP). (3) Clone the blunt ended pCMV-asSCCRO fragment (1.96 Kbp) into BglII digested/blunt ended/CIP treated RL1.dIRES-GFP. (*pUSE-amp-asSCCRO was provided by Memorial Sloan-Kettering Cancer Centre, New York.)

Figure 9:
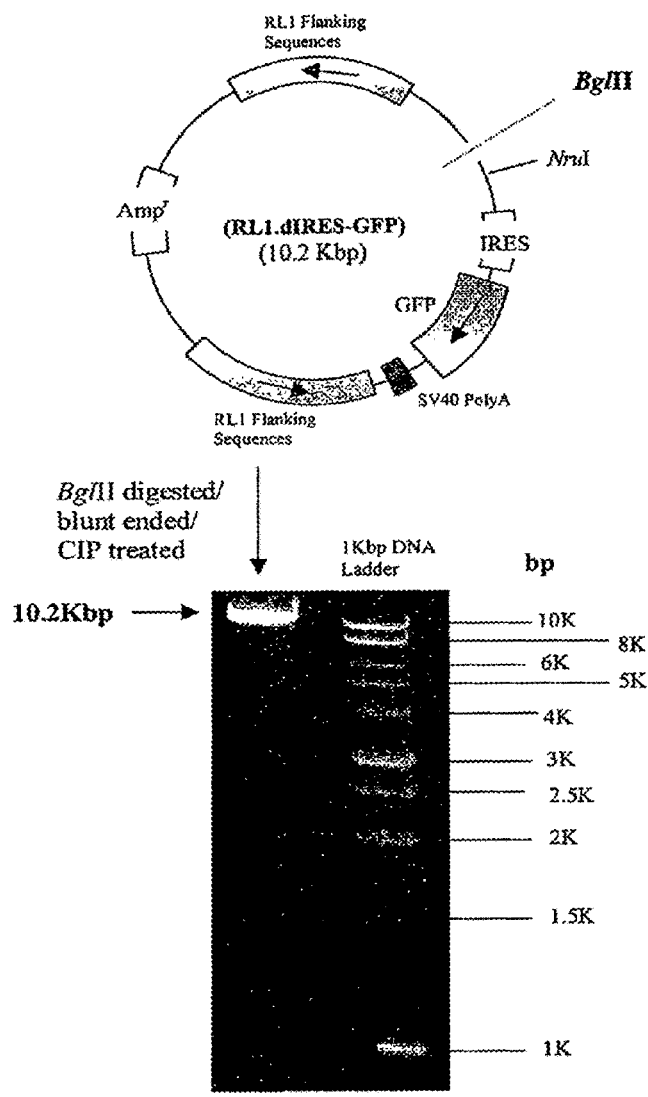

FIG. 9. Agarose gel electrophoresis of BglII digested, blunt ended, CIP treated RL1.dIRES-GFP. RL1.dIRES.GFP was digested with BglII. The digested plasmid was then blunt ended using Klenow polymerase and treated with Calf Intestinal Phosphatase (CIP) to prevent the vector re-annealing to itself in subsequent ligation reactions. A sample of the digested/blunt ended/CIP treated DNA was electrophoresed, beside a 1 Kbp DNA ladder (Promega), on a 1% agarose gel to check its concentration. pCMV-asSCCRO was subsequently cloned into this digested/CIP treated vector.

Figure 10:
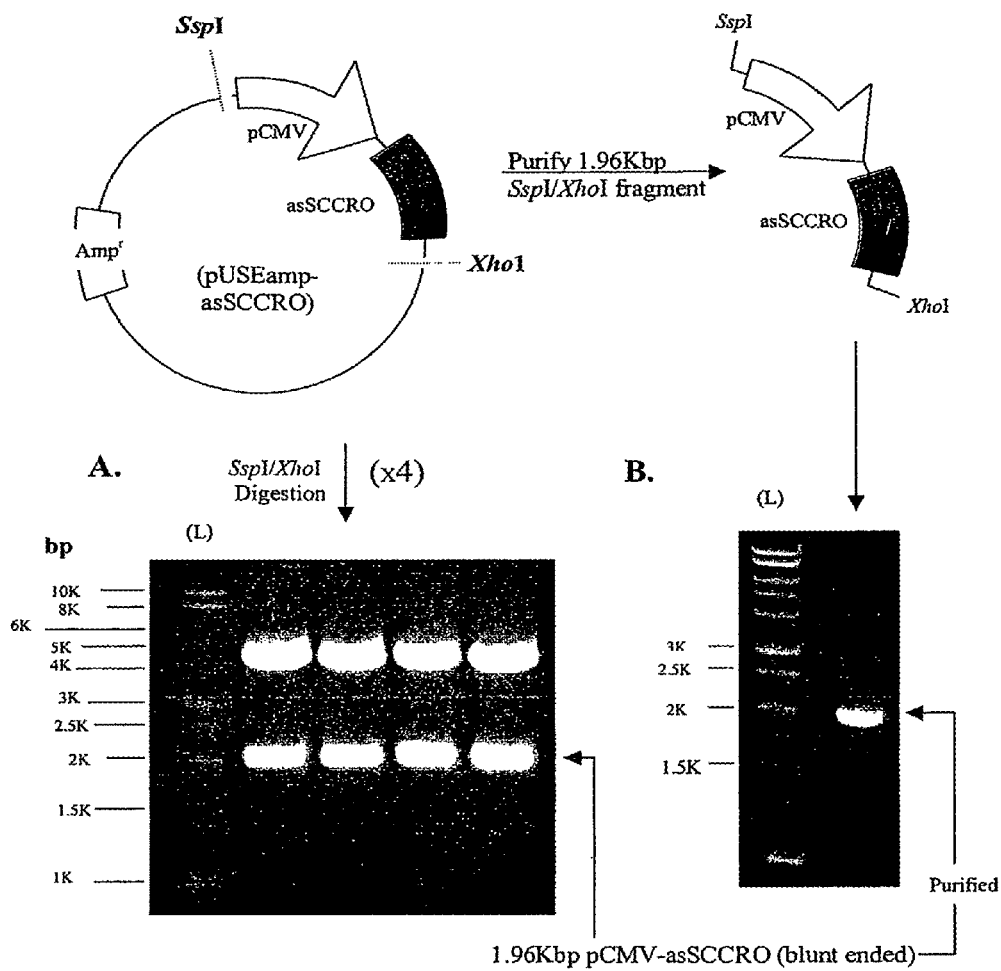

FIG. 10. Agarose gel electrophoresis of SspI/XhoI digested pUSEamp-asSCCRO (A) and the purified pCMV-asSCCRO fragment (B). Four samples of pUSEamp-asSCCRO were digested with SspI and XhoI then electrophoresed, beside a 1 Kbp DNA ladder (L) (Promega), on a 1% agarose gel. The 1.96 Kbp fragments, consisting of DNA antisense to the squamous cell carcinoma related oncogene (asSCCRO) downstream of the CMV IE promoter (pCMV), were purified from the gel, blunt ended using Klenow polymerase, purified again and a sample of the purified DNA electrophoresed on an agarose gel to check its concentration.

Figure 11:
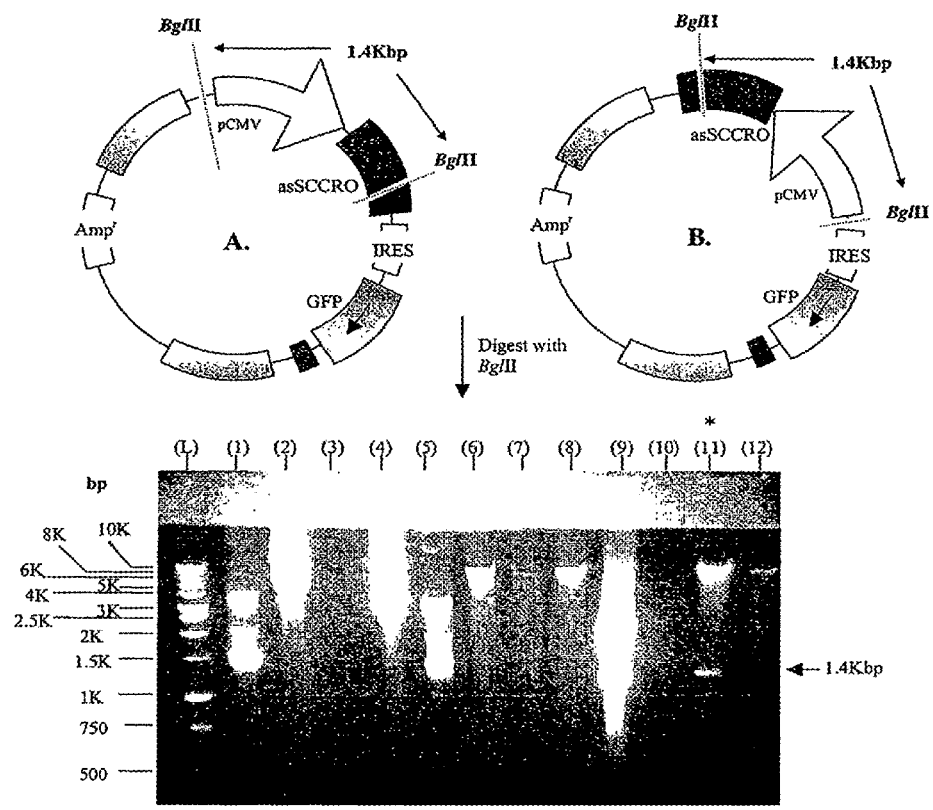

FIG. 11. Identification of RL1.dIRES-GFP clones containing the pCMV-asSCCRO insert. Ligation reactions were set up with the purified, blunt ended pCMV-asSCCRO fragment and BglII digested, blunt ended, CIP treated RL1.dIRES-GFP. Bacteria were transformed with samples from the ligation reactions and plated onto LBA (Amp$^r$) plates. Colonies were picked and plasmid DNA was extracted and digested with BglII. Digested samples were electrophoresed, beside a 1 Kbp DNA ladder (L) (Promega), on a 1% agarose gel.

*Clone 11 contained the pCMV-asSCCRO insert as two fragments of the predicted size—1.4 Kbp and 10.8 Kbp were generated from BglII digestion. Clones without the insert would not produce a fragment of 1.4 Kbp when digested with BglII.

Figure 12:
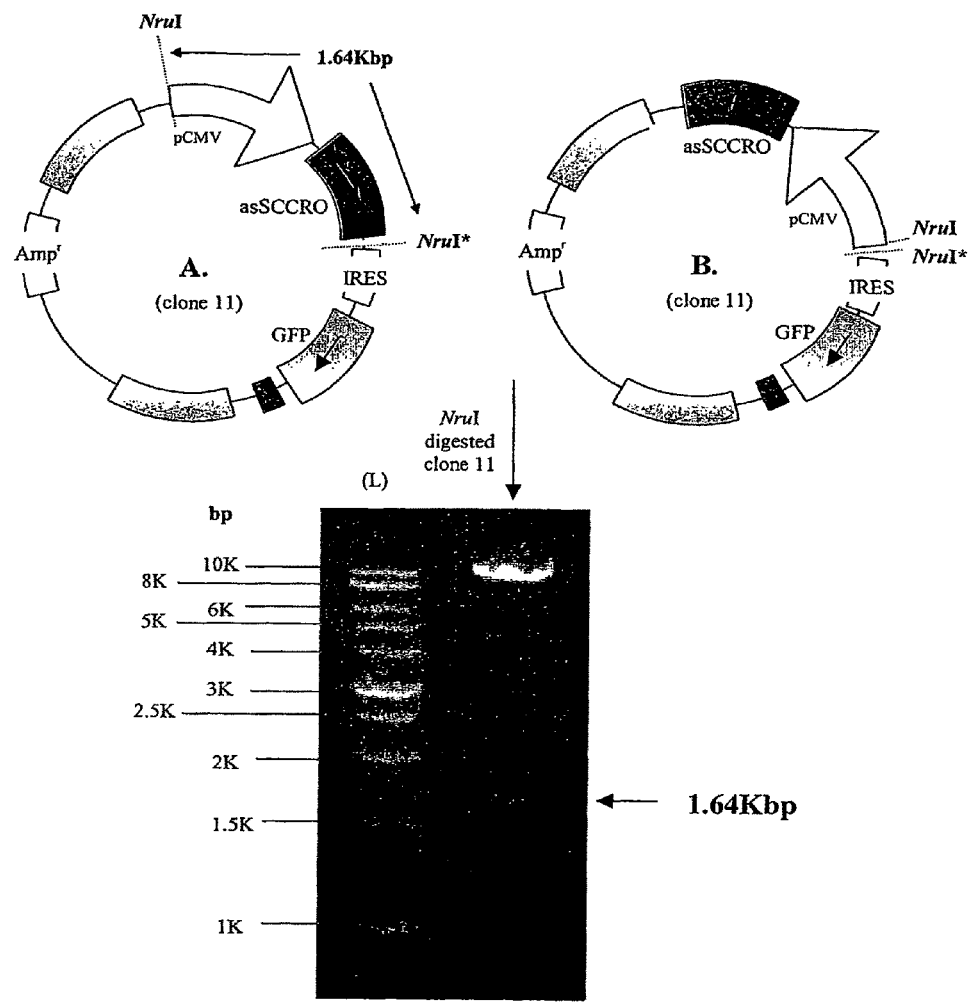

FIG. 12. Determination of the orientation of pCMV-asSCCRO in clone 11. The presence of an NruI site, ~320 bp into the cloned pCMV-asSCCRO fragment, was utilized to determine the orientation of pCMV-asSCCRO. Clone 11 was digested with NruI and electrophoresed, beside a 1 Kbp DNA ladder (L) (Promega), on a 1% agarose gel. If pCMV-asSC-CRO was in the desired orientation (A), NruI digestion would produce a fragment of 1.64 Kbp. If in the opposite orientation (B), no 1.64 Kbp fragment would be generated from this digestion. The presence of a fragment at 1.64 Kbp in the gel confirmed that pCMV-asSCCRO was in the desired orientation. (*This NruI site was already present in the initial cloning vector (i.e. RL1.dIRES-GFP)).

Figure 13:
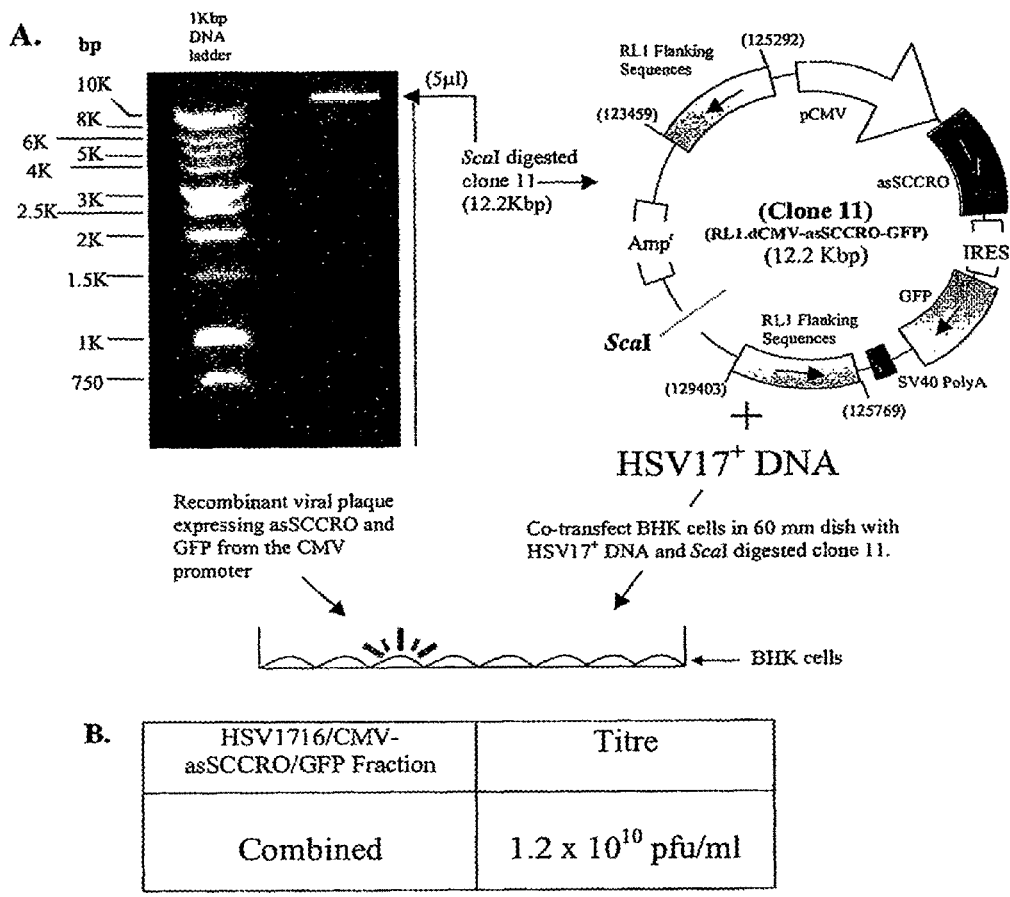

FIG. 13. Agarose gel electrophoresis of ScaI digested clone 11 (A) and HSV1716/CMV-asSCCRO/GFP virus titre (B). Clone 11 (RL1.dCMV-asSCCRO-GFP) was digested with ScaI, the digested DNA purified and 5 μl electrophoresed, beside a 1 Kbp DNA ladder (Promega), on a 1% agarose gel, to check its concentration. 80% confluent BHK cells were then co-transfected with 10 μl HSV17$^+$ DNA and an appropriate volume of the remaining digested clone 11. The cells were incubated at 37° C. for 3 days until cpe was evident. Recombinant viral plaques were picked under the fluorescent microscope, purified and a virus stock, named HSV1716/CMV-asSCCRO/GFP, grown up. HSV1716/CMV-asSC-CRO/GFP was titrated on BHK cells.

Figure 14:
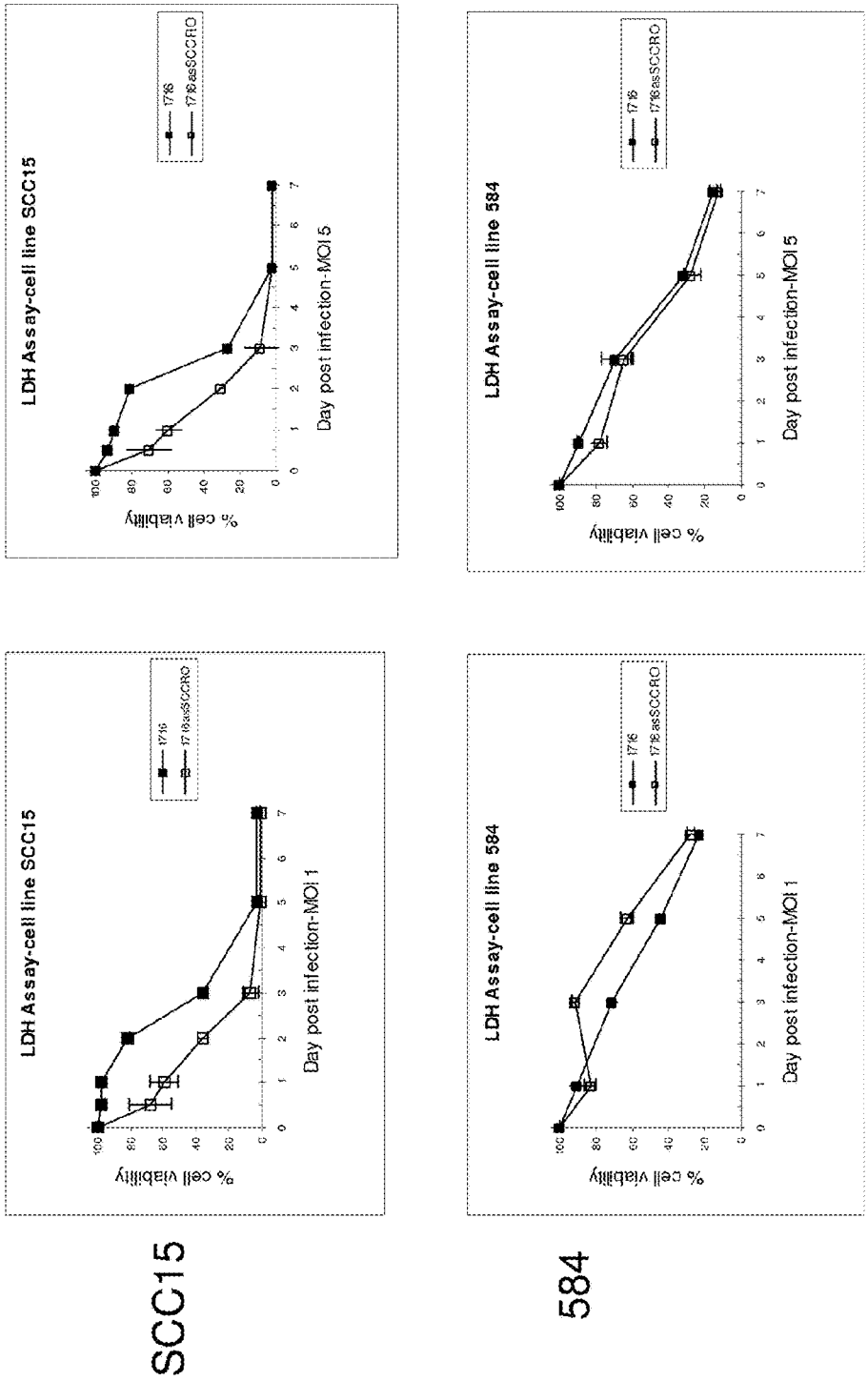

FIG. 14. Cytotoxicity assay for cell lines SCC15 and 584 after infection with HSV1716 or HSV1716asSCCRO at MOI of 1 pfu/cell and 5 pfu/cell.

Figure 15:
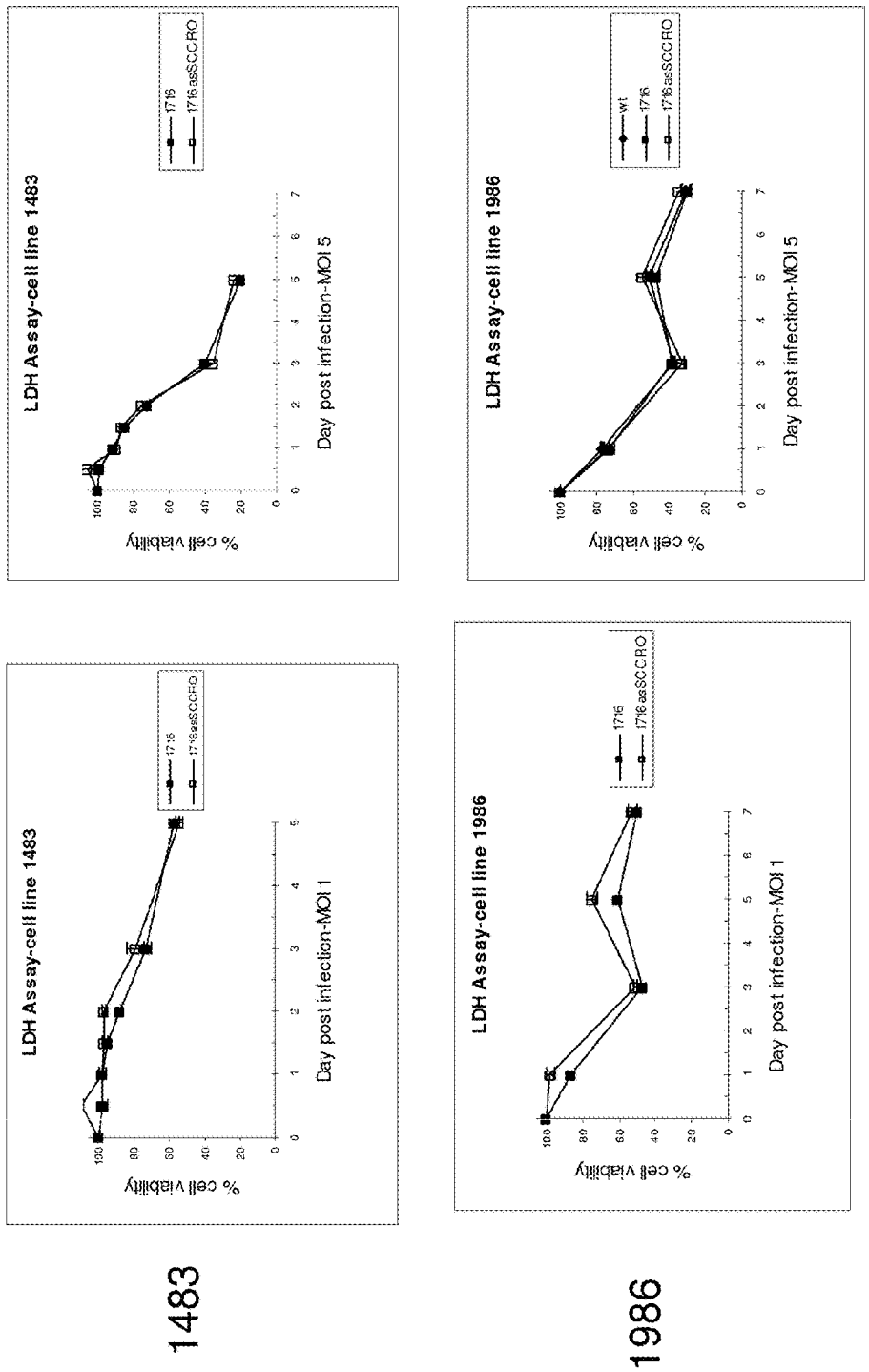

FIG. 15. Cytotoxicity assay for cell lines 1483 and 1986 after infection with HSV1716 or HSV1716asSCCRO at MOI of 1 pfu/cell and 5 pfu/cell.

Figure 16:
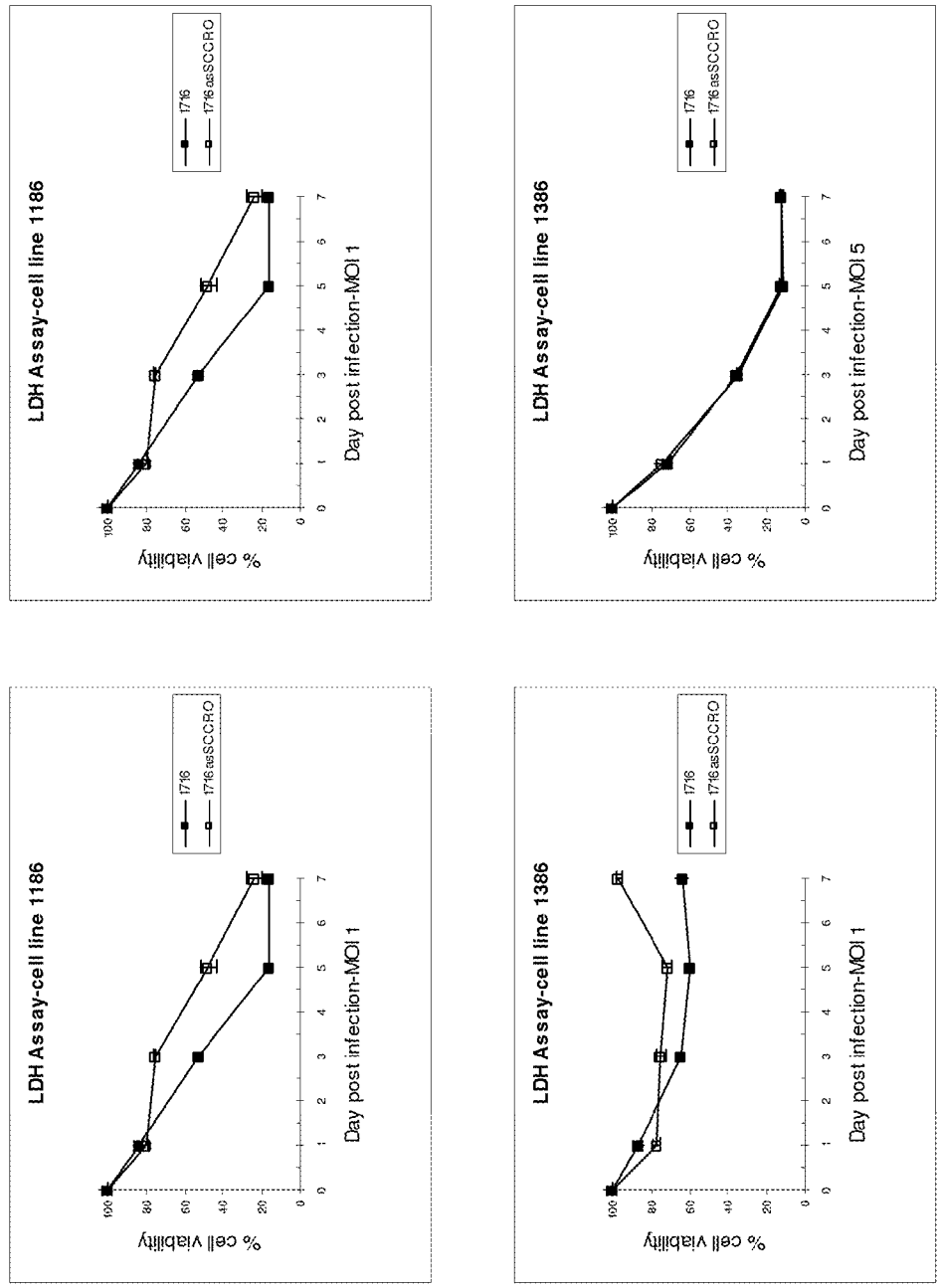

FIG. 16. Cytotoxicity assay for cell line 1186 and 1386 after infection with HSV1716 or HSV1716asSCCRO at MOI of 1 pfu/cell and 5 pfu/cell.

Figure 17:
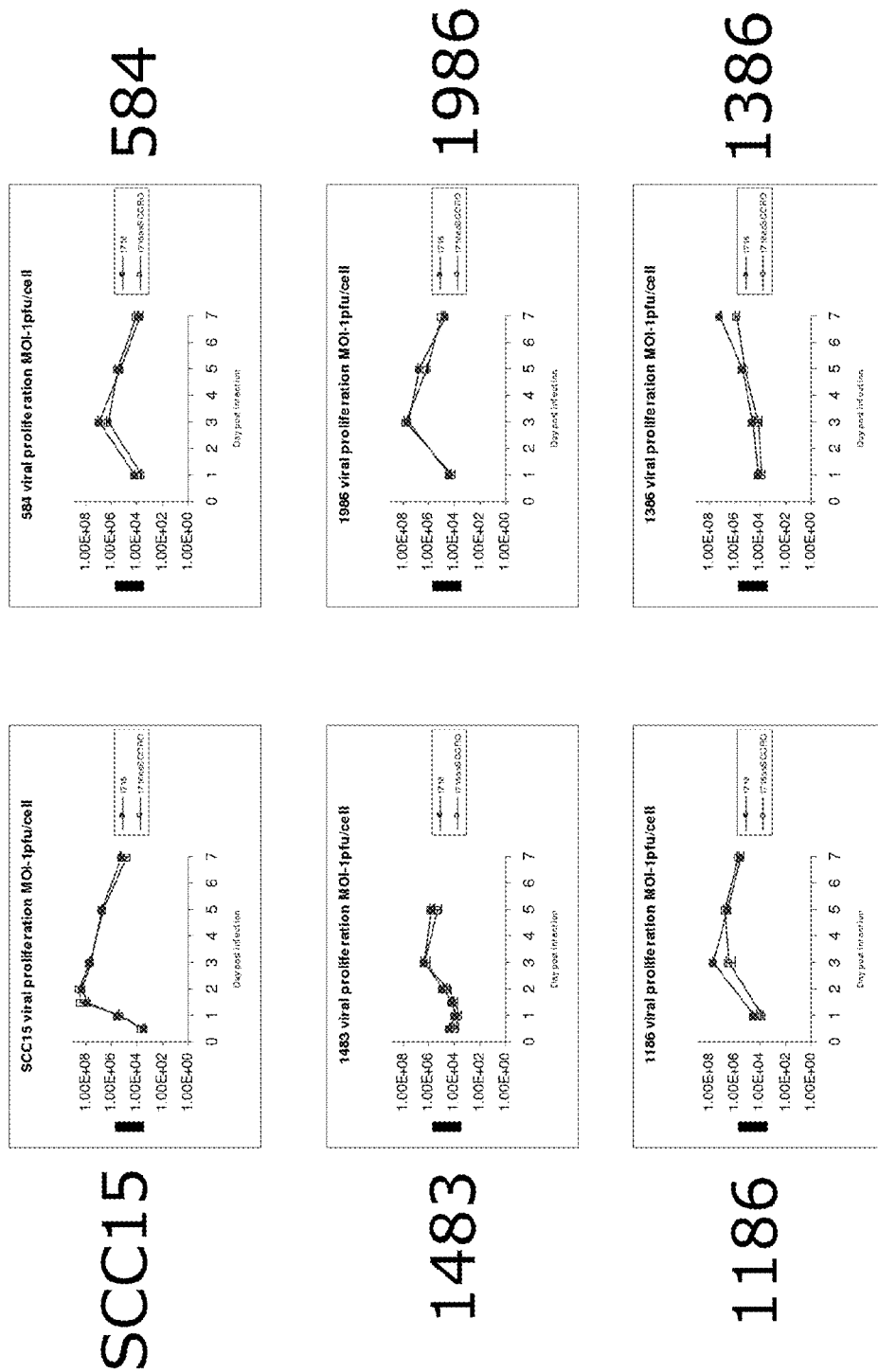

FIG. 17. Viral proliferation assays for head and neck squamous cell carcinoma cell lines after infection with HSV1716 or HSV1716asSCCRO at MOI 1 pfu/cell.

Figure 18:
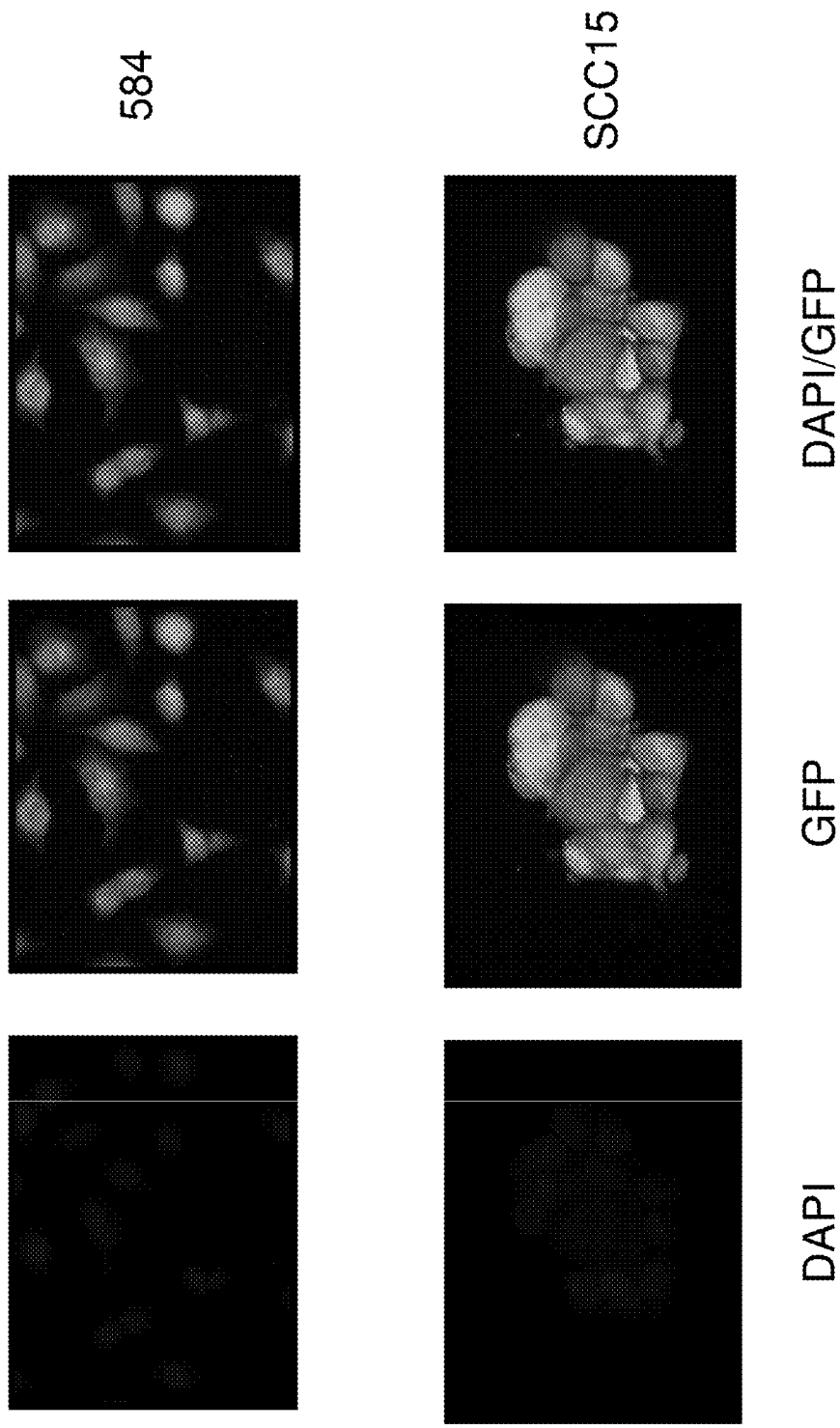

FIG. 18. Infectivity assay—gfp expression 6 hours post infection with 1716gfp virus.

Figure 19:
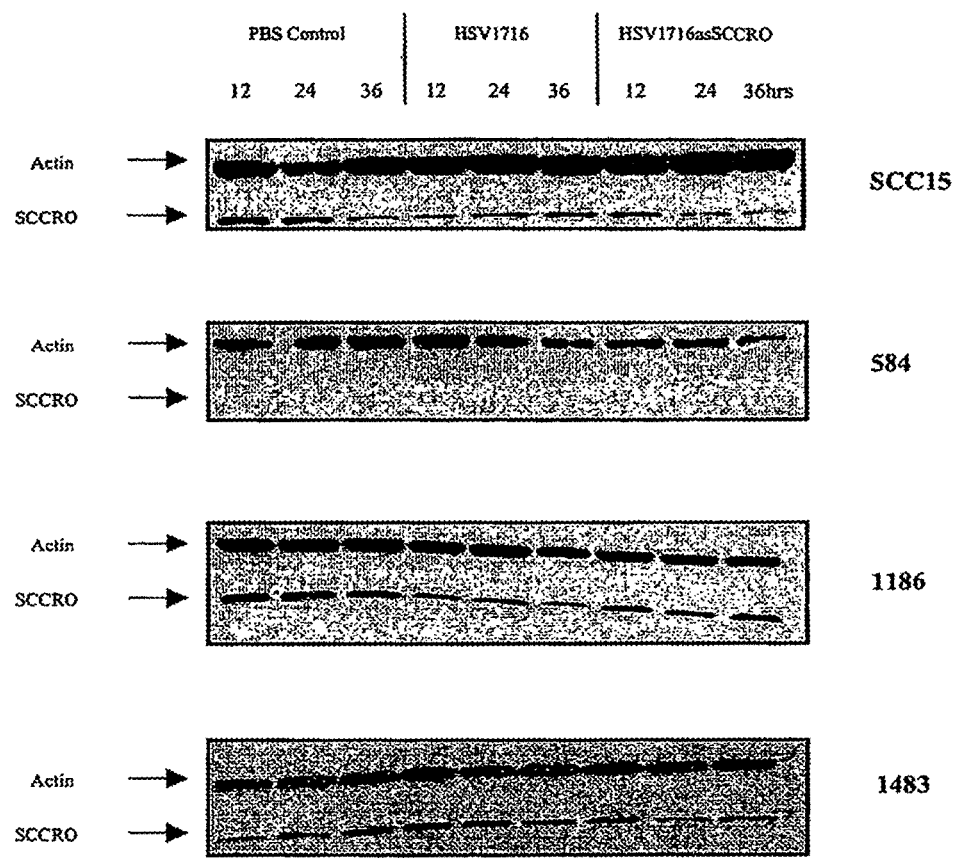

FIG. 19. Western blot results of the cell line SCC15 showing downregulation of SCCRO protein at 12 hours with HSV1716asSCCRO but not in 584.

Figure 20:
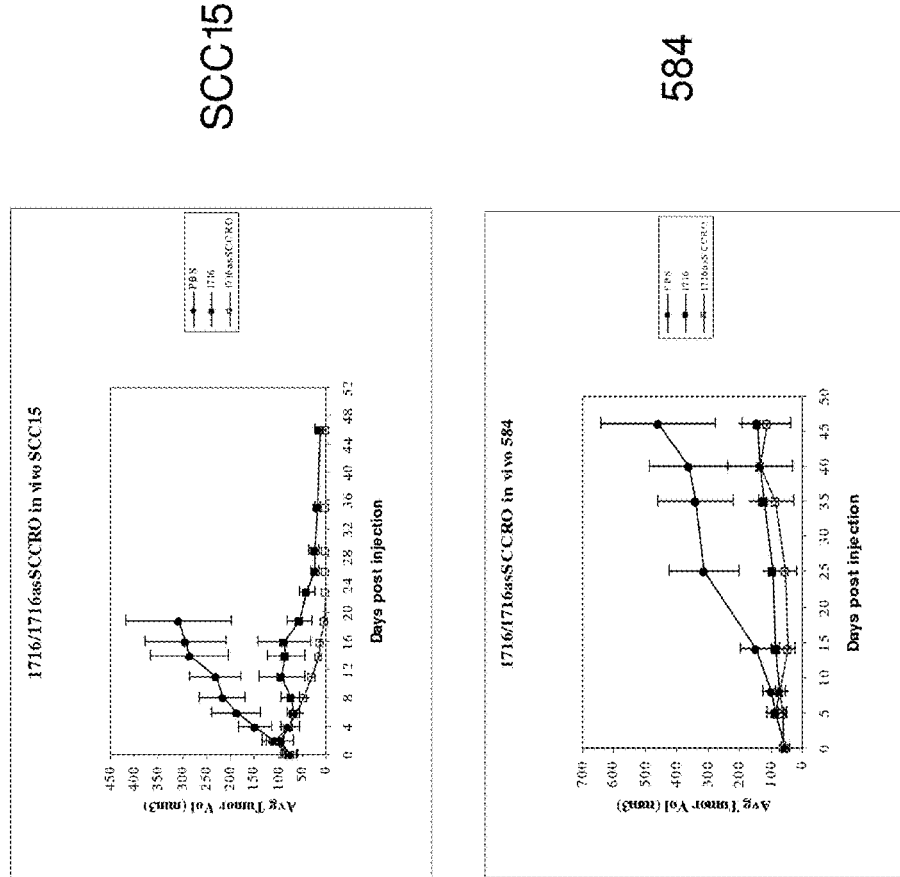

FIG. 20. Nude mice xenograft growth curves in SCC15 and 584 following single intratumoural injection of HSV1716 or HSV1716asSCCRO.

Figure 21:
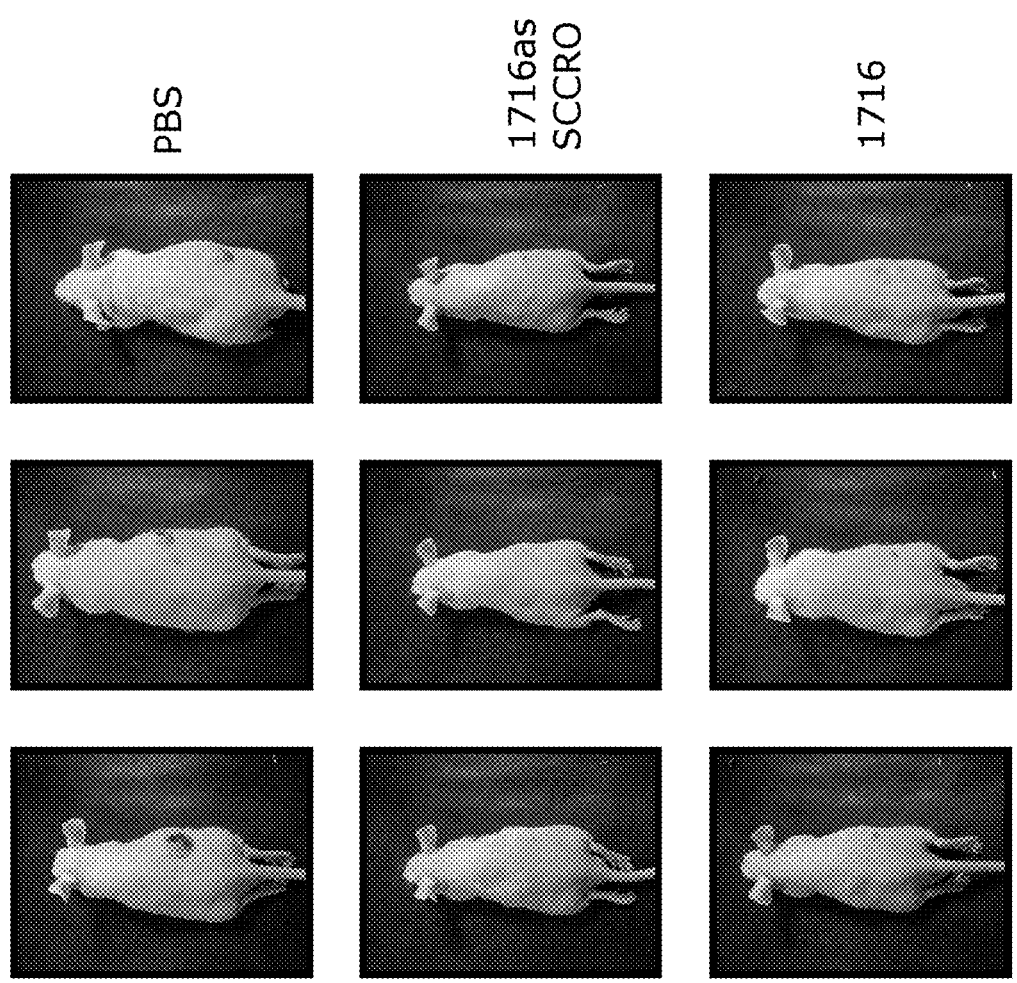

FIG. 21. Nude mice xenograft growth curves in SCC15 following single intratumoural injection of PBS, HSV1716 or HSV1716asSCCRO.

Figure 22A:
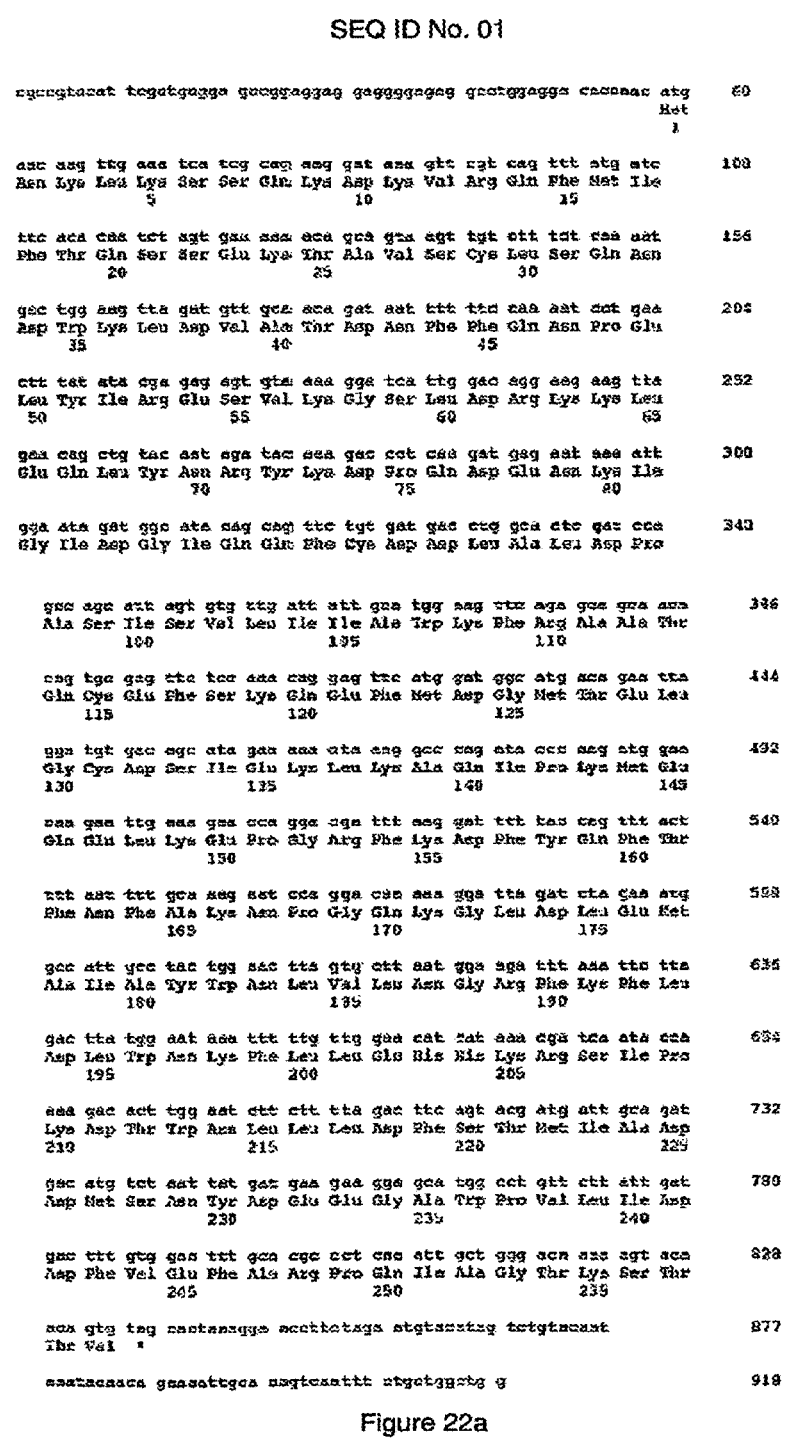

FIG. 22.
(A) SEQ ID No. 1—a Human SCCRO nucleic acid sequence. Also showing the amino acid sequence of the encoded polypeptide (an SCCRO gene product);
(B) SEQ ID No. 2—Amino acid sequence of the polypeptide encoded by SEQ ID No.1;
(C) SEQ ID No. 3—a Human SCCRO nucleic acid sequence. Also showing the amino acid sequence of the encoded polypeptide (an SCCRO gene product);
(D) SEQ ID No. 4—Amino acid sequence of the polypeptide encoded by SEQ ID No.3.

FIG. 23. (A) DNA nucleotide sequence encoding the siRNA construct designed to target expression of the SCCRO gene (SEQ ID No. 5); and (B) nucleotide sequence encoding control siRNA (SEQ ID No 6). Sequences either side of the central nucleotides are respectively complimentary enabling the transcribed RNA to form a hairpin structure (stem-loop) by binding of complementary nucleotides.

DETAILED DESCRIPTION OF THE BEST MODE OF THE INVENTION

Specific details of the best mode contemplated by the inventors for carrying out the invention are set forth below, by way of example. It will be apparent to one skilled in the art that the present invention may be practiced without limitation to these specific details.

Vectors Useful for Generation of Herpes Simplex Virus Mutants

Mutant herpes simplex viruses of the invention may be generated by use of nucleic acid vectors.

One such vector useful for generation of mutant herpes simplex viruses according to the present invention is a nucleic acid vector comprising, consisting or consisting essentially of:
first and second nucleotide sequences corresponding to nucleotide sequences flanking an insertion site in the genome of a selected herpes simplex virus; and
a cassette located between said first and second nucleotide sequences comprising nucleic acid encoding:
  a) one or a plurality of insertion sites; and
  b) a ribosome binding site; and
  c) a marker.

Another vector useful for generation of mutant herpes simplex viruses according to the present invention is a nucleic acid vector comprising, consisting or consisting essentially of:
first and second nucleotide sequences corresponding to nucleotide sequences flanking an insertion site in the genome of a selected herpes simplex virus; and
a cassette located between said first and second nucleotide sequences comprising nucleic acid encoding:
  a) one or a plurality of insertion sites; and
  b) a first regulatory nucleotide sequence; and
  c) a marker.

The first and second nucleotide sequences may correspond to nucleotide sequences flanking an insertion site formed in, or comprising all or a part of, the ICP34.5 protein coding sequence of the genome of a selected herpes simplex virus.

The cassette may comprise a plurality of insertion sites, each insertion site preferably formed by nucleic acid encoding a specific restriction endonuclease site ('restriction site'). Together the restriction sites may form a multiple cloning site (MCS) comprising a series of overlapping or distinct restriction sites, preferably a series of distinct restriction sites comprising one or more of the ClaI, BglII, NruI, XhoI restriction sites.

The encoded components of the cassette may be arranged in a predetermined order. In one arrangement, the one or plurality of insertion sites is/are arranged upstream (i.e. 5') of the ribosome binding site/first regulatory sequence and the ribosome binding site/first regulatory sequence is arranged upstream (i.e. 5') of the marker.

The first and second nucleotide sequences may comprise nucleotide sequences having identity to regions of the genome surrounding the insertion site in the selected herpes simplex virus (the 'viral insertion site'). These sequences enable the cassette to be incorporated at the viral insertion site by homologous recombination between the first and second nucleotide sequences and their respective corresponding sequences in the viral genome.

Thus the first and second nucleotide sequences are flanking sequences for homologous recombination with corresponding sequences of a selected viral genome, such homologous recombination resulting in insertion of the cassette at the viral insertion site.

The first and second nucleotide sequences may correspond to nucleotide sequences flanking an insertion site in the RL1 locus of the HSV genome, more preferably in the ICP34.5 protein coding sequence of the HSV genome.

The first and second nucleotide sequences may each be at least 50 bp in length, more preferably at least 100, 150, 200, 300, 400, 500, 600, 700, 800, 900, 1000, 1100, 1200, 1300, 1400, 1500, 1600, 1700, 1800, 1900 2000, 2100, 2200, 2300, 2400, 2500, 2600, 2700, 2800, 2900, 3000, 3100, 3200, 3300, 3400, 3500, 3600, 3700, 3800, 3900 or 4000 bp in length. Each of the first and second nucleotide sequences may have at least 50% sequence identity to their corresponding sequence in the viral genome, more preferably at least 60%, 70%, 75%, 80%, 85%, 90%, 92%, 94%, 95%, 96%, 97%, 98% 99% or 100% identity. Identity of sequences is determined across the entire length of a given nucleotide sequence. Where sequences are of different length, sequence identity of the shorter sequence is determined over the entire length of the longer sequence.

The first and second nucleotide sequences may be characterised by the ability of one strand of a given sequence to hybridise with the corresponding single-stranded complement of the HSV genome under varying hybridisation stringency conditions. Suitably, the first and second nucleotide sequences will hybridise with their corresponding complement under very low, low or intermediate stringency conditions, more preferably at high or very high stringency conditions.

The viral insertion site is the position between the genomic nucleotide sequences corresponding to the first and second nucleotide sequences of the vector (the 'genomic' and 'vector flanking sequences' respectively) at which homologous recombination will occur and may be predetermined by selection of the vector flanking sequences. Where the genomic flanking sequences are immediately adjacent, the insertion site is the position between the peripheral and immediately adjacent bases of the two genomic flanking sequences, such that insertion of the cassette separates the genomic flanking sequences. Where the genomic flanking sequences are separated by one or a plurality of bases in the viral genome, the insertion site is formed by said one or a plurality of bases which are excised from the genome by the homologous recombination event.

The position of the viral insertion site may be accurately selected by careful selection and construction of the vector flanking sequences. Accordingly, the vector may be constructed such that homologous insertion of the cassette results in disruption of a chosen protein coding sequence and inactivation of the respective gene product or such that the cassette is inserted at a non-protein coding region of the viral genome. The complete genome sequences of several herpes simplex virus strains have been reported and are publicly available. The complete genome sequence for HSV-1 strain 17syn+ was reported by Dolan et al[3] (incorporated herein by reference) and the complete genome sequence of HSV-2 strain HG52 was reported by Dolan et al[4] (incorporated herein by reference) and is available from the EMBL database under accession code Z86099. Using this information, the vector of the present invention may preferably be designed for use in generating mutant HSV-1 (e.g. in strain 17 or F) or mutant HSV-2 (e.g. in strain HG52).

The first and second nucleotide sequences (vector flanking sequences) may each comprise sequence corresponding to the RL terminal repeat region of the genome of the selected HSV (e.g. HSV-1 strains 17 or F or HSV-2 strain HG52). The vector flanking sequences may comprise, consist or consist essentially of nucleotide sequences of the RL repeat region which flank the ICP34.5 protein coding sequence. In flanking the ICP34.5 coding sequence, one or both of the selected sequences may, in the corresponding HSV genome, overlap, i.e. extend into, the ICP34.5 protein coding sequence or one or both sequences may be selected so as to not overlap the ICP34.5 protein coding sequence. In a similar manner, the selected sequences may be chosen to overlap completely or partially other important encoded signals, e.g. transcription initiation site, polyadenylation site, defined promoters or enhancers. In this preferred arrangement the insertion site will thus comprise all or a part of the ICP34.5 protein coding sequence and/or be such that the inserted cassette disrupts the ICP34.5 protein coding sequence.

The vectors described, comprising first and second nucleotide sequences corresponding to regions of the RL repeat region flanking and/or overlapping the ICP34.5 protein coding sequence, may be used in the generation of ICP34.5 null mutants wherein all or a portion of the ICP34.5 protein coding sequence is excised and replaced during the homologous recombination event such that both copies of the ICP34.5 coding sequence are disrupted.

The recombination may result in an insertion of nucleic acid within the ICP34.5 protein coding sequence thereby disrupting that sequence. In that case, successfully transformed virus are thus mutants incapable of generating the ICP34.5 active gene product from at least one copy, and preferably from both copies, of the ICP34.5 gene.

Successfully transformed virus are thus mutants incapable of generating the ICP34.5 active gene product.

Each component of the cassette may be positioned substantially adjacent the neighbouring component such that a single bicistronic transcript comprising or consisting essentially of the mRNA encoding the nucleotide sequence of interest, ribosome binding site and marker is obtainable.

The vectors described may further comprise, consist, or consist essentially of a nucleic acid encoding a selectable marker such as a polypeptide or protein conferring antibiotic resistance e.g. kanamycin resistance or ampicillin resistance.

The vectors described are preferably DNA vectors, particularly dsDNA vectors. The vector may be provided as a linear or circular (plasmid) DNA vector. The vector preferably contains nucleotide sequences, e.g. restriction endonuclease site(s), permitting transition between the two forms by use of DNA ligation and restriction materials (e.g. enzymes) and techniques known to the person skilled in the art. To achieve homologous recombination with a selected HSV, the vector is preferably provided in linear form.

One such vector provided by the inventors is plasmid RL1.dIRES-GFP deposited in the name of Crusade Laboratories Limited having an address at Department of Neurology Southern General Hospital 1345 Govan Road Govan Glasgow G51 5TF Scotland on 3 Sep. 2003 at the European Collection of Cell Cultures (ECACC), Health Protection Agency, Porton Down, Salisbury, Wiltshire, SP4 0JG, United Kingdom under accession number 03090303 in accordance with the provisions of the Budapest Treaty on the International Recognition of the Deposit of Microorganisms for the Purposes of Patent Procedure (herein referred to as the 'Budapest Treaty').

RL1.dIRES-GFP provides a platform for generating a plurality of 'shuttle vectors' which can exploit the process of homologous recombination to transfer a nucleotide sequence of interest (downstream of a selected promoter) into the disabling RL1 locus of HSV-1, generating easily identifiable, oncolytic, ICP34.5 null HSV-1 mutants expressing the products of the nucleotide sequence of interest, e.g. an RNA transcript or a polypeptide, and GFP. RL1.dIRES-GFP thus provides for ease of generation and purification of ICP34.5 null HSV.

RL1.dIRES-GFP is a useful vector for making second-generation oncolytic viruses having enhanced cytotoxic potential and which may express the product(s) of selected gene(s) to enhance the oncolytic and/or therapeutic effect of the administered virus.

The RL1.dIRES-GFP plasmid incorporates a multi-cloning sequence (MCS), upstream of an internal ribosome entry site (IRES), the GFP gene and SV40 polyadenylation sequences flanked by HSV-1 RL1 sequences. Incorporation of the encephalomyocarditis virus IRES (EMCV IRES) permits translation of two open reading frames from a single transcribed mRNA.

Following generation of a specific shuttle vector by cloning of the nucleotide sequence of interest (and the selected promoter) into RL1.dIRES-GFP, recombinant HSV-1 expressing the desired nucleic acid transcript or protein, can be generated and purified within 2 weeks. This compares with 2-3 months using prior art protocols.

In the ICP34.5 null HSV generated using the RL1.dIRES-GFP plasmid provided by the inventors transcription of both the nucleotide sequence of interest and GFP as a single transcript is controlled by the same promoter upstream of the nucleotide sequence of interest, the transcribed IRES directing cap-independent translation of GFP. The generated ICP34.5 null HSV are non-neurovirulent. By modifying the RL1.dIRES-GFP plasmid to incorporate appropriate flanking sequences surrounding the cassette other gene-specific HSV null mutants expressing GFP can be generated.

RL1.dIRES-GFP is promoterless, thus enabling a promoter of choice to be incorporated in the homologously recombined shuttle vector for controlling expression of the nucleotide sequence of interest from the inserted cassette.

Plasmid RL1.dIRES-GFP or modified plasmid shuttle vectors thereof further comprising nucleotide sequence encoding a nucleic acid transcript or polypeptide of interest may be provided in isolated or purified form.

The vector may be a variant of plasmid RL1.dIRES-GFP.

As the plasmid RL1.dIRES-GFP is designed for tandem expression of a sequence of interest and the marker gene encoding green fluorescent protein (GFP). The sequence of interest is cloned into RL1.dIRES-GFP along with its promoter (e.g. CMV) such that the promoter drives transcription of an mRNA for the sequence of interest along with the IRES-GFP. Translation results in expression of the GFP from the internal ribosomal entry site and the gene of interest and promoter must be cloned into RL1.dIRES-GFP in the correct orientation to achieve this. There are a number of instances where this tandem expression arrangement may be unsuitable and a variation of the cassette design is favourable.

One example is the expression of siRNAs as short hairpin RNAs using RNA polIII promoters such as H1 or U6. These promoters are unable to drive the additional tandem expression of the IRES-GFP as the RNApolIII expression cassette is designed only to produce short transcripts. Additionally, sequences of interest derived from genomic DNA with strong mRNA shut-off signals in their 3' untranslated regions may not support IRES-GFP expression.

Thus in some cases a cassette may be provided in which the sequence of interest and marker are expressed separately from independent promoters.

One variant contains a cassette in which the ribosome binding site of plasmid RL1.dIRES-GFP is replaced with a regulatory nucleotide sequence, preferably a strong, constitutive promoter such as the Phosphoglycerokinase promoter. The marker is thereby expressed under the control of this (the 'first') regulatory sequence. The nucleotide sequence of interest (e.g. antisense or siRNA) is expressed under the control of a second regulatory sequence upstream (5') of the nucleotide sequence of interest, e.g. the CMV promoter. This vector variant is particularly suitable for expression of siRNA where a weak promoter may be used for expression of the siRNA molecule or the nucleic acid encoding the siRNA may have a strong termination signal making it difficult to produce a single bi- or poly-cistronic transcript containing the transcribed siRNA and marker sequence. In this arrangement the transformed virus containing the cassette integrated in the viral genome produces two separate transcripts under the control of the first and second promoters.

This cassette was constructed in the following manner. The 1.3 kbp blunt-ended EcoRI/AflII fragment that contains the PGK promoter/GFP gene was obtained by restriction digestion followed by Klenow treatment from the vector pSNRG and cloned into the RL1-del vector cut with the restriction enzyme NruI that generates blunt ends. Successful insertion of the PGK/GFP DNA was confirmed by BamHI digestion and the orientation of the inserted DNA identified using the unique XhoI site in RL1-del and the BsrGI site at the 3' end of PGK/GFP. Plasmids with PGK/GFP in both forward and reverse orientation were obtained and the plasmids were designated RL1-dPGK/GFPfor and RL1-dPGK/GFPrev. Expression of GFP was confirmed in BHK cells transfected with the forward and reverse orientation plasmids.

Thus, sequences of interest along with their own promoters (although it is preferred that the PGK promoter is not also used for this purpose) can then be cloned into either RL1-dPGK/GFPfor or RL1-dPGK/GFPrev in either orientation using the remaining unique BglII, XhoI or HpaI unique restriction enzyme sites. The resulting plasmid can be used to derive recombinant HSV in which the marker GFP gene and the gene of interest are expressed independently from their own promoters.

The vectors described may be constructed for use in generating engineered HSV-1 or HSV-2 by insertion of a nucleic acid cassette through a mechanism of homologous recombination between nucleotide sequences flanking the cassette and corresponding sequences in the selected herpes simplex virus genome.

The vectors described may comprise and have use as:
i) gene delivery (gene therapy) vectors for delivery of a selected nucleotide sequence, e.g. antisense nucleic acid or siRNA, to a specific locus of the HSV genome; and/or
ii) expression vectors for expression of the delivered nucleotide sequence of i) from the HSV genome under the control of a selected regulatory element; and/or
iii) vectors for the generation of HSV gene-specific null mutants wherein the cassette is inserted at a selected genomic location to disrupt the protein coding sequence of a selected HSV gene such that the gene product is inactive in the resultant mutant virus.

The vectors described may be used in the manufacture of engineered gene specific HSV null mutants, i.e. HSV mutants incapable of expressing an active gene product of a selected gene. They may be used in the manufacture of engineered viruses which express a selected protein from only one gene copy the other gene copy being disrupted or modified such that it cannot express a functional gene product. Such vectors may also be used in the manufacture of a medicament, preferably comprising said gene specific HSV null mutant, for use in treating cancer and tumours, preferably by the oncolytic treatment of the tumour.

The vectors described may also be used in the manufacture of engineered HSV mutants wherein the genome of the mutant HSV comprises a nucleotide sequence which has been inserted in the HSV genome by homologous recombination of the cassette such that the nucleotide sequence is arranged to be transcribed from the HSV genome under the control of a regulatory element e.g. promoter, preferably a regulatory element forming part of the inserted cassette, to produce an antisense transcript or siRNA. Preferably the antisense nucleotide sequence is an exogenous/heterologous (i.e. non-HSV originating) sequence. Such vectors may be used in the manufacture of a medicament, preferably comprising the engineered HSV mutant, for use in the treatment of disease, including the oncolytic treatment of tumours.

The vectors described may also be used in the manufacture of an engineered HSV mutant wherein the genome of the mutant HSV comprises a nucleotide sequence which has been inserted in a protein coding sequence of the HSV genome by homologous recombination of the cassette such that the mutant HSV is incapable of expressing the active gene encoded by said protein coding sequence and wherein the inserted nucleotide sequence is expressed under the control of a regulatory element to produce an antisense transcript or siRNA. Preferably, the regulatory element forms part of the cassette. Such vectors may be used in the manufacture of a medicament, preferably comprising the engineered HSV mutant, for use in the treatment of disease, including the oncolytic treatment of tumours.

The vectors described may be used to generate mutant HSV by inserting the cassette into the genome of a selected HSV, the method of generation may comprise providing a vector described above, where the vector is a plasmid, linearising the vector; and co-transfecting a cell culture with the linearised vector and genomic DNA from said HSV.

The co-transfection may be carried out under conditions effective for homologous recombination of said cassette into an insertion site of the viral genome.

The method may further comprise one or more of the steps of:
1) screening said co-transfected cell culture to detect mutant HSV expressing said marker; and/or
2) isolating said mutant HSV; and/or
3) screening said mutant HSV for expression of the nucleotide sequence of interest or the RNA or polypeptide thereby encoded; and/or
4) screening said mutant HSV for lack of an active gene product; and/or
5) testing the oncolytic ability of said mutant HSV to kill tumour cells in vitro.

Example 1

Construction of Plasmid RL1.dIRES-GFP

General Approach

Figure 1:
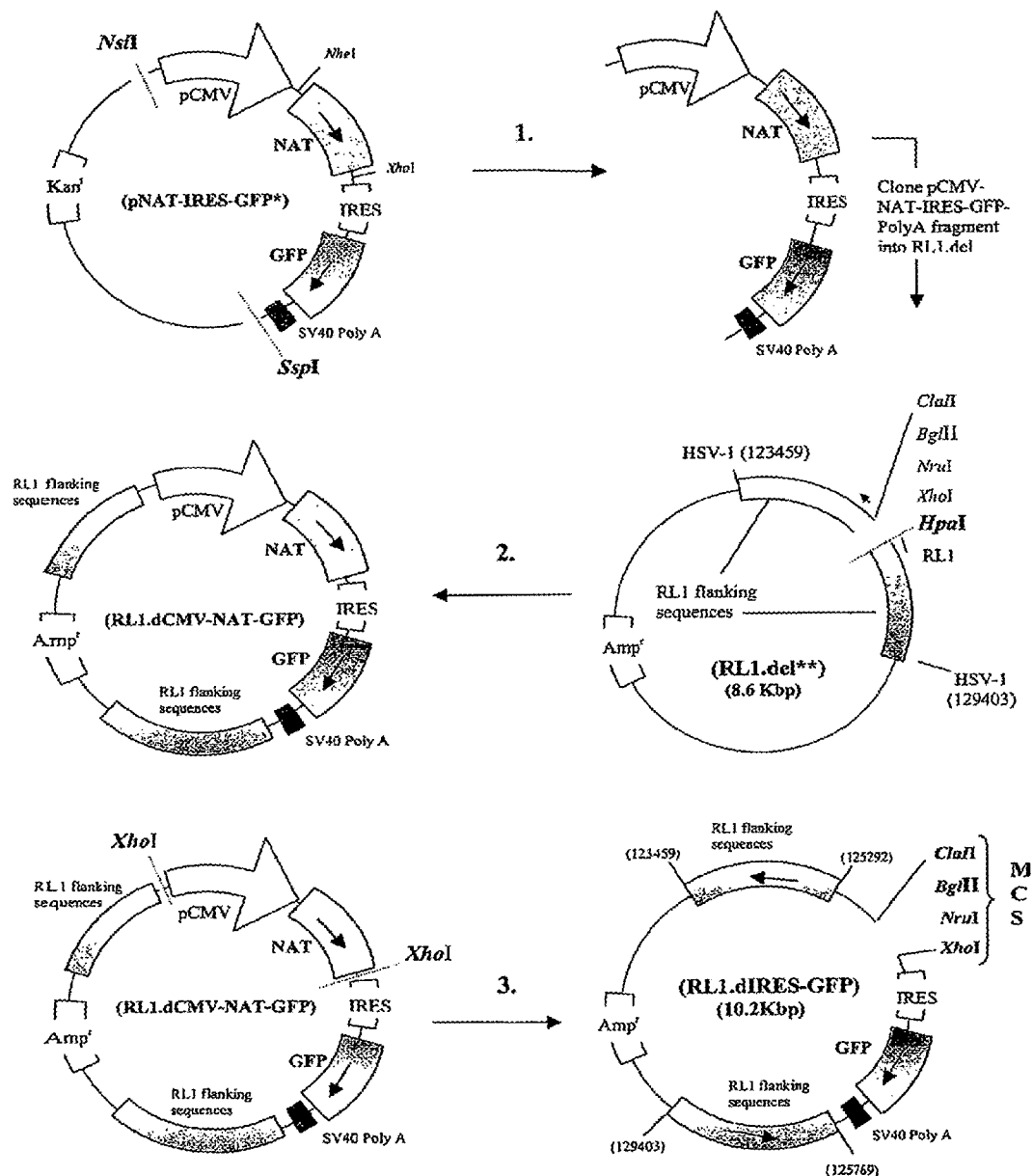
FIG. 1. Generation of plasmid RL1.dIRES-GFP from plasmids pNAT-IRES-GFP and RL1.del.

Plasmid RL1.dIRES-GFP was generated in three stages, illustrated in FIG. 1.

1. The DNA sequences containing the CMV IE promoter (pCMV), the NAT gene, the internal ribosome entry site (IRES), the GFP reporter gene and the SV40 polyadenylation sequences were excised from pNAT-IRES-GFP using NsiI and SspI and purified.

2. The purified pCMV-NAT-IRES-GFP-PolyA DNA fragment was cloned into RL1.del to form a new plasmid designated RL1.dCMV-NAT-GFP.

3. The pCMV-NAT DNA sequences of RL1.dCMV-NAT-GFP were excised using XhoI and the remainder of the plasmid re-ligated to form a novel plasmid designated RL1.dIRES-GFP. This novel plasmid contained a multi-cloning site (all sites shown are unique) upstream of an IRES, the GFP gene and the SV40 polyA sequences all within the HSV-1 RL1 flanking sequences. Recombinant ICP34.5 null HSV-1, expressing a gene of interest in the RL1 locus, can be generated by cloning the gene of interest (downstream of a suitable promoter) into the multi-cloning site and co-transfecting BHK cells with the plasmid and HSV-1 DNA. Recombinant virus expressing the target gene can be identified using GFP fluorescence.

Removal of the CMV promoter and noradrenaline transporter gene (pCMV-NAT) from RL1.dCMV-NAT-GFP, followed by re-ligation of the remainder of the plasmid, resulted in a novel plasmid (RL1.dIRES-GFP) containing a multi-cloning site (MCS), upstream of the encephalomyocarditis virus internal ribosome entry site (EMCV IRES), the GFP reporter gene and the SV40 PolyA sequences, all within RL1 flanking sequences. This novel arrangement of DNA sequences or 'smart cassette' allows ICP34.5 null HSV-1, expressing a gene of interest in the RL1 locus, to be easily generated by simply inserting the desired transgene (downstream of a suitable promoter) into the MCS and co-transfecting BHK cells with the plasmid and HSV-1 DNA. The IRES situated between the GFP gene and the MCS permits expression of two genes from the same promoter and so recombinant virus expressing the gene of interest also expresses GFP and can therefore be easily identified under a fluorescence microscope and purified.

Materials and Methods

Figure 2:
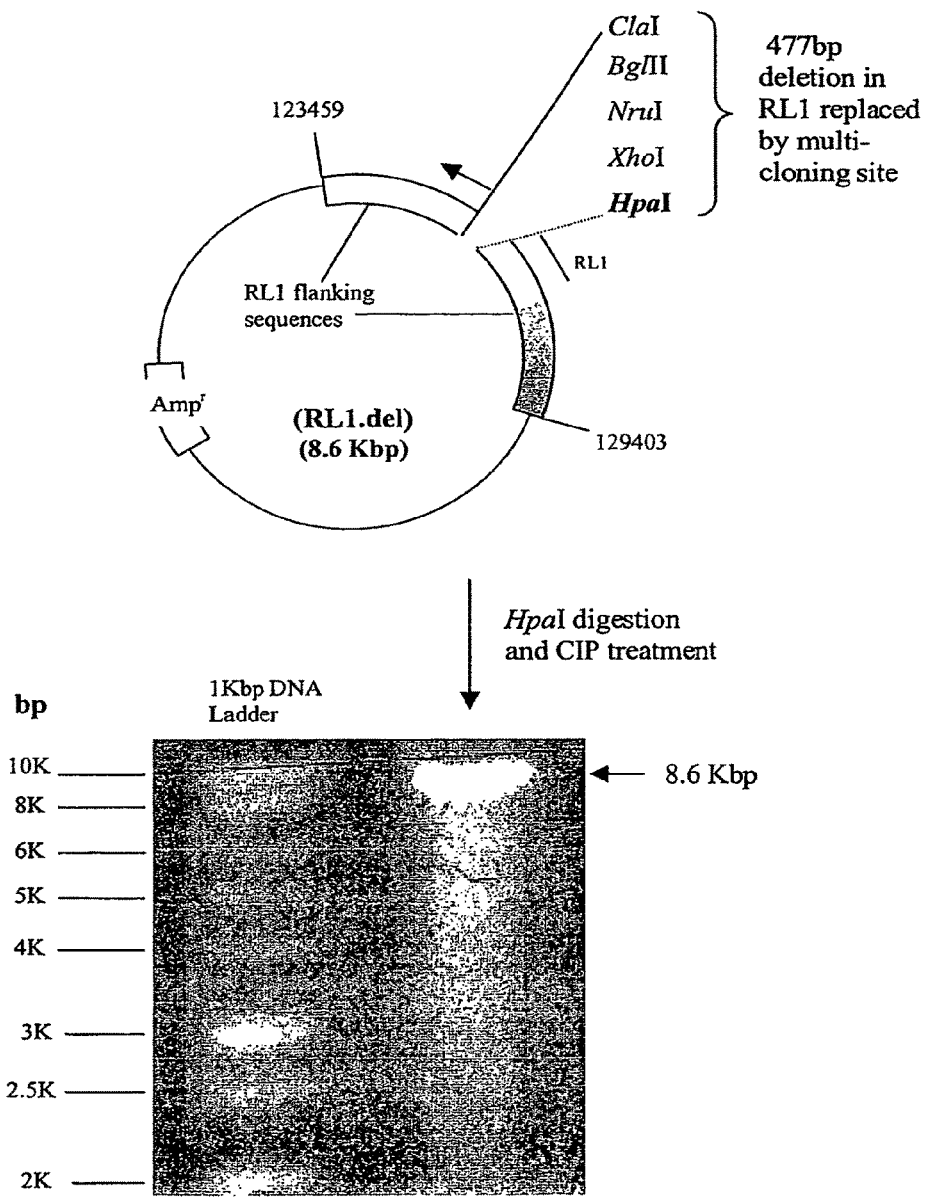
FIG. 2. Agarose gel electrophoresis of HpaI digested, CIP treated, RL1.del. RL1.del was digested with HpaI. The digested DNA was then treated with Calf Intestinal Phosphatase (CIP) to prevent the vector re-annealing to itself in subsequent ligation reactions. A sample of the digested/CIP treated DNA was electrophoresed, beside a 1 Kbp DNA ladder (Promega), on a 1% agarose gel. HpaI linearises the vector at 8.6 Kbp.

1 μg of RL1.del* was digested with 10 units HpaI (Promega) in a suitable volume of 10× buffer (Promega) and nuclease free water (Promega) at 37° C. for 16 hrs. The digested plasmid was then purified using the QIAquick PCR purification kit (Qiagen), treated with 10 units of Calf Intestinal Phosphatase (Promega), in a suitable volume of 10×CIP buffer and nuclease free water for 4 hrs at 37° C., before being purified again using a Qiaquick PCR purification kit. 5 μl of the purified DNA was electrophoresed on a 1% agarose gel to check its concentration (FIG. 2).

Figure 3:
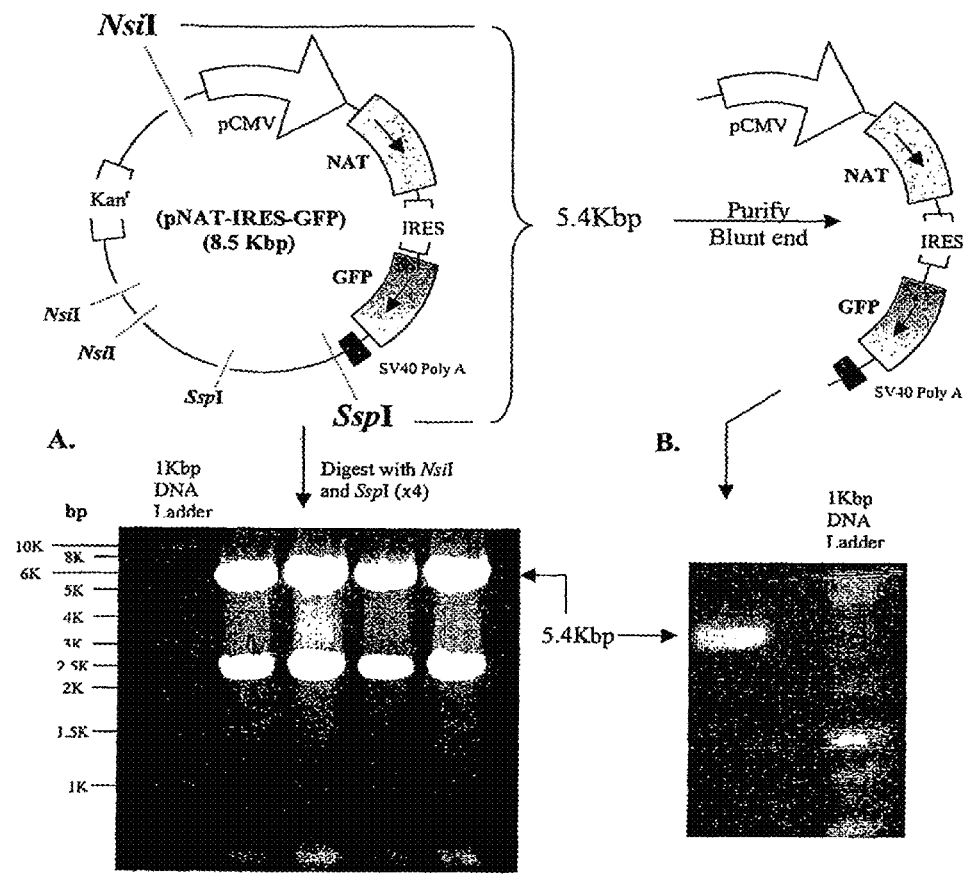
FIG. 3. Agarose gel electrophoresis of NsiI/SspI digested pNAT-IRES-GFP (A) and purified/blunt-ended pCMV-NAT-IRES-GFP-PolyA (B). Four NsiI/SspI digestions of pNAT-IRES-GFP were electrophoresed, beside a 1 Kbp DNA Ladder (Promega) on a 1% agarose gel. The 5.4 Kbp fragments (pCMV-NAT-IRES-GFP-PolyA) were purified from the gel. The purified DNA was blunt ended using Klenow polymerase and a sample electrophoresed on an agarose gel to check its concentration.

4×1 g of pNAT-IRES-GFP** was digested with 10 units of NsiI and 10 units of SspI in a suitable volume of 10× buffer (Promega) and nuclease free water (Promega) at 37° C. for 16 hrs. The reaction mixture was electrophoresed in a 1% agarose gel for 1 hr at 110 volts. The 5.4 Kbp DNA fragment consisting of the CMV IE promoter (pCMV), upstream of the noradrenaline transporter gene (NAT), the encephalomyocarditis virus internal ribosome entry site (IRES), the gene for green fluorescent protein (GFP) and the SV40 polyadenylation sequences (SV40 Poly A), was excised using a sterile scalpel and the DNA purified from the gel using a QIAquick Gel Extraction kit (Qiagen). The eluted DNA was blunt ended using 3 units Klenow Polymerase (Promega) in accordance with the manufacturers instructions and the DNA purified using a QIAquick PCR purification kit (Qiagen). 5 μl of the purified DNA fragment was electrophoresed on a 1% agarose gel to check its concentration (FIG. 3).

Figure 4:
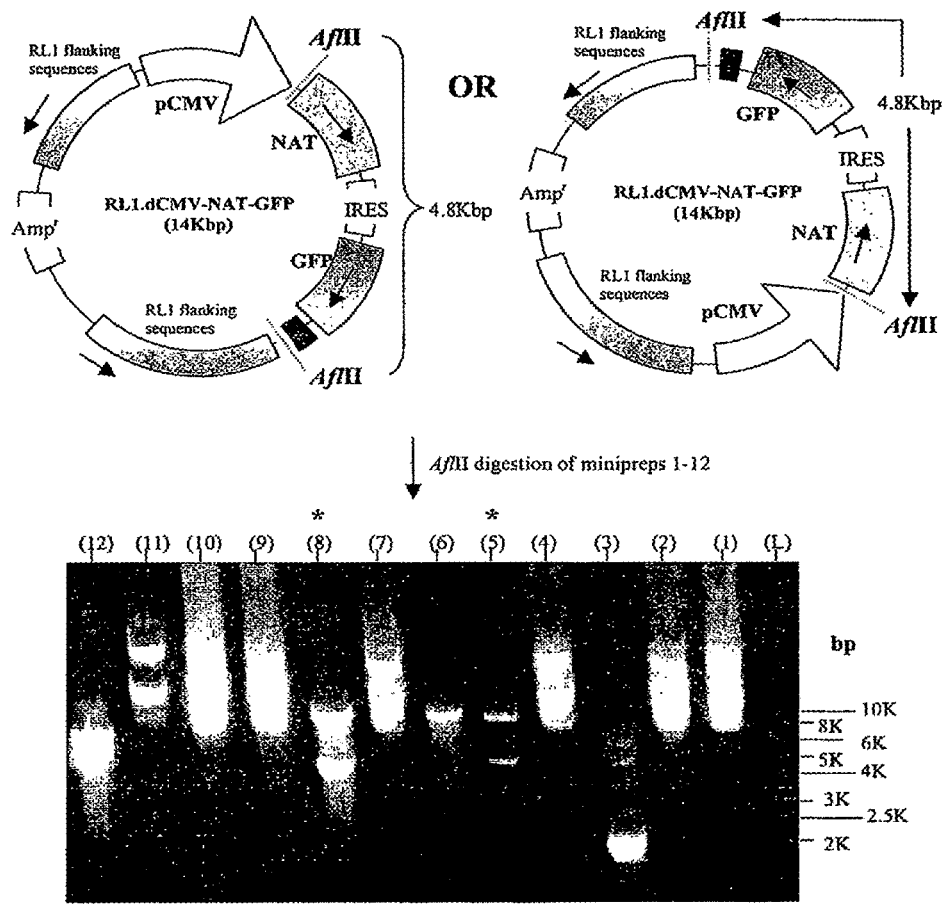
FIG. 4. Identification of RL1.del clones containing the pCMV-NAT-IRES-GFP-PolyA insert. Ligation reactions were set up with the purified, blunt ended pCMV-NAT-IRES-GFP-PolyA fragment and HpaI digested, CIP treated RL1.del. Bacteria were transformed with samples from the ligation reactions and plated out onto LBA (Amp®) plates. Colonies were picked and plasmid DNA was extracted and digested with AflII. Digested samples were electrophoresed, beside a 1 Kbp DNA ladder (L) (Promega), on a 1% agarose gel.

Ligation reactions were carried out in small eppendorf tubes containing 5 units T4 DNA Ligase (Promega), a suitable volume of 10×DNA Ligase Buffer (Promega), nuclease free water (Promega) and various volumes of the HpaI digested/CIP treated RL1.del and blunt ended pCMV-NAT-IRES-GFP-SV40 Poly A DNA, at 16° C. overnight. Competent JM109 bacterial cells (Promega) were then transformed with various aliquots of the ligation reactions***. Colonies formed on the plates were picked, had their plasmid DNA extracted using a Qiagen Plasmid Mini kit and screened for inserts using AflII (New England Biolabs) restriction enzyme analysis. Plasmid DNA containing the insert would produce two fragments of 4.8 Kbp and 9.2 Kbp following digestion with AflII. Two clones (clone 5 and 8) contained the insert (FIG. 4). The orientation of the insert in clone 5 (RL1.dCMV-NAT-GFP) was determined using XhoI restriction enzyme analysis (FIG. 5).

To generate RL1.dIRES-GFP from clone 5, the CMV-NAT portion of the CMV-NAT-IRES-GFP-SV40 PolyA insert was removed by digesting 4×500 ng of clone 5 with 10 units of XhoI in a suitable volume of buffer and water (Promega), overnight at 37° C. The digested DNA was electrophoresed on a 1% agarose gel at 110 volts for 1 hr (FIG. 6A). The 10.2 Kbp fragment consisting of the IRES, the GFP gene, the SV40 PolyA sequences and RL1 flanking sequences in a pGEM3Zf(–) (Promega) backbone, was excised using a sterile scalpel and the DNA purified from the gel using a QIAquick Gel Extraction kit.

Ligation reactions were performed in small eppendorf tubes containing 100 ng-500 ng purified DNA, 3 units T4 DNA Ligase (Promega), a suitable volume of 10×DNA Ligase Buffer (Promega) and nuclease free water (Promega) overnight at 16° C. Competent JM109 bacterial cells (Promega) were then transformed with various aliquots of the ligation reactions***. Colonies formed on the plates were picked, had their plasmid DNA extracted using a Qiagen Plasmid Mini kit and screened using XhoI (Promega) restriction enzyme analysis. Colonies containing plasmid DNA from which CMV-NAT had been removed would produce one fragment of 10.2 Kbp when digested with XhoI. Several positive clones were found, one was isolated, and a large-scale plasmid preparation undertaken using Promega's Wizard Plus Maxipreps kit. The large-scale plasmid preparation was checked by digesting with XhoI (FIG. 6B). This plasmid DNA was subsequently named 'RL1.dIRES-GFP'.

Plasmid RL1.dIRES-GFP has been deposited in the name of Crusade Laboratories Limited having an address at Department of Neurology Southern General Hospital 1345 Govan Road Govan Glasgow G51 5TF Scotland on 3 Sep. 2003 at the European Collection of Cell Cultures (ECACC), Health Protection Agency, Porton Down, Salisbury, Wiltshire, SP4 0JG, United Kingdom under accession number 03090303 in accordance with the provisions of the Budapest Treaty.

RL1.del

*RL1.del was provided by Dr. E. McKie and is the pGEM-3Zf(–) plasmid (Promega) into which has been cloned an HSV-1 fragment (123459-129403) consisting of the RL1 gene and its flanking sequences. The 477 bp PflMI-BstEII fragment of the RL1 gene (125292-125769) has been removed and replaced with a multi-cloning site (MCS) to form RL1.del.

pNAT-IRES-GFP

**pNAT-IRES-GFP was supplied by Dr. Marie Boyd (CRUK Beatson Laboratories) and is the pIRES2-EGFP plasmid (BD Biosciences Clontech) into which she has cloned the bovine noradrenaline transporter (NAT) gene (3.2 Kbp), at the NheI and XhoI sites.

***Transformation of Bacterial Cells

10 μl of a glycerol E. coli stock was added to 10 ml 2YT medium in a 20 ml griener tube. This was placed in a 37° C. shaking incubator for 16-24 hrs until a saturated culture was obtained. 1 ml of this culture was then added to 100 ml of 2YT in a 500 ml sterile glass bottle and placed in the 37° C. shaking incubator for 3 hrs. The bacterial cells were pelleted by centrifugation at 2,000 rpm for 10 minutes (Beckman). The cells were then resuspended in 1/10th volume of transformation and storage buffer (10 mM $MgCl_2$, 10 mM $Mg(SO)_4$, 10% (w/v) PEG 3,500, 5% (v/v) DMSO). The cells were placed on ice for between 10 minutes and 2 hrs, after which time they were considered competent for transformation.

1-10 μl of DNA was mixed with 100 μl of competent bacteria in eppendorf tubes, and the tubes placed on ice for 30 minutes. After this, the samples were 'heat shocked' by incubating the tubes in a 42° C. water bath for exactly 45 seconds before placing them on ice for a further 2 minutes. 1 ml of L-Broth was added, the tube inverted 2-3 times, and the bacteria incubated for 1 hr at 37° C. 100 μl of the transformed bacteria was plated out onto L-broth agar plates containing 100 μg/ml of the appropriate antibiotic (usually ampicillin or kanamycin). Plates were allowed to dry at room temperature, before incubating in an inverted position at 37° C. overnight.

Example 2

Generation of ICP34.5 Null HSV-1 Expressing a Gene Product of Interest and GFP Using Plasmid RL1.dIRES-GFP.

General Approach

Generation of ICP34.5 null HSV-1 expressing a gene product of interest requires insertion of nucleotide sequence encoding the gene product (polypeptide) of interest and desired promoter at the MCS of RL1.dIRES.GFP followed by co-transfection of BHK cells with the linearised plasmid, containing the gene of interest, and HSV DNA. Following homologous recombination viral plaques expressing GFP are identified. FIG. 7 illustrates the method steps involved.

Referring to FIG. 7A plasmid DNA, containing the gene of interest and the desired promoter (X), is digested with restriction endonucleases to release the promoter/gene fragment.

The promoter/gene fragment is purified and cloned into the multi-cloning site (MCS) of RL1.dIRES.GFP forming a shuttle vector suitable for generating oncolytic HSV-1 (FIG. 7B). This vector contains HSV-1 sequences that flank the essential RL1 gene but does not contain the RL1 gene. The plasmid also contains the gene for Green Fluorescent Protein (GFP) downstream of an internal ribosome entry site (IRES). The IRES permits expression of both the gene of interest and the GFP gene from the same upstream promoter.

BHK cells are then co-transfected with linearised RL1.dIRES.GFP, now containing the gene of interest, and HSV-1 DNA (FIG. 7C). Following homologous recombination, designer virus, expressing the gene of interest and GFP, is generated and can be distinguished from wild type virus (also generated but not expressing GFP) under a fluorescence microscope.

Viral plaques, expressing GFP (and hence the gene of interest), are picked under the fluorescence microscope and purified until all wild-type HSV-1 has been removed. The recombinant HSV-1 is considered 100% pure when all the viral plaques are expressing GFP (FIG. 7D).

Once the recombinant virus is completely pure, an isolated plaque is picked and a highly concentrated stock is grown and titrated (FIG. 7E). Oncolytic HSV-1, expressing a gene product of interest from a selected promoter, is then ready for characterisation and in vitro examination of its tumour killing potential.

Materials and Methods

To generate recombinant ICP34.5 null HSV-1 expressing a gene of interest and GFP, requires the gene of interest and a suitable promoter to be cloned into the MCS of RL1.dIRES-GFP in the forward orientation with respect to the GFP gene in this plasmid. Once this has been achieved the plasmid is linearised (i.e. digested with a restriction enzyme that cuts only once, usually SspI or ScaI) in an irrelevant region. 80% confluent BHK cells in 60 mm petri dishes are then co-transfected with HSV-1 DNA and linearised plasmid DNA as described below.

To generate replication restricted HSV-1, expressing the gene of interest and GFP, the gene of interest must be cloned into RL1dIRES-GFP downstream of a suitable promoter (e.g. CMV IE). The promoter is required upstream of the gene of interest for the production of a bicistronic mRNA transcript. The IRES sequence between the two open reading frames in the transcript functions as a ribosome binding site for efficient cap-independent internal initiation of translation. The design enables coupled transcription of both the gene of interest and GFP, followed by cap-dependent initiation of translation of the first gene (gene of interest) and IRES-directed, cap-independent translation of GFP. Co-ordinate gene expression is thus ensured in this configuration.

Co-Transfection of Virus and Plasmid DNA by $CaPO_4$ and DMSO Boost

HSV-1 ($17^+$) DNA and 0.1-1 μg linearized SMART cassette containing the gene and promoter of interest is pipetted into 1.5 ml eppendorf tubes containing 1 μl of calf thymus DNA (10 g/ml) and an appropriate volume of distilled water to give a final volume of 165 μl. The solutions are very gently mixed using a 200 μl pipette tip. 388 μl of HEBS, pH 7.5, (130 mM NaCl, 4.9 mM KCl, 1.6 mM $Na_2HPO_4$, 5.5 mM D-glucose, 21 mM HEPES) is then added, the solution mixed, before adding 26.5 μl of 2M $CaCl_2$ dropwise and flicking the eppendorf tube two or three times. The samples are left at room temperature for 10-15 minutes then added dropwise to 80% confluent BHK's in 60 mm petri dishes from which the medium has been removed. Following incubation at 37° C. for 45 minutes, the cells are overlaid with 5 ml of ETC10 and incubated at 37° C. Three to four hours later, the media is removed and the plates washed with ETC10. For exactly 4 minutes, the cells are overlaid with 1 ml 25% (v/v) DMSO in HEBS at room temperature. After the 4 minutes, the cells are immediately washed three times with 5 ml ETC10 before overlaying with 5 ml of ETC10 and returning to the incubator. The following day, fresh medium is added to the cells. Two days later, when cpe is evident, cells are scraped into the medium, transferred to small bijoux and sonicated thoroughly. The sample is then stored at −70° C. until required (see section below on plaque purification).

N.B. The volume of virus DNA to add is determined by undertaking the above procedure without plasmid DNA, using a range of virus DNA volumes and choosing the volume that gives the greatest number of viral plaques on the BHK monolayer after 2 or 3 days.

Plaque Purification

Sonicated samples from co-transfection plates are thawed and serially diluted 10 fold in ETC10. 100 μl from neat to the $10^5$ dilution is plated out on confluent BHK's in 60 mm petri dishes from which the media has been removed. After 45 minutes incubation at 37° C., the cells are overlaid with 5 ml EMC10 and incubated at 37° C. for 48 hrs. The plates are then checked for the presence of viral plaques and those dishes with the fewest, most separated plaques are placed under a fluorescent stereomicroscope. Recombinant virus, designed to express the green fluorescent protein (GFP) in addition to the gene of interest, can clearly be distinguished from wild type virus using a GFP filter. Fluorescent plaques are picked using a 20 μl pipette and placed (including the tip) into an eppendorf tube containing 1 ml ETC10. The sample is thoroughly sonicated before making serial 10 fold dilutions in ETC10 and repeating the above purification procedure. The process is repeated typically 3-4 times until every plaque on the BHK monolayer is fluorescent. Once this has been achieved, 50 μl of this sample is used to infect BHK's in roller bottles, in 50 ml ETC10, and a virus stock grown.

Tissue Culture Media

BHK21/C13 cells are grown in Eagle's medium (Gibco) supplemented with 10% newborn calf serum (Gibco) and 10% (v/v) tryptose phosphate broth. This is referred to as ETC10. For virus titrations and plaque purification, EMC10 (Eagles medium containing 1.5% methylcellulose and 10% newborn calf serum) is used to overlay the cells.

Example 3

Construction of HSV1716/CMV-asSCCRO/GFP

General Approach

HSV1716/CMV-asSCCRO/GFP was generated by first digesting pUSEamp-asSCCRO with SspI and XhoI and purifying the 1.96 Kbp fragment generated from the digestion. The 1.96 kbp SspI/XhoI fragment comprises DNA antisense to squamous cell carcinoma related antigen (asSCCRO), downstream of the CMV IE promoter (pCMV). This fragment was cloned into the MCS of the RL1.dIRES-GFP smart cassette, in the forward orientation with respect to the GFP gene in RL1.dIRES-GFP (FIG. 8). The resultant plasmid, named RL1.dCMV-asSCCRO-GFP, was then linearised and recombinant virus generated and purified as described in Example 2. The plasmid pUSEamp-asSCCRO was obtained from Bhuvanesh Singh, Memorial Sloan Kettering Cancer Center, New York.

Materials and Methods

2 μg of the RL1.dIRES-GFP plasmid was then digested with 15 units of BglII (Promega), in a suitable volume of 10× buffer (Promega) and nuclease free water (Promega), at 37° C. for 16 hrs. The digested plasmid was then purified using the QIAquick PCR purification kit (Qiagen), treated with 5 units of Klenow polymerase (Promega) for 20 minutes at room temperature, then purified again. The purified DNA was then added to 10 units of Calf Intestinal Phosphatase (Promega), in a suitable volume of 10×CIP buffer and nuclease free water for 4 hrs at 37° C., before being purified again using the QIAquick PCR purification kit. 5 μl of the purified DNA was electrophoresed on a 1% agarose gel to check its concentration (FIG. 9).

4×1 g of pUSEamp-asSCCRO was digested with 10 units of SspI and 10 units of XhoI (Promega), in a suitable volume of 10× buffer (Promega) and nuclease free water (Promega), at 37° C. for 16 hrs. The reaction mixture was electrophoresed in a 1% agarose gel for 1 hr at 110 volts. The 1.96 Kbp DNA fragment, consisting essentially of the CMV promoter upstream of DNA antisense to SCCRO (pCMV-asSCCRO), was excised using a sterile scalpel and the DNA purified from the gel using a QIAquick Gel Extraction kit (Qiagen). The purified DNA was blunt ended using 5 units of Klenow polymerase (Promega) for 20 minutes at room temperature, then purified again. 5 μl of the purified DNA fragment was electrophoresed on a 1% agarose gel to check its concentration (FIG. 10).

Ligation reactions were carried out in small eppendorf tubes containing 5 units T4 DNA Ligase (Promega), a suitable volume of 10×DNA Ligase Buffer (Promega), nuclease free water (Promega) and various volumes of the BglII digested/blunt ended/CIP treated RL1.dIRES-GFP plasmid and blunt ended pCMV-asSCCRO, at 16° C. overnight. Competent JM109 bacterial cells (Promega) were then transformed with various aliqouts of the ligation reactions. Colonies formed on the plates were picked, had their plasmid DNA extracted using a Qiagen Plasmid Mini kit and screened for inserts using BglII (Promega) restriction enzyme analysis. RL1.dIRES-GFP plasmid DNA containing the pCMV-asSC-CRO insert would produce two fragments of 10.8 Kbp and 1.4 Kbp following digestion with BglII. One clone (clone 11) was found to contain the insert (FIG. 11). The pCMV-asSCCRO insert could have been cloned into RL1.dIRES-GFP in two orientations. To confirm that the pCMV-asSCCRO fragment had been cloned into RL1.dIRES-GFP in the desired orientation, clone 11 was digested with 10 units of NruI (Promega), in a suitable volume of 10× buffer (Promega) and nuclease free water (Promega), at 37° C. for 16 hrs. If the insert was in the correct orientation, a fragment of 1.64 Kbp would be generated. As a 1.64 Kbp fragment was generated following digestion with NruI (FIG. 12), it was confirmed that pCMV-asSCCRO had been cloned in the desired orientation. This plasmid (clone 11) was named 'RL1.dCMV-asSCCRO-GFP'.

0.1-1 μg of RL1.dCMV-asSCCRO-GFP was linearized by digesting with 10 units of ScaI (Promega), in a suitable volume of 10× buffer (Promega) and nuclease free water (Promega), at 37° C. for 16 hrs. A sample (5 μl) of the digested DNA was electrophoresed on a 1% agarose gel for 1 hr at 110 volts to check that it had been linearized. 80% confluent BHK cells were then co-transfected with a suitable volume of the remaining linearised DNA and HSV-1 DNA. Recombinant HSV-1, expressing GFP (and hence asSCCRO), was identified and purified using a fluorescent microscope and a virus stock, named HSV1716/CMV-asSCCRO/GFP, was grown and titrated on BHK cells (FIG. 13).

HSV1716/CMV-asSCCRO/GFP has been deposited as 'HSV1716asSCCRO' in the name of Crusade Laboratories Limited having an address at Department of Neurology Southern General Hospital 1345 Govan Road Govan Glasgow G51 5TF Scotland on 19 May 2004 at the European Collection of Cell Cultures (ECACC), Health Protection Agency, Porton Down, Salisbury, Wiltshire, SP4 0JG, United Kingdom under accession number 04051901 in accordance with the provisions of the Budapest Treaty on the International Recognition of the Deposit of Microorganisms for the Purposes of Patent Procedure (herein referred to as the 'Budapest Treaty').

Example 4

The Use of HSV1716asSCCRO as a Novel Therapeutic Agent for Head and Neck Squamous Cell Cancer The inventors believe that insertion of the antisense to SCCRO into the herpes simplex virus HSV1716 may provide a virus with a dual hit mechanism of cell kill. This would involve virus induced cell death via cytolysis in addition to cell death via downregulation of endogenous SCCRO expression.

The HSV1716asSCCRO virus was constructed, amplified and purified in accordance with the present invention. Following this, in vitro and in vivo analysis was carried out on a series of head and neck squamous cell cancer (HNSCC) cell lines. HNSCC cell lines studied were SCC15, 1483, 1186, 1386, 1986 and 584. The relative expression of SCCRO protein expression in these cell lines was initially determined by western blotting. This showed the cell lines SCC15, 1483 and 1186 had high levels of expression of SCCRO, 1386 intermediate expression and 1986, 584 low expression. All cell lines were then infected with HSV1716 or HSV1716asSCCRO viruses and cytotoxicity determined by LDH release cytotoxicity assay at MOI (multiplicity of infection) of 1 and 5 pfu/cell (FIGS. 14, 15 and 16). Viral proliferation was determined by serial plaque assays at an MOI of 1 pfu/cell (FIG. 17) and infectivity determined by green fluorescent protein (gfp) using HSV1716gtp virus (FIG. 18). In the cell lines with low or intermediate expression (1986, 584, 1386) cytotoxicity increased in a dose dependent fashion with both viruses but there was no significant difference in cytotoxicity between the 2 viruses. Viral proliferation assays (FIG. 17) showed an increase in viral production over a range of $10^2$ to $10^4$ with equivalent proliferation with both viruses. In the cell lines with high expression of SCCRO the inventors found that the cell line SCC15 showed enhanced cytotoxicity with the HSV1716asSCCRO virus. This observation occurred 12 hours post viral infection which is premature for virus induced cell death by a cytolytic mechanism. In addition, virus proliferation of the 2 viruses was equivalent with an increase in virus production of $10^4$ for both viruses. These results suggested that the enhanced cell kill at 12 hours was by an alternative mechanism possibly by downregulation of the endogenous high expression of SCCRO by antisense SCCRO expression. To investigate this hypothesis the inventors analysed the cell lines SCC15 (high expression) and 584 (low expression) post virus infection by serial protein expression over a 36 hour period. Cells were infected at an MOI of 1 pfu/cell with HSV1716 or HSV1716asSCCRO and cells harvested and lysed for protein at 12, 24 and 36 hours post infection. Western blotting of the cell line SCC15 showed downregulation of SCCRO protein at 12 hours with HSV1716asSCCRO but not in 584 (see FIG. 19). This suggested that this was the mechanism by which HSV1716asSCCRO had enhanced efficacy in cell line SCC15.

In vivo studies were then carried out in the cell lines SCC15 and 584. Subcutaneous tumour were grown in athymic nude mice and injected intratumorally with a single injection of HSV1716, HSV1716asSCCRO or PBS control and tumour sizes monitored at serial time points (FIGS. 20 and 21). In SCC15, efficacy was enhanced with HSV1716asSCCRO compared to HSV1716. All 6 mice injected with HSV1716asSCCRO showed complete responses by 21 days post infection. Inhibition of tumour growth occurred with HSV1716 with only 3/6 mice showing a complete response over a 48 day follow up period. In the cell line 584, both viruses were able to inhibit tumour growth but neither virus produced a complete response in any mouse xenograft injected. This in vivo data was further evidence that HSV1716asSCCRO was a more potent antitumour agent than HSV1716 in the cell line SCC15 with high SCCRO expression.

These results suggest that HSV1716 and HSV1716asSCCRO has great potential as useful therapeutic agents in the treatment of recurrent or locally advanced head and neck cancer by direct intratumoral injection. However, this data also suggests that HSV1716asSCCRO may augment anti-tumour activity in SCCRO over-expressing tumours. Since SCCRO is overexpressed in a significant number of squamous cell cancers of the head and neck this modified virus may be particularly efficacious in this disease. Therefore, the inventors believe that HSV1716asSCCRO will be an important therapeutic agent in head and neck cancer patients with locally advanced or recurrent head and neck cancer, particularly as these cancers are amenable to direct intratumoural injection.

Example 5

Construction of HSV1716 Variants Expressing siRNA

General Strategy

A plasmid that contains the siRNA construct designed to target expression of the SCCRO gene (SEQ ID No. 5) and designated 339i was provided by Dr Bhuv Singh, MSKCC, New York. A plasmid encoding a control siRNA (SEQ ID No 6), designated Coni, was also provided.

Both siRNA constructs were in the vector pSNRG and their expression is driven by the RNA polIII H1 promoter. RNA polIII only transcribes short RNA molecules and the H1 promoter would be insufficient to drive expression of IRES-gfp from the normal recombinant virus producing shuttle vector RL1-del.IRES.gfp so an alternative cloning strategy was adopted.

A cassette was constructed in the following manner. The 1.3 kbp blunt-ended EcoRI/AflII fragment that contains the PGK promoter/GFP gene was obtained by restriction digestion followed by Klenow treatment from the vector pSNRG and cloned into the RL1-del vector cut with the restriction enzyme NruI that generates blunt ends. Successful insertion of the PGK/GFP DNA was confirmed by BamHI digestion and the orientation of the inserted DNA identified using the unique XhoI site in RL1-del and the BsrGI site at the 3' end of PGK/GFP. Plasmids with PGK/GFP in both forward and reverse orientation were obtained and the plasmids were designated RL1-dPGK/GFPfor and RL1-dPGK/GFPrev. Expression of GFP was confirmed in BHK cells transfected with the forward and reverse orientation plasmids.

Thus, sequences of interest along with their own promoters (in this arrangement it is preferred that a different promoter is used to drive transcription of the nucleotide sequence of interest and marker) can then be cloned into either RL1-dPGK/GFPfor or RL1-dPGK/GFPrev in either orientation using the remaining unique BglII, XhoI or HpaI unique restriction enzyme sites. The resulting plasmid can be used to derive recombinant HSV in which the marker GFP gene and the gene of interest are expressed independently from their own promoters Materials and Methods In the pSNRG plasmid and adjacent to the H1/siRNA coding sequence is a green fluorescent protein (gfp) expression cassette comprising the gfp gene with a Phosphoglycerokinase (PGK) promoter. Using the restriction enzymes HindIII and AflII sequentially, the 1.6 kbp DNA fragment that contains the H1/siRNA and PGK/EGFP expression cassettes were excised from their Coni and 339i plasmids. The 1.6 kbp DNA fragment was purified from a 1% agarose gel and blunt-ended by incubation with Klenow DNA polymerase for 30 minutes at 30° C. The blunt-ended fragment was ligated into the RL1-del shuttle vector which had been digested with the restriction enzyme Nru1 that produces a blunt-ended cut. Before ligation the Nru1-cut RL1-del was gel purified and phosphatase-treated using Calf Intestinal Alkaline Phosphatase. After an overnight ligation with either the blunt-ended 339i or Coni DNA fragments with the blunt-ended RL1-del plasmid, the reaction mix was used to transform DH5alpha cells and these were plated-out on LB amp plates. After overnight incubation at 37° C., individual clones from each of the LB amp plates were grown overnight in 3 ml of LB broth and plasmid DNA extracted.

To screen for recombinants, plasmids were initially digested with BamHI, as insertion of the H1/siRNA and PGK/gfp cassette increases the size of the RL1 BamHI fragment in the plasmid from 5.4 kbp to 7.0 kbp. For both Coni and 339i ligations 1/24 clones screened demonstrated a 7.0 kbp BamHI fragment and the presence of the H1/siRNA and PGK/EGFP cassette in these plasmids was confirmed by EcoR1, EcoR1/HindIII and EcoR1/SalI digests, the inserted H1/siRNA and PGK/EGFP cassette introduces a novel EcoR1 site into the RL1-del vector.

From a glycerol stock of the positive 339i and Coni clones, additional plasmid was prepared and used to transfect BHK cells. Fifty microlitres (50 µl) of plasmid was mixed with 6 µl lipofectamine 2000 in a final volume of 100 µl serum free medium and used to transfect BHK cells plated out on a 13 mm glass coverslip in a 24-well plate. After 48 hrs of transfection the cells were washed once in PBS, incubated for 2 hrs in 4% paraformaldehyde, washed once more in PBS and mounted on microscope slides using Vectashield. The presence of c5% gfp-positive cells following transfection with the RL1-del/339i and RL1-del/Coni plasmids confirmed the presence of the PGK/GFP cassette.

The RL1-del/339i and RL1-del/Coni plasmids were linearized using either of the restriction enzymes ScaI and XmnI and the linearized plasmid was used along with viral DNA to transfect BHK cells plated out to c80% confluency in 60 mm dishes. To 100 µl of linearized plasmid or undigested circular plasmid, 50 µl of HSV-1 strain 17+ DNA was added along with 20 µl lipofectamine 2000 in a final volume of 500 µl serum free medium and the mix added to the BHK cells. After 4 hrs of transfection, the cells were shocked with 25% DMSO in HBSS for exactly 4 minutes, washed ×3 with medium and returned to 37° C. incubation in 5 ml of medium for 48 hrs. Viral cpe was evident after 48 hrs and the cells and medium were harvested together, sonicated and stored at −80° C. Undiluted medium/cells and 4×10-fold dilutions were plated out on BHK cells and, after 48 hrs, viral plaques were examined by fluorescence microscopy for gfp expression. On the undiluted plate from cells transfected with XmnI-linearized plasmid >100 gfp-positive plaques were observed for both Coni and 339i indicating a high degree of recombination. Interestingly, recombination, but at a lower frequency (c50 plaques/plate), was observed for the transfected circular plasmid but recombination with the ScaI-linearized plasmid was very low (<5 plaques/plate).

Using the highest dilution at which gfp-positive plaques were clearly visible (the PGK/GFP cassette gave a very strong fluorescent signal), two plaques each of Coni and 339i viruses were picked using a sterile pipette tip, placed in 1 ml medium, sonicated for 1 minute and stored at −80° C. Plaques were then subjected to 6 rounds of plaque purification, after the 6$^{th}$ round no wild type, non-gfp expressing plaques were visible and 6 plaques each of Coni or 339i virus were picked for Southern blotting.

Each of the six plaques of Coni and 339i virus was used to infect a T175 flask of Vero cells, after 72 hrs of infection virus was harvested and titred. For 3 each of the Coni and 339i viruses that gave the highest titres 0.5 ml was used to infect a second T175 flask for 24 hrs. Viral DNA was then harvested from each of the 6 flasks. The BamHI-digested viral DNA was Southern blotted with the Alu/Rsa RL1 probe and the band pattern compared to wild type and HSV1716 DNA digested also with BamHI. A novel c6 kbp band, consistent with the insertion of the 1.6 kbp H1/siRNA and PGK/GFP cassette in the RL1 locus, was clearly visible in all six viral isolates and no wild type bands were detected. Stocks of the Coni and 339i viruses that gave the strongest signal on Southern blotting were produced.

REFERENCES

1. B L Liu, M Robinson, Z-Q Han, R H Branston, C English, Preay, Y McGrath, S K Thomas, M Thornton, P Bullock, C A Love and R S Coffin; Gene Therapy (2003) 10, 292-303.
2. WO 92/13943
3. A Dolan, E Mckie, A R Maclean, D J McGeoch; Journal of General Virology (1992) 73 971-973.
4. Aidan Dolan, Fiona E Jamieson, Charles Cunnigham, Barbara C Barnett Duncan J McGeoch; Journal of Virology March 1998 2010-2021.
5. Joany Chou, Earl R Kern, Richard J Whitley, Bernard Roizman; Science (1990) 250 1262-1265.
6. Coffin R S, MacLean A R, Latchman D S, Brown S M; gene therapy (1996) October 3(10) 886-91.
7. McKie E A, Hope R G, Brown S M, Maclean A R; Journal of General Virology, (1994) April 75(Pt4) 733-41.
8. McKay E M, McVey B, Marsden H S, Brown S M, MacLean A R; Journal of general Virology, (1993) November 74(Pt11) 2493-7.
9. Joany Chou, Bernard Roizman; Journal of Virology; (1990) March 1014-1020.
10. Green, N. K., Youngs, D. J, J. P. Neoptolemos, F. Friedlos, R. J. Knox, C. J. Springer, G. M. Anlezark, N. P. Michael, R. G. Melton, M. J. Ford, L. S. Young, D. J. Kerr, and P. F. Searle; Cancer Gene Therapy (1997) 4:229-238.
11. Cherry L. Estilo, Pornchai O-charoenrat, Ivan Nagai, Snehal G. Patel, Pabbathi G. Reddy, Su Dao, Ashok R. Shaha, Dennis H. Kraus, Jay O. Boyle, Richard J. Wong, David G. Pfister, Joseph M. Huryn, Ian M. Zlotolow, Jatin P. Shah and Bhuvanesh Singh; Clinical Cancer Research (June 2003) Vol. 9 2300-2306.
12. Ganly I, Kaye S B. Recurrent head and neck cancer—current therapy and future prospects. *Annals of Oncology* (2000), 11:1-6.
13. Ganly I, Soutar D S, Kaye S B. Current role of gene therapy in head and neck cancer. *European J of Surgical Oncology* (2000), 26:338-343.
14. Ganly I, Kirn D, Soutar D, Eckardt G, Otto R, Robertson A G, Park O, Heise C, Von Hoff D D, Kaye S B. A phase I study of Onyx-015, an E1B attenuated adenovirus, administered intratumourally in patients with recurrent tumours of the head and neck. *Clinical Cancer Research* (2000), 6:798-806.
15. Khuri F, Nemunaitis J, Ganly I, Arseneau J, Tannock I, Romel L, Gore M, Ironside J, Heise C, Randley B, Gillenwater A, Bruso P, Kaye S B, Hong W K, Kirn D H. Controlled trial of intratumoural ONYX-015, a selectively replicating adenovirus, in combination with cisplatin and 5-fluorouracil in patients with recurrent head and neck cancer. *Nature Medicine* (2000) 6(8): 879-885.
16. Heise C, Sampson-Johannes A, Williams A, McCormick F, Von Hoff D and Kirn D H. Onyx-015 an E1B gene attenuated adenovirus causes tumour specific cytolysis and antitumoural efficacy that can be augmented by standard chemotherapeutic agents. Nature Medicine 3, 639-645.
17. MacLean A R, Fareed M U, Robertson L, Harland J, and Brown S M. (1991). Herpes simplex virus type 1 deletion variants 1714 and 1716 pinpoint neurovirulence related sequences in Glasgow strain 17$^+$ between immediate early gene 1 and the 'a' sequence. *Journal of General Virology* 72, 631-639.
18. Brown S M, Harland J, MacLean A R, Podlech J. and Clements J B. (1994). Cell type and cell state determine differentiated in vitro growth of non-neurovirulent ICP34.5 negative herpes simplex virus. *Journal of General Virology* 75, 2367-2377.

19. McKie E A, MacLean A R, Lewis A D, Cruickshank G, Rampling R, Barnett S C, Kennedy P G E and Brown S M. (1996) Selective in vitro replication of herpes simplex virus type 1 (HSV1), ICP34.5 null mutants in primary human CNS tumours-evaluation of a potentially effective clinical therapy. *British Journal of Cancer* 74, 745-752.
20. Randazzo B, Kesari S, MacLean A R, Brown S M. and Fraser N W. (1995). Treatment of experimental intracranial murine melanoma with the neuroattenuated HSV1 mutant 1716. *Virology* 211, 94-101.
21. Kesari S, Randazzo B P, Valyi-Nagy T, Huang Q S, Brown S M, MacLean A R, Lee V M-Y, Trojanowski J Q. and Fraser N W. (1995). A mutant herpes simplex virus replicates in brain tumours but not in neurons derived from a human embryonal carcinoma cell line. *Laboratory Investigation* 73, 636-648.
22. Randazzo B P, Kucharczuk J C, Litzky L A, Kaiser L R, Brown S M, MacLean A R, Albelda S M. and Fraser N W. (1996). Herpes simplex 1716—an ICP34.5 mutant is severely replication restricted in human skin xenografts in vivo. *Virology* 223, 392-396.
23. Lasner T M, Kesari S, Brown S M, Lee V M-Y, Fraser N W. and Trojanowski J Q. (1996). Herpes simplex virus type 1 (HSV1) mutants for the treatment of childhood brain tumours. *Journal of Neuropathology and Experimental Neurology* 55, 1259-1269
24. Kucharczuk J C, Randazzo B, Chang M Y, Amin K M, Elshami A A, Sterman D H. Rizk N P, Molnar-Kimber K L, Brown S M, MacLean A R, Litzky L A, Fraser N W, Albelda S M. and Kaiser L R. (1997). Use of a "replication restricted" herpes virus to treat experimental human malignant mesothelioma. *Cancer Research,* 57, 466-471.
25. Randazzo B P, Bhat M G, Kesari S, Fraser N W. and Brown S M. (1997). Treatment of experimental subcutaneous human melanoma with a replication restricted herpes simplex virus mutant. *Journal of Investigative Dermatology,* 108, 933-937.
26. Rampling R, Cruickshank G, Papanastassiou V, Nicoll J, Hadley D, Petty R, Maclean A, Harland J, McKie E, Mabbs R. & Brown S M. (2000). Toxicity evaluation of replication competent herpes simplex virus (ICP 34.5 null mutant 1716) in patients with recurrent malignant glioma. *Gene Therapy* 7, 859-866.

The invention claimed is:

1. A method of enhancing the efficacy of in vivo lysis or killing of tumor cells that overexpress the squamous cell carcinoma related oncogene (SCCRO) by a non-neurovirulent oncolytic herpes simplex virus, the method comprising the step of administering a non-neurovirulent oncolytic herpes simplex virus to tumor cells in a patient in need of treatment, wherein the herpes simplex virus genome comprises a nucleic acid encoding an antisense to the squamous cell carcinoma related oncogene (asSCCRO), which squamous cell carcinoma related oncogene comprises the nucleotide sequence of SEQ ID NO: 1 or SEQ ID NO: 3; and wherein the nucleic acid in the herpes simplex virus genome encodes a nucleotide sequence having at least 95% sequence identity to:

(i) a nucleotide sequence complementary to the polynucleotide sequence of SEQ ID No. 1 or 3; or
(ii) the mRNA transcript of SEQ ID No. 1 or 3, wherein the tumor cells overexpress the squamous cell carcinoma related oncogene (SCCRO), and wherein the herpes simplex virus lyses or kills tumor cells that overexpress SCCRO with enhanced efficacy.

2. The method according to claim 1 wherein said nucleic acid encodes the human asSCCRO.

3. The method according to claim 1 wherein said herpes simplex virus genome further comprises a regulatory sequence operably linked to said nucleic acid encoding an antisense to the squamous cell carcinoma related oncogene (asSCCRO), wherein said regulatory sequence has a role in controlling transcription of said asSCCRO.

4. The method according to claim 1 wherein said nucleic acid is located in at least one RL1 locus of the herpes simplex virus genome.

5. The method according to claim 1 wherein said nucleic acid is located in, or overlaps, at least one of the ICP34.5 protein coding sequences of the herpes virus genome.

6. The method according to claim 1 wherein the herpes simplex virus is a mutant of one of HSV-1 strains 17 or F or HSV-2 strain HG52.

7. The method according to claim 1 wherein the herpes simplex virus is a mutant of HSV-1 strain 17 mutant 1716.

8. The method according to claim 1 wherein the herpes simplex virus is an ICP34.5 null mutant.

9. The method according to claim 1 wherein the herpes simplex virus lacks at least one expressible ICP34.5 gene.

10. The method according to claim 1 wherein the herpes simplex virus lacks only one expressible ICP34.5 gene.

11. The method according to claim 1, wherein the herpes simplex virus is HSV1716asSCCRO (ECACC accession number 04051901).

* * * * *